US009212180B2

(12) United States Patent
Grembecka et al.

(10) Patent No.: US 9,212,180 B2
(45) Date of Patent: Dec. 15, 2015

(54) MENIN-MLL INHIBITORS AND METHODS OF USE THEREOF

(71) Applicants: THE REGENTS OF THE UNIVERSITY OF MICHIGAN, Ann Arbor, MI (US); VANDERBILT UNIVERSITY, Nashville, TN (US)

(72) Inventors: Jolanta Grembecka, Ann Arbor, MI (US); Tomasz Cierpicki, Ann Arbor, MI (US); Sunil Kumar Upadhyay, Ypsilanti, MI (US); Shaun R. Stauffer, Brentwood, TN (US); Rocco D. Gogliotti, Kingston Springs, TN (US); Timothy J. Senter, Nashville, TN (US)

(73) Assignees: THE REGENTS OF THE UNIVERSITY OF MICHIGAN, Ann Arbor, MI (US); VANDERBILT UNIVERSITY, Nashville, TN (US)

(*) Notice: Subject to any disclaimer, the term of this patent is extended or adjusted under 35 U.S.C. 154(b) by 0 days.

(21) Appl. No.: 14/302,219

(22) Filed: Jun. 11, 2014

(65) Prior Publication Data
US 2014/0371239 A1 Dec. 18, 2014

Related U.S. Application Data

(60) Provisional application No. 61/834,178, filed on Jun. 12, 2013.

(51) Int. Cl.
*A61K 31/445* (2006.01)
*C07D 401/06* (2006.01)
*C07D 417/06* (2006.01)
*C07D 295/088* (2006.01)
*C07D 401/12* (2006.01)
*C07D 401/14* (2006.01)
*C07D 211/22* (2006.01)
*C07D 211/26* (2006.01)

(52) U.S. Cl.
CPC ............ *C07D 417/06* (2013.01); *C07D 211/22* (2013.01); *C07D 211/26* (2013.01); *C07D 295/088* (2013.01); *C07D 401/06* (2013.01); *C07D 401/12* (2013.01); *C07D 401/14* (2013.01)

(58) Field of Classification Search
CPC .......................... C07D 401/06; C07D 417/06
USPC .......... 546/194, 209, 210, 230; 514/316, 318, 514/326, 256; 544/335
See application file for complete search history.

(56) References Cited

U.S. PATENT DOCUMENTS 4,810,713 A    3/1989  Yanni
4,950,674 A *  8/1990  Yanni et al. ............ 514/317
5,070,087 A    12/1991 Teng et al.
5,432,175 A *  7/1995  Piwinski et al. ........ 514/253.09
2011/0009405 A1  1/2011 Rewcastle et al.

OTHER PUBLICATIONS

Yanni et al. "Preparation of aralkylpiperidine . . . " CA115:49413 (1991).*
Patani et al. "Bioisosterism: a rational . . . " Chem. Rev. v.96 p. 3147-3176 (1996).*
Walsh et al. "Synthesis and antiallergy . . . " J. Med. Chem. 32, 105-118 (1989).*
Balgobind et al., "The heterogeneity of pediatric MLL-rearranged acute myeloid leukemia." Leukemia. Aug. 2011; 25 (8):1239-48.
Butler et al., "The HRX proto-oncogene product is widely expressed in human tissues and localizes to nuclear structures." Blood. May 1, 1997; 89(9):3361-70.
Caslini et al., Interaction of MLL amino terminal sequences with menin is required for transformation. Cancer Res. Aug. 1, 2007; 67(15):7275-83.
Chandrasekharappa et al., "Positional cloning of the gene for multiple endocrine neoplasia-type 1." Science. Apr. 18, 1997; 276(5311):404-7.
Daigle et al., "Selective killing of mixed lineage leukemia cells by a potent small-molecule DOT1L inhibitor." Cancer Cell. Jul. 12, 2011; 20(1):53-65.
Dimartino & Cleary, "Mll rearrangements in haematological malignancies: lessons from clinical and biological studies." Br J Haematol. Sep. 1999; 106(3):614-26.
Dorrance et al., "Mll partial tandem duplication induces aberrant Hox expression in vivo via specific epigenetic alterations." J Clin Invest. Oct. 2006; 116(10):2707-16.
Faber et al., "HOXA9 is required for survival in human MLL-rearranged acute leukemias." Blood. Mar. 12, 2009; 113 (11):2375-85.
Fujino et al., "Inhibition of myeloid differentiation by Hoxa9, Hoxb8, and Meis homeobox genes." Exp Hematol. Jul. 2001; 29(7):856-63.
Maillard & Hess, "The role of menin in hematopoiesis." Adv Exp Med Biol. 2009; 668:51-7.
Maillard et al., "Menin regulates the function of hematopoietic stem cells and lymphoid progenitors." Blood. Feb. 19, 2009; 113(8):1661-9.
Manka et a., "Inhibitors of the Menin-Mixed Lineage Leukemia (MLL) Interaction" Probe Reports from the NIH Molecular Libraries Program [Internet]. Feb. 28, 2013, http://www.ncbi.nlm.nih.gov/books/NBK133428/.
Marschalek, "Mechanisms of leukemogenesis by MLL fusion proteins" British Journal of Haematology 2011, 152 (2):141-54.
Milne et al., "Leukemogenic MLL fusion proteins bind across a broad region of the Hox a9 locus, promoting transcription and multiple histone modifications." Cancer Res. Dec. 15, 2005; 65(24):11367-74.

(Continued)

*Primary Examiner* — Celia Chang
(74) *Attorney, Agent, or Firm* — Casimir Jones SC; David Staple

(57) ABSTRACT

The present invention relates generally to compounds that inhibit the binding of menin and MLL or MLL fusion proteins and methods of use thereof. In particular embodiments, the present invention provides compositions comprising piperidine-containing compounds and methods of use thereof to inhibit the interaction of menin with MLL oncoproteins (e.g., MLL1, MLL2, MLL-fusion oncoproteins), for example, for the treatment of leukemia, solid cancers, diabetes, and other diseases dependent on activity of MLL1, MLL2, MLL fusion proteins, MLL-PTD and/or menin.

19 Claims, 12 Drawing Sheets

(56) References Cited

OTHER PUBLICATIONS

Milne et al., "MLL targets SET domain methyltransferase activity to Hox gene promoters." Mol Cell. Nov. 2002; 10 (5):1107-17.

Nguyen et al., "DOT1L, the H3K79 methyltransferase, is required for MLL-AF9-mediated leukemogenesis." Blood. Jun. 23, 2011;117(25):6912-22.

Pigazzi et al., "MLL partner genes drive distinct gene expression profiles and genomic alterations in pediatric acute myeloid leukemia: an AIEOP study." Leukemia. Mar. 2011; 25(3):560-3.

Poppe et al., "Expression analyses identify MLL as a prominent target of 11q23 amplification and support an etiologic role for MLL gain of function in myeloid malignancies." Blood. Jan. 1, 2004;103(1):229-35.

Pui et al., "Clinical heterogeneity in childhood acute lymphoblastic leukemia with 11q23 rearrangements." Leukemia. Apr. 2003;17(4):700-6.

Slany, "The molecular biology of mixed lineage leukemia." Haematologica. Jul. 2009; 94(7):984-93.

Somervaille & Cleary, "Identification and characterization of leukemia stem cells in murine MLL-AF9 acute myeloid leukemia." Cancer Cell. Oct. 2006; 10(4):257-68.

Takeda et al., "NUP98-HOXA9 induces long-term proliferation and blocks differentiation of primary human CD34+hematopoietic cells." Cancer Res. Jul. 1, 2006; 66(13):6628-37.

Tamai & Inokuchi, "11q23/MLL acute leukemia : update of clinical aspects." J Clin Exp Hematop. 2010; 50(2):91-8.

Thorsteinsdottir et al., "Overexpression of the myeloid leukemia-associated Hoxa9 gene in bone marrow cells induces stem cell expansion." Blood. Jan. 1, 2002; 99(1):121-9.

Tkachuk et al., "Involvement of a homolog of *Drosophila trithorax* by 11q23 chromosomal translocations in acute leukemias." Cell. Nov. 13, 1992; 71(4):691-700.

Tomizawa et al., "Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group." Leukemia. Nov. 2007; 21(11):2258-63.

Wong et al., "Meis1 is an essential and rate-limiting regulator of MLL leukemia stem cell potential." Genes Dev. Nov. 1, 2007; 21(21):2762-74.

Yokoyama et al. "The menin tumor suppressor protein is an essential oncogenic cofactor for MLL-associated leukemogenesis." Cell. Oct. 21, 2005;123(2):207-18.

Yokoyama et al., "Leukemia proto-oncoprotein MLL forms a SET1-like histone methyltransferase complex with menin to regulate Hox gene expression." Mol Cell Biol. Jul. 2004; 24(13):5639-49.

Yu et al., "MLL, a mammalian trithorax-group gene, functions as a transcriptional maintenance factor in morphogenesis." Proc Natl Acad Sci U S A. Sep. 1, 1998; 95(18):10632-6.

\* cited by examiner

MENIN-MLL INHIBITORS AND METHODS OF USE THEREOF

This application claims priority to U.S. Provisional Patent Application Ser. No. 61/834,178, filed Jun. 12, 2013, which is herein incorporated by reference in its entirety.

STATEMENT REGARDING FEDERALLY SPONSORED RESEARCH OR DEVELOPMENT

This invention was made with government support under R03 MH084875 awarded by the National Institutes of Health. The government has certain rights in the invention.

FIELD OF THE INVENTION

The present invention relates generally to compounds that inhibit the binding of menin and MLL and methods of use thereof. In particular embodiments, the present invention provides compositions comprising piperidine-containing compounds and methods of use thereof to inhibit the interaction of menin with MLL oncoproteins (e.g., MLL1, MLL2, MLL-fusion oncoproteins), for example, for the treatment of leukemia, solid cancers and other diseases dependent on activity of MLL1, MLL2, MLL fusion proteins and/or menin.

BACKGROUND OF THE INVENTION

Mixed lineage leukemia (MLL) presents a heterogeneous group of acute myeloid leukemia and acute lymphoblastic leukemia bearing features of more than one hematopoietic cell lineages. MLL accounts for about 80% of infant acute leukemia cases (Tomizawa, 2007; herein incorporated by reference in its entirety) and 10% of all acute leukemia cases (Marschalek, 2011; herein incorporated by reference in its entirety). Under current treatment protocols, MLL leukemia patients have a very poor prognosis with overall 5-year survival ratio stagnated around 35%, (Dimartino, 1999; Pui, 2003; Tomizawa, 2007; herein incorporated by reference in their entireties).

MLL is composited of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila trithorax* (Trx) (Tkachuk, 1992; herein incorporated by reference in its entirety). Wild type MLL binds to regulatory regions of homeox (HOX) genes (Milne, 2005; herein incorporated by reference in its entirety) through the amino terminal fragment while the catalytic C-terminal domain catalyzes the Histone 3 lysine 4 (H3K4) methylation and up regulates target genes transcription (Nakamura, 2002; Yokoyama, 2004; Milne, 2002; herein incorporated by reference in their entireties). Wild type MLL is required for maintenance HOX genes expression and is widely expressed not only during embryo development but also in adult tissues including myeloid and lymphoid cells (Butler, 1997; Yu, 1998; herein incorporated by reference in their entireties). Reciprocal translocations of MLL gene result in-frame fusion of 5'-end MLL with the 3'-end of another partner gene. Currently, more than 60 partner genes have been identified, with MLL-AF4, MLL-AF9 and MLL-ENL being the three most frequently found fusion genes (Pui, 2003; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, 2007; Yokoyama, 2005; herein incorporated by reference in their entireties). Partial tandem duplication and MLL gene amplification present a small portion of MLL leukemia cases where no partner gene is involved. However, studies revealed that these genetic changes also lead to over expression of HOX or MEIS1 genes (Dorrance, 2006; Poppe, 2004; herein incorporated by reference in their entireties).

The numerous chromosomal translocation of MLL gene and partner genes diversity add to the complexity to MLL leukemia treatment, though HOX9 and MEIS1 overexpression are commonly observed among MLL leukemia patients, each rearrangement leading to distinct deregulated target genes expression pattern and downstream events (Slany, 2009; herein incorporated by reference in its entirety). Clinical researches suggested that MLL of different chromosomal translocation are associated with different prognosis and are treated differently under current protocols (Tamai, 2010; Balgobind, 2011; Pigazzi, 2011; herein incorporated by reference in their entireties). However, both wild type MLL and MLL fusion proteins retain N terminal domain, which contains the specific menin binding motifs (MBMs). Menin is a tumor repressor protein encoded by Multiple Endocrine Neoplasia 1 (MEN1) gene. The loss function of menin is closely tied with human neoplasms in multiple endocrine organs (Chandrasekharappa, 1997; herein incorporated by reference in its entirety). Menin is also a critical leukemogenic cofactor of MLL fusion proteins. MLL fusion protein with MBMs deletion is incapable of inducing leukemic transformation in progenitor cells (Yokoyama, 2005; herein incorporated by reference in its entirety). Expression of a dominant negative peptide representing the MBM region down-regulates Meis1 expression and inhibits MLL leukemic cells proliferation (Caslini, 2007; herein incorporated by reference in its entirety). Furthermore, depletion of menin results in acute down regulation of HOXA9 expression and revives differentiation in MLL leukemic cells (Yokoyama, 2004; Yokoyama, 2005; herein incorporated by reference in their entireties). In normal hematopoiesis, steady hematopoiesis is largely preserved in menin deficient mice (Maillard, 2009; Maillard, 2009; herein incorporated by reference in their entireties), providing a therapeutic window for MLL leukemia The leukemogenic activity of MLL oncoproteins is dependent on association with menin. Therefore, selective targeting of this interaction could provide an attractive therapeutic approach to develop novel drugs for leukemias with translocations of MLL gene and other leukemias with upregulation of HOX genes.

SUMMARY OF THE INVENTION

The present invention relates generally to compounds that inhibit the binding of menin and MLL and methods of use thereof. In particular embodiments, the present invention provides compositions comprising piperdine-containing compounds and methods of use thereof to inhibit the interaction of menin with MLL and MLL oncoproteins (e.g., MLL1, MLL2, MLL-fusion oncoproteins, MLL-PTDs), for example, for the treatment of leukemia, solid cancers and other diseases dependent on activity of MLL1, MLL2, MLL fusion proteins and/or menin. In some embodiments, compositions are provided for the treatment of leukemia or other cancers, which inhibit binding of one or more MLL or MLL fusion proteins to menin.

In some embodiments, the present invention provides a one or more of compounds B1-B86 (see Table 1).

In some embodiments, the present invention provides a compound comprising the general structure of formula I:

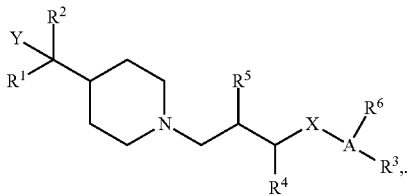

wherein Y, $R^1$, $R^2$, $R^3$, $R^4$, $R^5$, $R^6$, A, and X are independently selected from any of the substituents depicted for each position in Table 1. In such embodiments, compounds are not limited to those depicted in Table 1; rather, provided herein are compounds comprising or consisting of any combination of the substituents of the compounds of Table 1, at their respective positions. In some embodiments, compounds exhibit the characteristic of inhibiting the interaction of menin with MLL oncoproteins (e.g., MLL1, MLL2, MLL-fusion oncoproteins).

In some embodiments, the present invention provides compositions comprising a compound of formula I, wherein Y, $R^1$, $R^2$, $R^3$, $R^4$, $R^5$, $R^6$, A, and X are independently selected from any of the respective substituents described herein or depicted in Table 1, in any combination.

In some embodiments, the present invention provides compositions comprising a compound of formula I, wherein Y is independently selected from OH, $OR^7$, $NH_2$, $NHR^7$, or $NR^{7a}R^{7b}$;

wherein $R^7$ selected from $C_{1-6}$-alkyl, monohalo-$C_{1-6}$-alkyl, polyhalo-$C_{1-6}$-alkyl, ($C_{1-4}$-alkyloxy)-$C_{1-6}$-alkyl, ($C_{1-4}$-dialkylamino)-$C_{1-6}$-alkyl, $C_{1-4}$—($C_{3-6}$-cycloalkyl), $C_{1-4}$—($C_{5-6}$-heteroaryl), $C_{1-4}$—($C_{5-6}$-aryl), $C_{1-4}$—OH, $C_{1-4}$—$NH_2$, and $C_{1-4}$—CN;

wherein $R^{7a}$ and $R^{7b}$ are selected from $C_{1-6}$-alkyl, monohalo-$C_{1-6}$-alkyl, polyhalo-$C_{1-6}$-alkyl, ($C_{1-4}$-alkyloxy)-$C_{1-6}$-alkyl, ($C_{1-4}$-dialkylamino)-$C_{1-6}$-alkyl, $C_{1-4}$—($C_{3-6}$-cycloalkyl), $C_{1-4}$—($C_{5-6}$-heteroaryl), $C_{1-4}$—($C_{5-6}$-aryl), $C_{1-4}$—OH, $C_{1-4}$—$NH_2$, and $C_{1-4}$—CN, or may form a ring between $R^{7a}$ and $R^{7b}$ with $C_{3-7}$ carbons;

wherein $R^1$ is aryl or heteroaryl and substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl;

wherein $R^2$ is selected from aryl, heteroaryl, heterocycle, carbocycle containing a $C_{3-6}$ ring size, or acyclic $C_{1-6}$-alkyl; wherein $R^2$ is substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl;

wherein A is a 1,4-disubstituted aryl or heteroaryl ring substituted with X and $R^3$ and may contain a third group $R^6$ independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl;

wherein X is O, NH, or $NR^8$; wherein when X is $NR^8$, $R^8$ may be independently selected from $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl wherein $R^3$ is CN, $SO_2NH_2$, $SO_2NR^{9a}R^{9b}$, $CONR^{9a}R^{9b}$, $SO_2CH_3$, $OCF_3$, $CF_3$, Cl, $CH_3$, $CH_2CN$, $CH_2NH_2$, $CH_2NHC(O)R^{10}$, $CH_2NHSO_2R^{10}$, $NO_2$, 4-pyridyl, 3-pyridyl, C(O)R, 1,2,3-triazole, $OCH_3$; wherein $R^{9a}$ and $R^{9b}$ may be independently selected from hydrogen, $C_{1-3}$-alkyl, or polyhalo-$C_{1-3}$-alkyl, or may form a ring between $R^{9a}$ and $R^{9b}$ with $C_{3-5}$ carbons; wherein $R^{10}$ is $C_{1-3}$-alkyl; or polyhalo-$C_{1-3}$-alkyl;

wherein $R^4$ is hydrogen, or $C_{1-3}$-alkyl; and wherein $R^5$ is hydrogen, OH, or $C_{1-3}$-alkyl.

In some embodiments, one or both of $R^1$ and $R^2$ are not phenyl. In some embodiments, when Y comprises or consists of OH, one or both of $R^1$ and $R^2$ are not phenyl. In some embodiments, one or both of $R^1$ and $R^2$ are heteroaromatic (e.g., comprising 1, 2, or more O, N, S, etc. on ring structure). In some embodiments one or both of $R^1$ and $R^2$ are cycloalkanes.

In some embodiments, the piperdine ring of formula I comprises one or more substituents at the 2, 3, 5, or 6 positions. Suitable substituents include the functional groups provided herein, for example: halogen, $C_{1-3}$ alkyl, OH, alkyl-OH (e.g., $C_{1-3}$—OH, etc.), $NH_2$, alkyl-$NH_2$ (e.g., $C_{1-3}$—$NH_2$, etc.), cyano, halo (e.g., Cl, Br, F, I, etc.), polyhalo, SH, alkyl-SH (e.g., $C_{1-3}$—SH, etc.), etc.

In some embodiments, Y comprises or consists of halogen, OH, $R^7OH$, $OR^{7a}$, $R^7OR^{7a}OH$, $NH_2$, $R^7NH_2$, $R^7NHR^{7a}$, $R^7NR^{7a}R^{7b}$, $NHR^{7a}$, $NR^{7a}R^{7b}$, $R^7OR^{7a}NH_2$; wherein $R^7$, $R^{7a}$, and/or $R^{7b}$, $R^{7c}$ are independently selected from a linear alkane ($C_1$-$C_6$), branched alkane ($C_1$-$C_6$), monohalo-$C_{1-6}$-alkyl, polyhalo-$C_{1-6}$-alkyl, ($C_{1-3}$-alkyloxy)-$C_{1-6}$-alkyl, or combinations thereof.

In some embodiments, $R^1$ and $R^2$ independently comprise or consist of: an aryl (e.g., phenyl), heteroaryl group (e.g., furan, pyrrole, thiophene, imidazole, pyrazole, oxazole, thiazole, pyrazine, pyrimidine, pyridine, pyridazine, 1,2,3-triazine, 1,2,4-triazine, 1,3,5-triazine, etc.), cycloalkane (e.g., cyclopropane, cyclobutane, cyclopentane, cyclohexane, etc), $C^3$-heterocycle (e.g., aziridine, azirine, oxirane, oxirene, thiirane, thiirene, diazirine, oxaziridine, dioxirane, etc.), $C^4$-heterocycle (e.g., a azetidine, azete, oxetane, oxete, thietane, thiete, diazetidine, dioxetane, dioxete, dithietane, dithiete, etc.), $C^5$-heterocycle (e.g., pyrrolidine, tetrahydrofuran, thiolane, borolane, phospholane, arsolane, stibolane, bismolane, silolane, stannolane, imidazolidine, pyrazolidine, oxazolidine, isoxazolidine, thiazolidine, isothiazolidine, dioxolane, dithiolane, tetrazole, etc.), $C^6$-heterocycle (e.g., Piperidine, oxane, Thiane, piperazine, morpholine, thiomorpholine dioxane, dithiane, trioxane, tetrazine, etc.), and/or an acyclic (e.g., branched or straight chain) alkane. In some embodiments, an aryl, heteroaryl, cycloalkane, heterocycle, and/or acyclic alkane is substituted with 1, 2, 3, 4, 5, 6, or more substituents independently selected from one or a combination of cyano, halo (e.g., Cl, Br, F, I, etc.), OH, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl, or any other suitable substituents described herein.

In some embodiments, $R^4$ and $R^5$ independently comprise or consist of: H, $C_{1-3}$ alkyl, OH, halogen, alkyl-OH (e.g., $C_{1-3}$—OH, etc.), $NH_2$, alkyl-$NH_2$ (e.g., $C_{1-3}$—$NH_2$, etc.), cyano, halo (e.g., Cl, Br, F, I, etc.), polyhalo, SH, alkyl-SH (e.g., $C_{1-3}$—SH, etc.), etc.

In some embodiments, X is O, $R^8O$, $OR^{8a}$, $R^8OR^{8a}$, NH, $R^8NH$, $R^8NHR^{8a}$, $NHR^{8a}$, S, R—$^8S$, $SR^{8a}$, $R^8SR^{8a}$, $CH_2$, $CHR^{8a}$; wherein $R^8$ and/or $R^{8a}$ are independently selected from a linear alkane ($C_1$-$C_6$), branched alkane ($C_1$-$C_3$), monohalo-$C_{1-3}$-alkyl, polyhalo-$C_{1-3}$-alkyl, ($C_{1-3}$-alkyloxy)-$C_{1-3}$-alkyl, sulfonyl-$C_{1-3}$-alkyl, or combinations thereof.

In some embodiments, A is a 6-membered ring. In some embodiments, A is a 6-membered: aryl (e.g., 1,4-benzene), heteroaryl (pyridine, pyrazine, pyridazine, 1,2,3-triazine, 1,2,4-triazine, 1,3,5-triazine, etc.), cycloalkane (e.g., cyclohexane), etc. In some embodiments, A is a 6-membered ring comprising a substituent at the para position (e.g., 4 position) with respect to the connection point of the ring to the rest of the compound (e.g., 1 position). In some embodiments, $R^3$ is a substituent at the para position of A. In some embodiments, A further comprises substituents at ortho (e.g., 2 and/or 6 positions) and/or meta (e.g., 3 and/or 5 positions) positions. In some embodiments, $R^6$ is a substituent at the ortho and/or para positions of A. In some embodiments, 0, 1, 2, 3, or 4, $R^6$ groups are present on an A group. In some embodiments, $R^6$ groups are present or absent from any of the ortho and/or meta positions of A. In some embodiments, $R^3$ comprises or consist of CN, $SO_2NH_2$, $SO_2NR^{9a}R^{9b}$, $CONR^{9a}R^{9b}$, $SO_2CH_3$, $SO_2CF_3$, $OCF_3$, $CF_3$, Cl, $CH_3$, $CH_2CN$, $CH_2NH_2$, $CH_2OH$, $CH_2NHC(O)R^{10}$, $CH_2NHSO_2R^{10}$, $NO_2$, 4-pyridyl, 3-pyridyl, C(O)R, 1,2,3-triazole, $OCH_3$; wherein $R^{9a}$ and $R^{9b}$ may be independently selected from hydrogen, $C_{1-3}$-alkyl, or polyhalo-$C_{1-3}$-alkyl, or may form a ring between $R^{9a}$ and $R^{9b}$ with $C_{3-7}$ carbons; wherein $R^{10}$ is $C_{1-3}$-alkyl; or polyhalo-$C_{1-3}$-alkyl. In some embodiments, one or more $R^6$ groups independently comprise of consist of CN, $SO_2NH_2$, $SO_2NR^{11a}R^{11b}$, $CONR^{11a}R^{11b}$, $SO_2CH_3$, $SO_2CF_3$, $OCF_3$, $CF_3$, Cl, $CH_3$, $CH_2CN$, $CH_2NH_2$, $CH_2NHC(O)R^{12}$, $CH_2NHSO_2R^{12}$, $NO_2$, 4-pyridyl, 3-pyridyl, C(O)R, 1,2,3-triazole, $OCH_3$; wherein $R^{11a}$ and $R^{11b}$ may be independently selected from hydrogen, $C_{1-3}$-alkyl, or polyhalo-$C_{1-3}$-alkyl, or may form a ring between $R^{11a}$ and $R^{11b}$ with $C_{3-7}$ carbons; wherein $R^{12}$ is $C_{1-3}$-alkyl; or polyhalo-$C_{1-3}$-alkyl.

In some embodiments, the present invention provides methods for the treatment of a disease or condition comprising: administering a composition comprising a menin-MLL inhibitory compound to a subject suffering from said disease or condition. In some embodiments, the compounds comprise one the general structure of formula I:

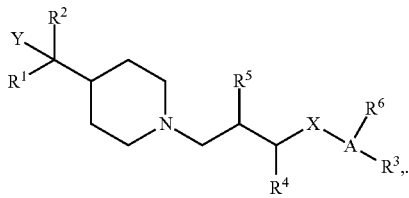

I wherein Y, $R^1$, $R^2$, $R^5$, $R^4$, X, A, $R^6$, and $R^3$ independently comprise any suitable functional groups described herein. In some embodiments, compounds comprise one of compounds B1-B86. In some embodiments, the disease or condition comprises leukemia or a solid tumor cancer (e.g., breast cancer, prostate cancer, lung cancer, liver cancer, pancreatic cancer, glioblastoma, myeloma and melanoma, etc.). In some embodiments, the leukemia comprises acute leukemias, chronic leukemias, lymphoblastic leukemias, lymphocytic leukemias, myeloid leukemias, myelogenous leukemias, Acute lymphoblastic leukemia (ALL), Chronic lymphocytic leukemia (CLL), Acute myelogenous leukemia (AML), Chronic myelogenous leukemia (CML), Hairy cell leukemia (HCL), T-cell prolymphocytic leukemia (T-PLL), Large granular lymphocytic leukemia, MLL-positive leukemias, MLL-induced leukemias, MLL-rearranged leukemias, MLL-PTD leukemias, etc.

In some embodiments, the present invention provides methods of inhibiting the interaction of MLL (e.g., MLL1 and/or MLL2 and/or MLL fusion protein) and menin comprising: (a) providing: (i) a sample comprising MLL (or MLL fusion proteins) and menin; and (ii) a composition comprising a menin-MLL inhibitor; (b) administering said composition to said sample; and (c) inhibiting the interaction between said MLL and said menin, or said MLL fusion proteins and said menin. In some embodiments, the menin-MLL binding inhibitor comprises the general structure of formula I with any suitable substituents. In some embodiments, the menin-MLL inhibitor comprises one of the compounds B1-B86.

In some embodiments, the present invention provices compositions comprising a compound having the structure of formula II:

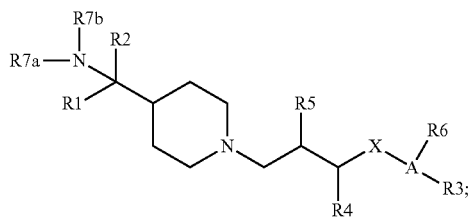

wherein $R^{7a}$ and $R^{7b}$ are independently selected from H, $C_{1-6}$-alkyl, monohalo-$C_{1-6}$-alkyl, polyhalo-$C_{1-6}$-alkyl, ($C_{1-3}$-alkyloxy)-$C_{1-6}$-alkyl, or may form a ring between $R^{7a}$ and $R^{7b}$ with $C_{3-7}$ carbons; wherein $R^1$ is aryl or heteroaryl and substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl; wherein $R^2$ is selected from heteroaryl, heterocycle, carbocycle containing a $C_{3-8}$ ring size, or acyclic $C_{1-6}$-alkyl; wherein $R^2$ is substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl; wherein A is a 1,4-disubstituted aryl or heteroaryl ring substituted with X and $R^3$ and may contain a third group $R^6$ independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, sulfonyl-$C_{1-3}$-alkyl and sulfonamide; wherein X is O, NH, or $NR^8$; wherein when X is $NR^8$, $R^8$ may be independently selected from $C_{1-3}$-alkyl, $C_{13}$-alkyloxy, monohalo-$C_{1-3}$-alkyl, polyhalo-$C_{1-3}$-alkyl, and sulfonyl-$C_{1-3}$-alkyl; wherein $R^3$ is CN, $SO_2NH_2$, $SO_2NR^{9a}R^{9b}$, $CONR^{9a}R^{9b}$, $SO_2CH_3$, $OCF_3$, $CF_3$, Cl, $CH_3$, $CH_2CN$, $CH_2NH_2$, $CH_2NHC(O)R^{10}$, $CH_2NHSO_2R^{10}$, $NO_2$, 4-pyridyl, 3-pyridyl, C(O)R, 1,2,3-triazole, $OCH_3$; wherein $R^{9a}$ and $R^{9b}$ may be independently selected from hydrogen, $C_{1-3}$-alkyl, or polyhalo-$C_{1-3}$-alkyl, or may form a ring between $R^{9a}$ and $R^{9b}$ with $C_{3-7}$ carbons; wherein $R^{10}$ is $C_{1-3}$-alkyl; or polyhalo-$C_{1-3}$-alkyl; wherein $R^4$ is hydrogen, or $C_{1-3}$-alkyl; and wherein $R^5$ is hydrogen, OH, or $C_{1-3}$-alkyl. In some embodiments, one or both of $R^1$ and $R^2$ are phenyl. In some embodiments, $R^1$ is phenyl. In some embodiments, A is a disubstituted phenyl group. In some embodiments, A is a 1,4-disubstituted phenyl group. In some embodiments, A is a phenyl group connected to the rest of the scaffold at the 1 position and comprising a substituent of 20 or fewer atoms at the 4 position. In some embodiments, the phenyl has a substituent of 10 or fewer atoms at the 4 position. In some embodiments, the substituent at the 4 position comprises a heteroaryl. In some embodiments, the substituent at the 4 position comprises 5 or fewer atoms. In some embodiments, substituent at the 4 position selected from the list consisting of CN, Cl, Br, $CF_3$, $OCF_3$. In some embodiments, $R^6$ is a halogen. In some embodiments, X is O. In some embodiments, one or both of $R^4$ and $R^5$ are H. In some embodiments, $R^4$ is H. In some embodiments, both $R^4$ and $R^5$ are H.

In some embodiments, the present invention provides methods for the treatment of a disease or condition comprising administering a composition of formula II, as described above, to a subject suffering from said disease or condition. In some embodiments, the disease or condition comprises a leukemia, solid tumor cancer, or diabetes. In some embodiments, leukemia comprises AML or ALL. In some embodiments, the present invention provides methods of inhibiting the interaction of MLL or MLL fusion protein and menin comprising administering composition of formula II, as described above, to a sample comprising MLL or MLL fusion protein and menin.

In some embodiments, the present invention provides compositions comprising a compound having the structure of formula I:

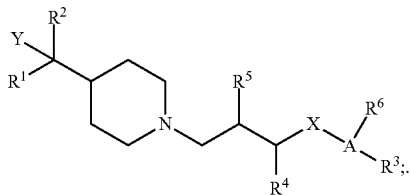

I wherein A is heteroaryl ring; wherein X is O, NH, or $NR^8$; wherein when X is $NR^8$, $R^8$ may be independently selected from $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl; wherein $R^3$ is CN, $SO_2NH_2$, $SO_2NR^{9a}R^{9b}$, $CONR^{9a}R^{9b}$, $SO_2CH_3$, $OCF_3$, $CF_3$, Cl, $CH_3$, $CH_2CN$, $CH_2NH_2$, $CH_2NHC(O)R^{16}$, $CH_2NHSO_2R^{10}$, $NO_2$, 4-pyridyl, 3-pyridyl, C(O)R, 1,2,3-triazole, $OCH_3$; wherein $R^{9a}$ and $R^{9b}$ may be independently selected from hydrogen, $C_{1-3}$-alkyl, or polyhalo-$C_{1-3}$-alkyl, or may form a ring between $R^{9a}$ and $R^{9b}$ with $C_{3-7}$ carbons; wherein $R^{10}$ is $C_{1-3}$-alkyl; or polyhalo-$C_{1-3}$-alkyl; wherein $R^6$ is selected from H, cyano, halo, hydroxyl, $C_{1-3}$-alkyl, $C_{1-3}$-alkyloxy, monohalo-$C_{1-3}$-alkyl, polyhalo-$C_{1-3}$-alkyl, sulfonyl-$C_{1-3}$-alkyl and sulfonamide; wherein Y is independently selected from OH, $OR^7$, $NH_2$, $NHR^7$, or $NR^{7a}R^{7b}$; wherein $R^7$ selected from $C_{1-6}$-alkyl, monohalo-$C_{1-6}$-alkyl, polyhalo-$C_{1-6}$-alkyl, ($C_{1-3}$-alkyloxy)-$C_{1-6}$-alkyl; wherein $R^{7a}$ and $R^{7b}$ are selected from $C_{1-6}$-alkyl, monohalo-$C_{1-6}$-alkyl, polyhalo-$C_{1-6}$-alkyl, or may form a ring between $R^{7a}$ and $R^{7b}$ with $C_{3-7}$ carbons; wherein $R^1$ is aryl or heteroaryl and substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl; wherein $R^2$ is selected from heteroaryl, heterocycle, carbocycle containing a $C_{3-8}$ ring size, or acyclic $C_{1-6}$-alkyl; wherein $R^2$ is substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl; wherein $R^4$ is hydrogen, or $C_{1-3}$-alkyl; and wherein $R^5$ is hydrogen, OH, or $C_{1-3}$-alkyl. In some embodiments, one or both of $R^1$ and $R^2$ are phenyl. In some embodiments, $R^1$ is phenyl. In some embodiments, Y is OH. In some embodiments, A is a pyridine. In some embodiments, A is connected to X at its 3 position and $R^3$ at is 6 position. In some embodiments, $R^6$ is a halogen. In some embodiments, X is O. In some embodiments, one or both of $R^4$ and $R^5$ are H. In some embodiments, $R^4$ is H. In some embodiments, both $R^4$ and $R^5$ are H. In some embodiments, the compound is selected from compounds B37, B61, and B64.

In some embodiments, the present invention provides methods for the treatment of a disease or condition comprising administering a composition of formula I, as described in the preceding paragraph, to a subject suffering from said disease or condition. In some embodiments, the disease or condition comprises a leukemia, solid tumor cancer, or diabetes. In some embodiments, leukemia comprises AML or ALL. In some embodiments, the present invention provides methods of inhibiting the interaction of MLL or MLL fusion protein and menin comprising administering composition of formula II, as described in the preceding paragraph, to a sample comprising MLL or MLL fusion protein and menin.

Suitable compositions may comprise combination of any of the compounds described herein with one another or with other compounds of interest. Stereoisomers, salts, and derivates of the compounds are further contemplated.

In some embodiments, the present invention provides a method comprising administering a composition for the treatment of leukemia (e.g., which inhibits binding of one or more MLL fusion proteins to menin or MLL wild type to menin) to a subject suffering from leukemia. In some embodiments, the leukemia comprises AML or ALL. In some embodiments, the composition comprises a menin-MLL inhibitor. In some embodiments, the composition comprises a compound of the general structure of formula I or formula II. In some embodiments, the composition comprises one of compounds B1-B86, a compound comprising formula I with a rearrangement of the substituents of compound B1-B86, a compound comprising formula I comprising any suitable substituents described herein, and/or derivatives thereof In some embodiments, the present invention provides a method of screening compounds effective in treating leukemia comprising assaying one or more compounds for inhibition of the interaction between MLL and menin and/or MLL fusion proteins and menin. In some embodiments, the screening is performed in vitro. In some embodiments, the screening is performed in vivo. In some embodiments, the assaying comprises a fluorescence polarization assay. In some embodiments, the assaying comprises a time-resolved fluorescence resonance energy transfer assay. In some embodiments, the assaying comprises nuclear magnetic resonance (NMR) methods. In some embodiments, the assaying comprises cellular assays and/or animal (e.g., mice) studies.

In some embodiments, the present invention provides a method of inhibiting the interaction of MLL and menin and/or MLL fusion protein and menin comprising: (a) providing: (i) a sample comprising MLL and/or MLL fusion protein and menin and (ii) a composition configured to inhibit the interaction of MLL and/or MLL fusion protein and menin, (b) administering the composition to the sample, (c) contacting MLL or MLL fusion protein and/or menin with the composition, and (d) inhibiting the interaction between MLL and menin, and between MLL fusion proteins and menin. In some embodiments, the sample comprises cells from a subject suffering from leukemia. In some embodiments, the subject is a human subject or a human patient. In some embodiments, the cells are within a subject suffering from leukemia. In some embodiments, the composition comprises a compound of formula I or formula II with suitable substituents as provided herein. In some embodiments, the present invention comprises any structural derivatives of compounds B1-B86.

In some embodiments, the present invention provides methods comprising the use of a composition and/or compound described herein (e.g., a derivative of one of formula I, a derivative of formula II, one of compounds B1-B86, a rearrangement of 2 or more of compounds B1-B86, etc.). In some embodiments, the present invention provides methods comprising the use of a composition and/or compound described herein for the treatment of leukemia or other cancer.

In some embodiments, the present invention provides compositions comprising a compound of formula I:

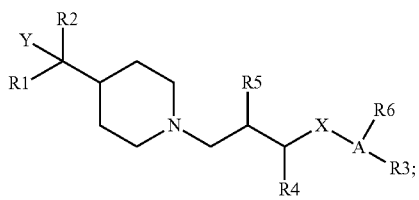

wherein R1-R6, A, Y, and X are independently selected from the substituents and functional groups provided herein, but one or more of the following limitations apply: $R^1$ or $R^2$ is a heterocycle, A is a heterocycle, Y is $OR^7$ and $R^7$ does not equal H, or Y is $NH_2$, $NHR^7a$, or $NR^7aR^7b$. In some embodiments in which Y is $OR^7$ (and $R^7$ does not equal H), $NHR^7a$, and/or $NR^7aR^7b$, $R^7$ (or $R7^a$ or $R7^b$) is selected from $C_{1-6}$-alkyl, monohalo-$C_{1-6}$-alkyl, polyhalo-$C_{1-6}$-alkyl, ($C_{1-3}$-alkyloxy)-$C_{1-6}$-alkyl), $C_{1-3}$-amino, $C_{1-3}$-dialkylamino (e.g., $C_{13}$-dimethylamino), $C_{1-3}$-cycloalkyl$_{3-6}$, saturated or unsaturated alkyl and/or cycloalcyl chains and/or rings, OH, $C_{1-6}$—OH, amino (e.g., $NH_2$, $NHC_{1-6}$, $NC_{1-6}C_{1-6}$), $C_{1-6}$-amino (e.g., (e.g., $C_{1-6}$—$NH_2$, $C_{1-6}$—$NHC_{1-6}$, $C_{1-6}$—$NC_{1-6}C_{1-6}$), or $C_{1-6}$—CN. In some embodiments in which $R^1$, $R^2$, and/or A is a heterocycle, the heterocycle is a pyridine. In some embodiments in which $R^1$, $R^2$, and/or A is a heterocycle, a heterocycle is selected from any suitable heterocycles described herein and/or known in the art. In some embodiments, the compound is selected from compounds B54, B55, B56, B57, B58, B60, B62, B64, B67, B69, B71, B72, B73, B74, and B75. In some embodiments, the compound comprises any suitable rearrangement of the substituents of compounds B54, B55, B56, B57, B58, B60, B62, B64, B67, B69, B71, B72, B73, B74, and B75 (e.g., wherein $R^1$ or $R^2$ is a heterocycle, A is a heterocycle, Y is $OR^7$ and $R^7$ does not equal H, and/or Y is $NH_2$, $NHR^7a$, or $NR^7aR^7b$). In some embodiments, a composition comprises a compound of formula I, wherein Y is not H or OH. In some embodiments, a composition comprises a compound of formula I, wherein A is not phenyl.

DEFINITIONS

Figure 1:
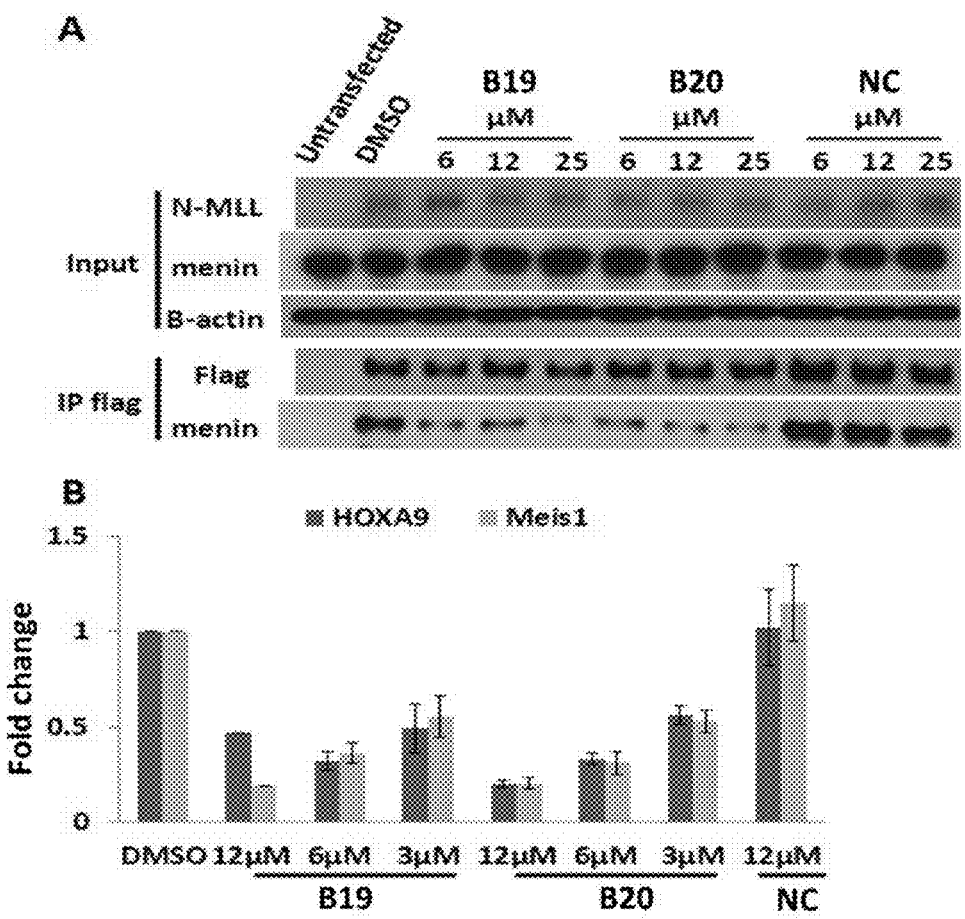
FIG. 1. Cellular activity of menin-MLL inhibitors. A. B19 and B20 but not NC inhibit the menin interaction with MLL-AF9 in HEK293 cells transfected with Flag-MLL-AF9. B. Treatment with B19 and B20 strongly downregulates the expression level of Hoxa9 and Meis1 in MLL-AF9 transformed bone marrow cells.
Figure 2:
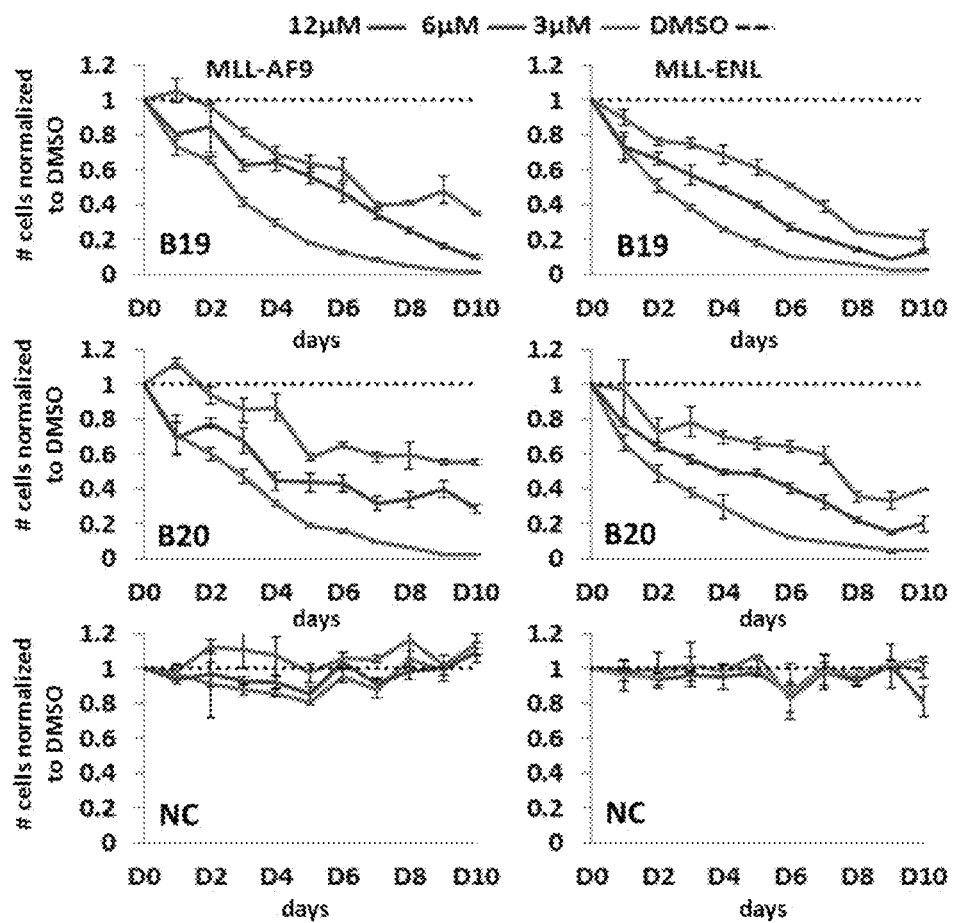
FIG. 2. B19 and B20 inhibit proliferation of MLL-AF9 and MLL-ENL transformed murine bone marrow cells. No such effect is observed for the negative control compound NC.
Figure 3:
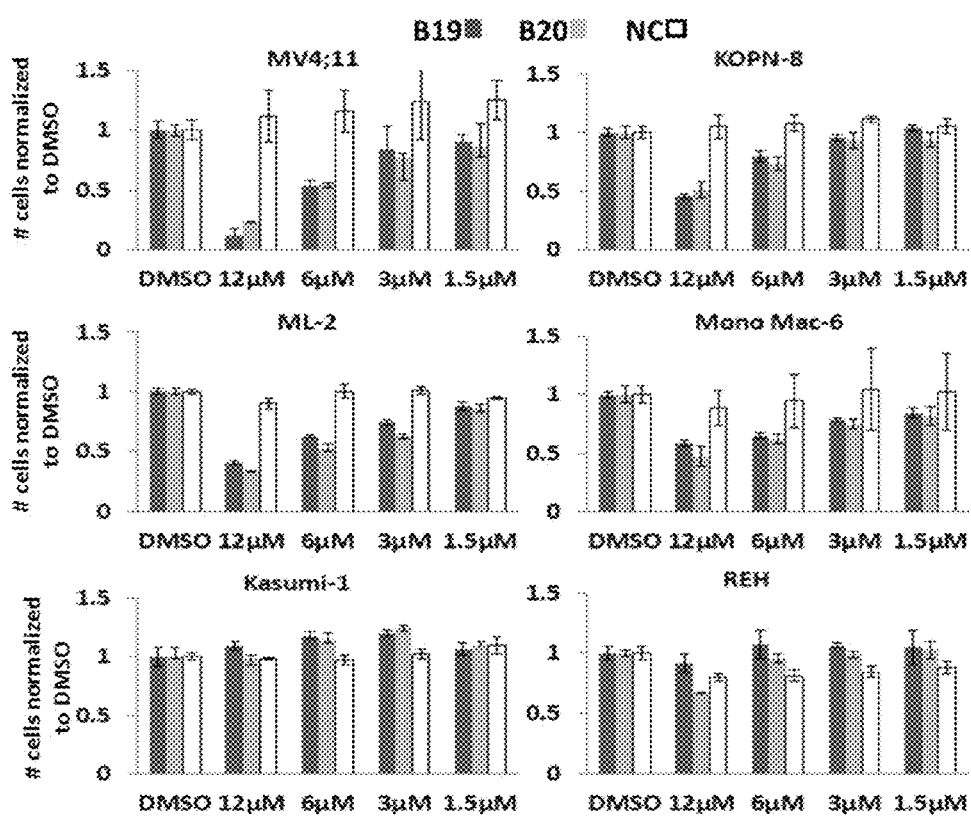
FIG. 3. B19 and B20 but not NC inhibit proliferation of human MLL leukemia cells: MV4;11, KOPN8, ML-2, MonoMac6. No effect was observed for the treatment of non-MLL leukemia cells (Kasumi-1 and REH) upon treatment with these menin-MLL inhibitors.
Figure 4:
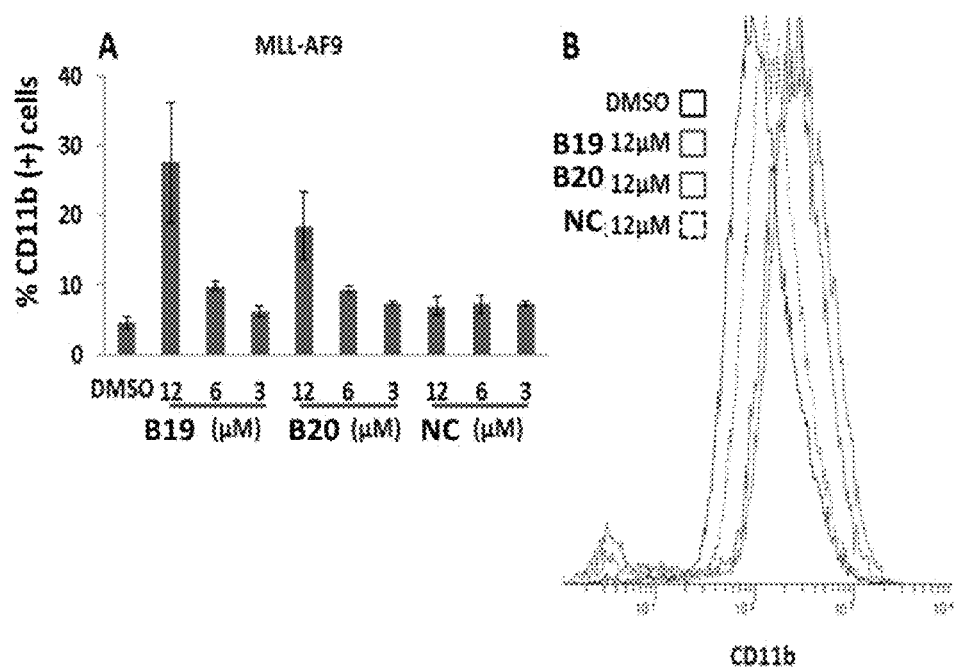
FIG. 4. A, B. Treatment with B19 and B20 menin-MLL inhibitors induces differentiation of the MLL-AF9 transformed murine bone marrow cells as assessed by increased expression of the CD11b differentiation marker.
Figure 5:
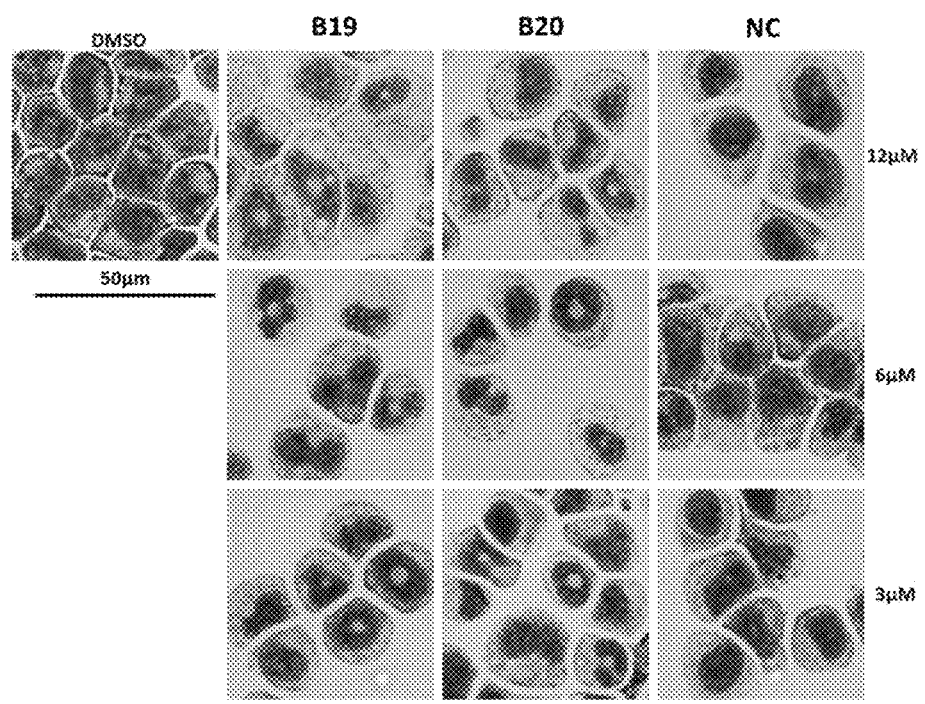
FIG. 5. Treatment with B19 and B20 menin-MLL inhibitors induces differentiation of the MLL-AF9 transformed murine bone marrow cells as assessed by significant change in morphology of these cells.
Figure 6:
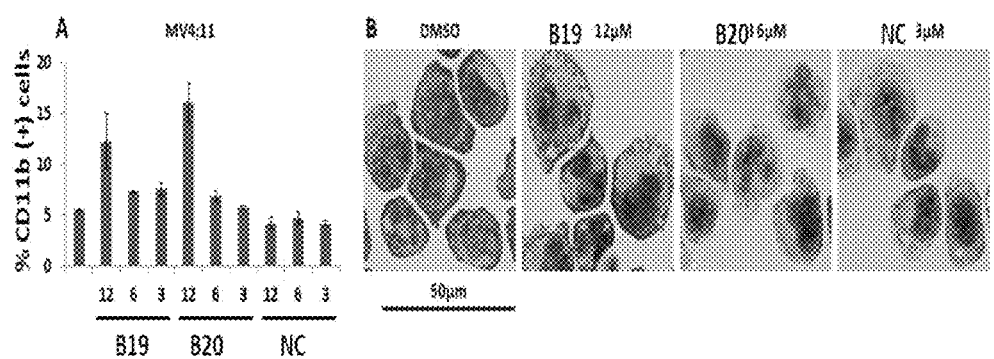
FIG. 6. Treatment with B19 and B20 induces differentiation of human MLL leukemia cell lines: MV4;11 as reflected by increased expression level of CD11b (A) and morphology change of these cells (B).
Figure 7:
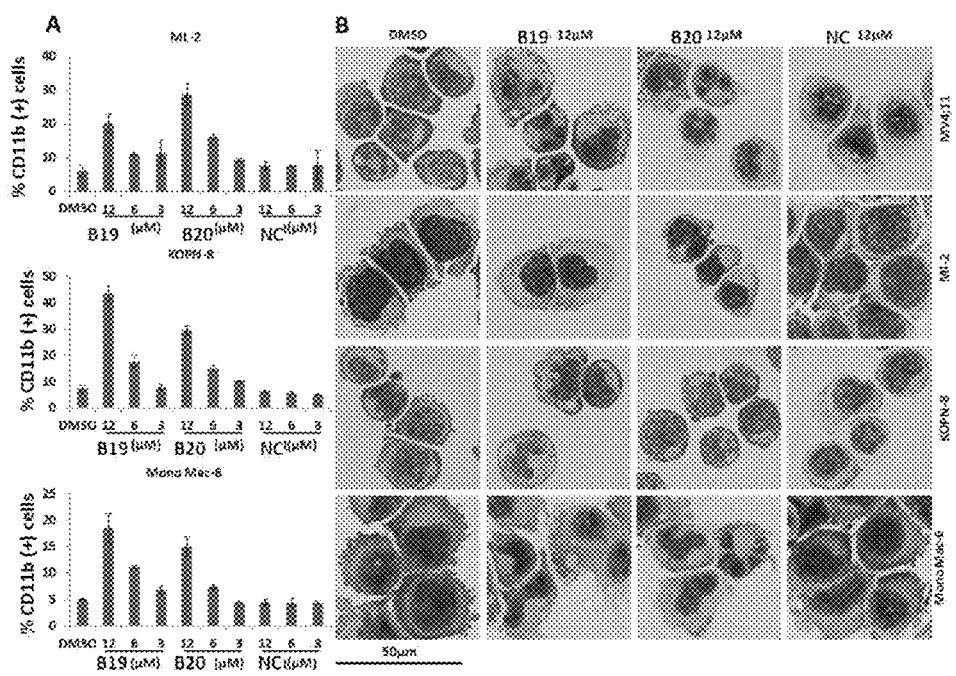
FIG. 7. B19 and B20 induce differentiation in a panel of human MLL leukemia cell lines with different MLL translocations: MV4;11, MI-2, KOPN8 and MonoMac-6 as assessed by change in the CD11b expression (A) and change in morphology of cells (B).
Figure 8:
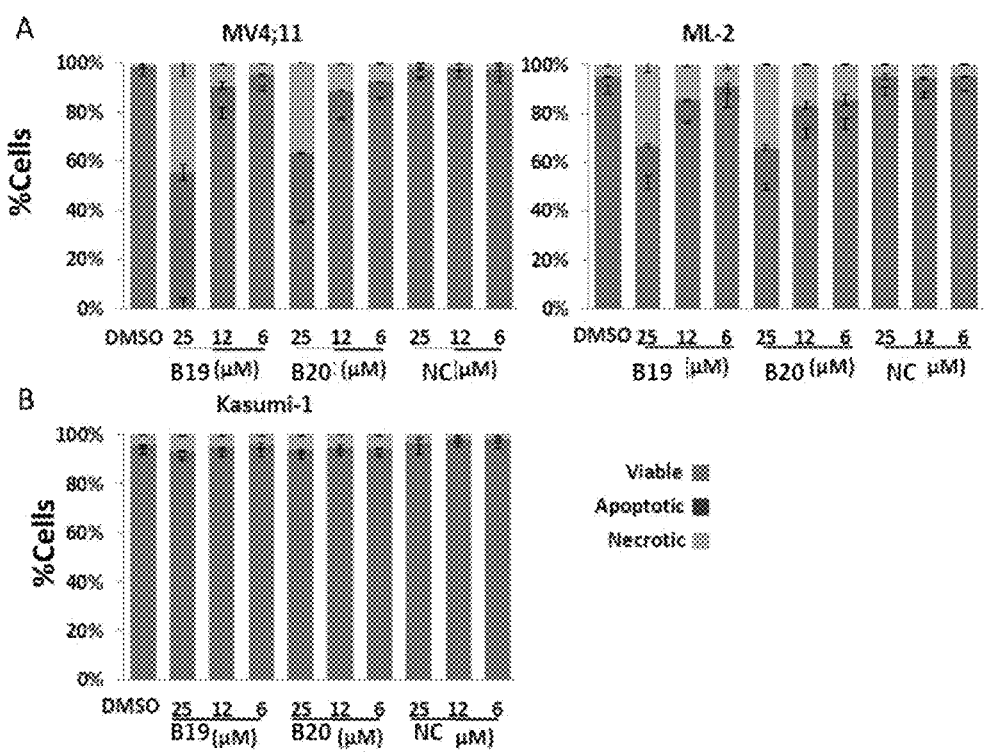
FIG. 8. A. B19 and B20 but not the control compound (NC) induce apoptosis in human MLL leukemia cell lines with different MLL translocations (MV4;11 and ML-2). B. No effect on apoptosis was observed in the control cell line (Kasumi-1) without MLL translocation upon treatment with B19, B20 or NC.
Figure 9:
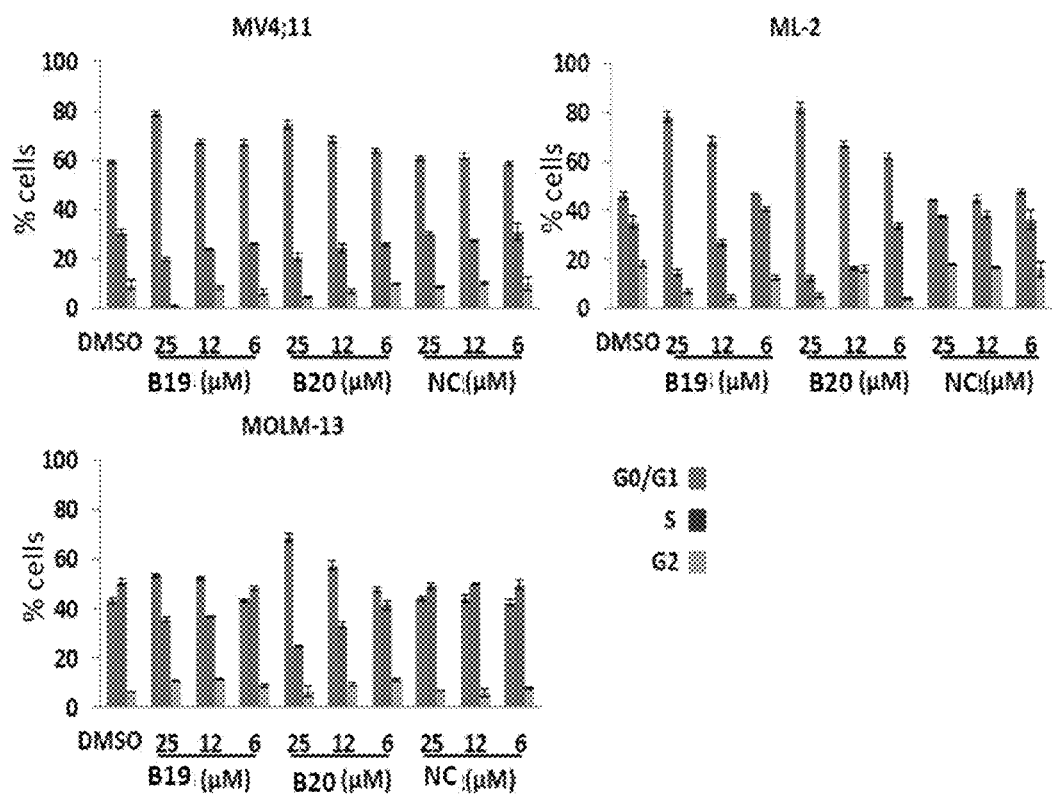
FIG. 9. B19 and B20 induce cell cycle arrest in different MLL leukemia cells. No such effect was observed for NC compound.
Figure 10:
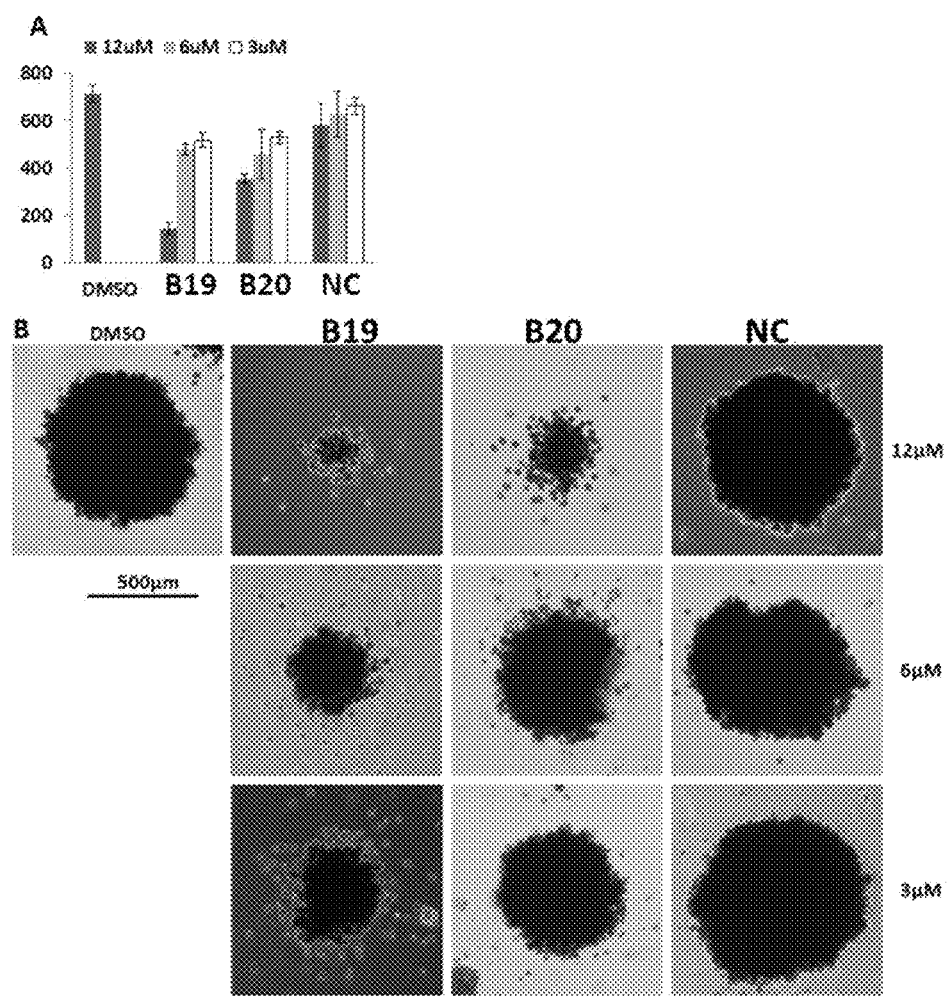
FIG. 10. B19 and B20 but not NC reduce transforming properties of MLL-AF9 fusion protein as reflected by decreased colony number in the colony forming assay (A) and change in morphology of colonies (B) in MLL-AF9 transformed murine bone marrow cells upon treatment with these compounds.
Figure 11:
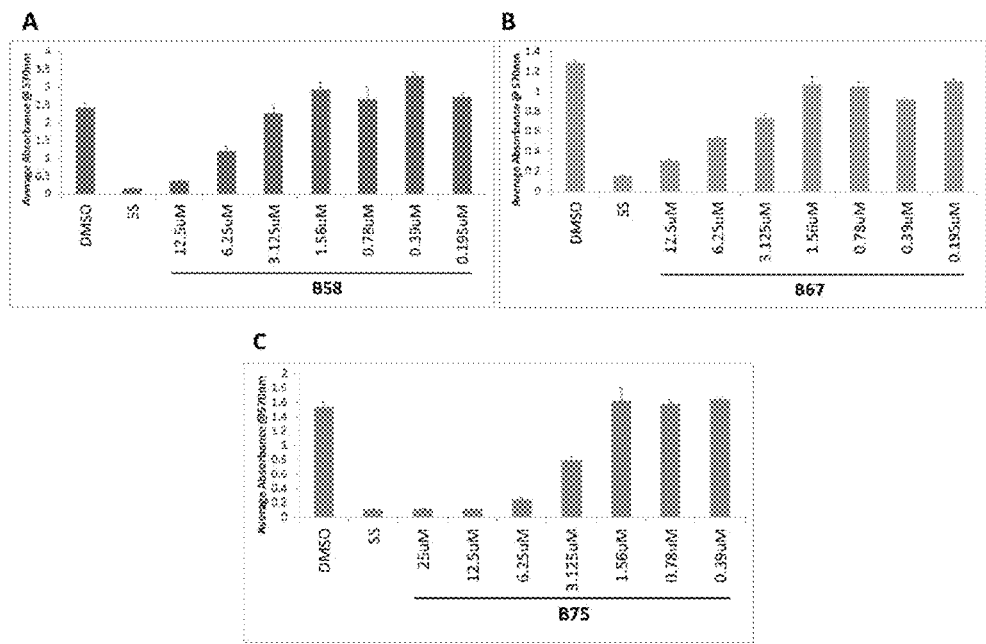
FIG. 11. MTT cell viability assay in MLL-AF9 transformed murine bone marrow cells revealing inhibition of cell proliferation induced by: A) B58, B) B67, C) B75 after 7 days of treatment with these compounds.
Figure 12:
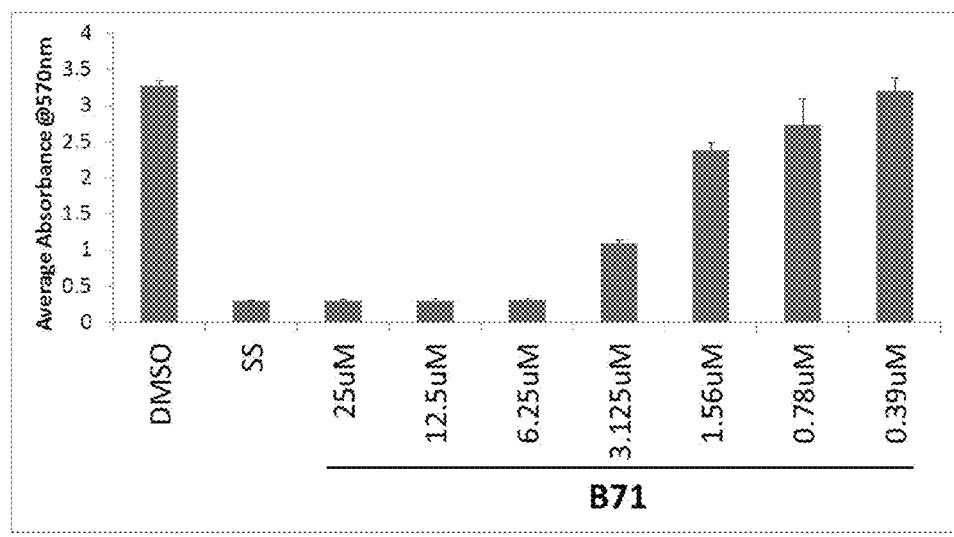
FIG. 12. MTT cell viability assay in MLL-AF9 transformed murine bone marrow cells revealing inhibition of cell proliferation induced by B71 after 7 days of treatment with this compound.

The term "system" refers a group of objects, compounds, methods, and/or devices that form a network for performing a desired objective.

As used herein a "sample" refers to anything capable of being subjected to the compositions and methods provided herein. The sample may be in vitro or in vivo. In some embodiments, samples are "mixture" samples, which samples from more than one subject or individual. In some embodiments, the methods provided herein comprise purifying or isolating the sample. In some embodiments, the sample is purified or unpurified protein. In some embodiments, a sample may be from a clinical or research setting. In some embodiments, a sample may comprise cells, fluids (e.g. blood, urine, cytoplasm, etc.), tissues, organs, lysed cells, whole organisms, etc. In some embodiments, a sample may be derived from a subject. In some embodiments, a sample may comprise one or more partial or whole subjects.

As used herein, the term "subject" refers to any animal including, but not limited to, humans, non-human primates, bovines, equines, felines, canines, pigs, rodents (e.g., mice), and the like. The terms "subject" and "patient" may be used interchangeably, wherein the term "patient" generally refers to a human subject seeking or receiving treatment or preventative measures from a clinician or health care provider.

As used herein, the terms "subject at risk for cancer" or "subject at risk for leukemia" refer to a subject with one or more risk factors for developing cancer and/or leukemia. Risk factors include, but are not limited to, gender, age, genetic predisposition, environmental exposure, and previous incidents of cancer, preexisting non-cancer diseases, and lifestyle.

As used herein, the terms "characterizing cancer in subject" "characterizing leukemia in subject" refers to the identification of one or more properties of a cancer and/or leukemia sample in a subject, including but not limited to, the presence of benign, pre-cancerous or cancerous tissue or cells and the stage of the cancer (e.g., leukemia). Cancers (e.g., leukemia) may be characterized by identifying cancer cells with the compositions and methods of the present invention.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "effective amount" refers to the amount of a compound (e.g., a compound having a structure presented above or elsewhere described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., a compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions characterized by viral infection (e.g., providing dosing, route of administration, decision trees for treating physicians for correlating patient-specific characteristics with therapeutic courses of action). The compounds of the present invention (e.g. as shown in structures above and elsewhere presented herein) can be packaged into a kit, which may include instructions for administering the compounds to a subject.

As used herein, the term "alkyl", unless defined more specifically herein, refers to a moiety consisting of carbon and hydrogen containing no double or triple bonds. An alkyl may be linear, branched, cyclic, or a combination thereof, and may contain from one to fifty carbon atoms. Examples of alkyl groups include but are not limited to methyl, ethyl, propyl, isopropyl, cyclopropyl, butyl isomers (e.g. n-butyl, iso-butyl, tert-butyl, etc.) cyclobutyl isomers (e.g. cyclobutyl, methylcyclopropyl, etc.), pentyl isomers, cyclopentane isomers, hexyl isomers, cyclohexane isomers, and the like. Unless specified otherwise (e.g., substituted alkyl group, heteroalkyl, alkoxy group, haloalkyl, alkylamine, thioalkyl, etc.), an alkyl group contains carbon and hydrogen atoms only.

As used herein, the term "linear alkyl", unless defined more specifically herein, refers to a chain of carbon and hydrogen atoms (e.g., ethane, propane, butane, pentane, hexane, etc.). A linear alkyl group may be referred to by the designation —$(CH_2)_q CH_3$, where q is 0-49. The designation "$C_{1-12}$ alkyl" or a similar designation, refers to alkyl having from 1 to 12 carbon atoms such as methyl, ethyl, propyl isomers (e.g. n-propyl, isopropyl, etc.), butyl isomers, cyclobutyl isomers (e.g. cyclobutyl, methylcyclopropyl, etc.), pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. Similar designations refer to alkyl with a number of carbon atoms in a different range.

As used herein, the term "branched alkyl", unless defined more specifically herein, refers to a chain of carbon and hydrogen atoms, without double or triple bonds, that contains a fork, branch, and/or split in the chain (e.g., 3,5-dimethyl-2-ethylhexane, 2-methyl-pentane, 1-methyl-cyclobutane, ortho-diethyl-cyclohexane, etc.). "Branching" refers to the divergence of a carbon chain, whereas "substitution" refers to the presence of non-carbon/non-hydrogen atoms in a moiety. Unless specified otherwise (e.g., substituted branched alkyl group, branched heteroalkyl, branched alkoxy group, branched haloalkyl, branched alkylamine, branched thio-alkyl, etc.), a branched alkyl group contains carbon and hydrogen atoms only.

As used herein, the term "cycloalkyl", unless defined more specifically herein, refers to a completely saturated mono- or multi-cyclic hydrocarbon ring system. When composed of two or more rings, the rings may be joined together in a fused, bridged or spiro-connected fashion. Cycloalkyl groups of the present application may range from three to ten carbons ($C_3$ to $C_{10}$). A cycloalkyl group may be unsubstituted, substituted, branched, and/or unbranched. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. Unless specified otherwise (e.g., substituted cycloalkyl group, heterocyclyl, cycloalkoxy group, halocycloalkyl, cycloalkylamine, thiocycloalkyl, etc.), an alkyl group contains carbon and hydrogen atoms only.

As used herein, the term "heteroalkyl", unless defined more specifically herein, refers to an alkyl group, as defined herein, wherein one or more carbon atoms are independently replaced by one or more heteroatoms (e.g., oxygen, sulfur, nitrogen, phosphorus, silicon, or combinations thereof). The alkyl group containing the non-carbon substitution(s) may be a linear alkyl, branched alkyl, cycloalkyl (e.g., cycloheteroalkyl), or combinations thereof. Non-carbons may be at terminal locations (e.g., 2-hexanol) or integral to an alkyl group (e.g., diethyl ether).

As used herein, the term "substituted", unless defined more specifically herein, (e.g., substituted alyklene) means that the referenced group (e.g., alkyl, aryl, etc.) comprises a substituent group (e.g., carbon/hydrogen-only substituent, hetero-substituent, halosubstituent, etc.). The term "optionally substituted", as used herein, means that the referenced group (e.g., alkyl, cycloalkyl, etc.) may or may not be substituted with one or more additional group(s). Substituent groups may be selected from, but are not limited to: alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of substituents include, halo, —CN, —OR, —C(O)R, —OC(O)R, —C(O)OR, OC(O)NHR, —C(O)N(R)$_2$, —SR—, —S(═O)R, —S(═O)$_2$R, —NHR, —N(R)$_2$, —NHC(O)—, NHC(O)O—, —C(O)NH—, S(═O)$_2$NHR, —S(O)$_2$N(R)$_2$, —NHS(═O)$_2$, —NHS(O)$_2$R, $C^1$-$C^6$alkyl, $C^1$-$C^6$alkoxy, aryl, heteroaryl, cycloalkyl, heterocycloalkyl, halo-substituted $C^1$-$C^6$alkyl, halo-substituted $C^1$-$C^6$alkoxy, where each R is independently selected from H, halo, $C^1$-$C^6$alkyl, $C^1$-$C^6$alkoxy, aryl, heteroaryl, cycloalkyl, heterocycloalkyl, halo-substituted $C^1$-$C^6$alkyl, halo-substituted $C^1$-$C^6$alkoxy.

As used herein, the term "substituted alkyl", unless defined more specifically herein, refers to an alkyl group, as defined herein, displaying one or more non-carbon-atom-containing moieties (e.g., a group containing non-carbon atoms, possibly in addition to carbon atoms). The non-carbon-atom-containing moieties atoms may comprise: oxygen, sulfur, nitrogen, phosphorus, silicon, halogens (e.g. chlorine, bromine, flourine, iodine, etc.), or combinations thereof). The non-carbon-atom-containing moieties may also comprise carbon and hydrogen. The alkyl group containing the non-carbon substitution(s) may be a linear alkyl, branched alkyl, cycloalkyl (e.g., cycloheteroalkyl), or combinations thereof. Examples of substituted alky groups include: 2-hexanol, diethyl ether (also a heteroalkyl), 1-chloro-propane, etc.

As used herein, the terms "heteroaryl" or "heteroaromatic", unless defined more specifically herein, refer to monocyclic, bicyclic, tricyclic, and other multicyclic ring systems (e.g., having four or greater ring members), wherein at least one ring in the system is aromatic, at least one ring in the system contains one or more heteroatoms selected from nitrogen, oxygen and sulfur, and wherein each ring in the system contains 3 to 7 ring members. Unless otherwise defined herein, suitable substituents on the unsaturated carbon atom of a heteroaryl group are generally selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(═NH)—N(R)$_2$, —P(O)$_2$R, —PO(R)$_2$, —OPO(R)$_2$, —(CH$_2$)O$_2$NHC(O)R, phenyl (Ph) optionally substituted with R, —O(Ph) optionally substituted with R, —(CH$_2$)1-2(Ph), optionally substituted with R, or —CH═CH(Ph), optionally substituted with R, wherein each independent occurrence of R is selected from hydrogen, optionally substituted $C^1$-$C^6$alkyl, optionally substituted $C^1$-$C^6$alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl. Any substituents depicted in structures or examples herein, should be viewed as suitable substituents for use in embodiments of the present invention.

As used herein, the terms "heterocycloalkyl" of "heterocycle", unless defined more specifically herein, refer to a cycloalkyl, as defined herein, wherein one or more of the ring carbons are replaced by a moiety selected from —O—, —N═, —NR—, —C(O)—, —S—, —S(O)— or —S(O)$_2$—, wherein R is hydrogen, $C^1$-$C^8$alkyl or a nitrogen protecting group, with the proviso that the ring of said group does not contain two adjacent O or S atoms. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

DETAILED DESCRIPTION

The present invention relates generally to compounds that inhibit the binding of menin and MLL and/or menin and MLL fusion proteins and methods of use thereof. In particular embodiments, the present invention provides compositions comprising piperdine-containing compounds and methods of use thereof to inhibit the interaction of menin with MLL and MLL fusion oncoproteins (e.g., MLL1, MLL2, MLL-fusion oncoproteins), for example, for the treatment of leukemia, solid cancers and other diseases dependent on activity of MLL1, MLL2, MLL fusion proteins and/or menin. Embodiments of the present invention directed towad the treatment and/or prevention of leukemia or recurrence thereof are described herein; however, it should be understood that the compositions and methods described herein are not limited to the leukemia application. Rather, in some embodiments, the compositions and methods described herein should be understood to also be useful for the treatment and/or prevention of other cancers, including but not limited to breast, pancreastic, prostate and colon cancers, glioblastoma, myeloma, diabetes etc. The compounds provided herein are not limited to therapeutic uses; any additional uses for this class of compounds are also contemplated.

Experiments were conducted during development of embodiments of the present invention to develop a class of compounds for the inhibition of the menin-MLL interaction, and for treatment of MLL leukemias, other cancers, and other diseases and conditions. High Throughput Screening was performed at the NIH MLPCN (Molecular Libraries Probe Production Centers Network) to identify additional lead compounds that target menin and inhibit the menin-MLL interaction. A collection of about 300,000 compounds was screened using a fluorescence polarization assay with a fluorescein-labeled MLL-derived peptide comprising the high affinity menin binding motif (MBM1) (Grembecka et al, 2010; herein incorporated by reference in its entirety). A stepwise procedure, including two fluorescence polarization assays with fluorescein- and Texas Red-labeled MBM1 for primary screening, followed by HTRF (Homogenous Time Resolved Fluorescence) assay for secondary screening and NMR experiments to validate direct binding of compounds to menin, was applied to identify menin-MLL inhibitors. One of the most potent compounds identified by HTS at MLPCN was B2, with a half maximal inhibitory concentration ($IC_{50}$) value of 14 µM for inhibition of the menin-MLL interaction.

Experiments were conducted during development of embodiments of the present invention to develop analogues of B2. It was determined that removal of the hydroxyl group from the aliphatic chain did not affect the activity, as B1 that is missing this functional group has almost the same activity as the parent compound ($IC_{50}$=18 µM, Example 9). For ease of synthesis, this group was absent in subsequent compounds. Replacement of one of the phenyl groups in B1 with a cyclopenthyl substituent resulted in more than 10-fold improvement in $IC_{50}$ value for B11 ($IC_{50}$=883 nM, Example 9). B11 is a racemic mixture of two enantiomers, which was then separated by HPLC and activity of the enantiomers was tested individually. Remarkably, both isomers demonstrated similar, submicromolar activity for inhibition of the menin-MLL interaction ($IC_{50}$=336 nM and 412 nM, for B19 and B20, respectively, Example 9). The lack of a very significant difference in the activity of these compounds indicates that both phenyl and cyclophenthyl are relatively well tolerated by the binding pockets on menin where these substituents bind. A compound missing the cyclopenthyl ring B76 (NC) was also synthesized, and is about 3 orders of magnitude weaker than the most potent compound ($IC_{50}$=250 µM), serving as a negative control compound in cellular experiments.

Similar experiments to the above were performed to investigate the importance of other positions on the B19 and related structures. Through such experiments, very potent inhibitors of the menin-MLL interaction were developed (see Example 9).

In some embodiments, compounds of the present invention comprise a general formula of formula I:

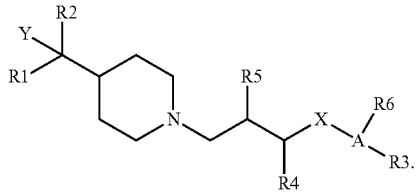

In some embodiments, substituents Y, X, A, and $R^1$-$R^6$ are independently selected from functional groups that comprise or consist of a combination of the following moieties:

Single atoms: H, Cl, Br, F, or I;

Alkanes (alkyl groups): methane (methyl), ethane (ethyl), propane (propyl), butane (butyl), pentane (pentyl), hexane (hexyl), or any suitable straight chain or branched $C^1$-$C^{20}$ alkane;

Alkenes: methene, ethene, propene, butene, pentene, hexene, or any suitable $C^7$-$C^{20}$ alkene;

Alkynes: methyne, ethyne, propyne, butyne, pentyne, hexyne, or any suitable $C^7$-$C^{20}$ alkyne;

Cycloalkanes: cyclopropane, cyclobutane, cyclopentane, cyclohexane, or any suitable $C^7$-$C^{20}$ cycloalkane;

Aromatic rings (e.g., carbon-only or heteroaromatics (e.g., heteroaryl)): furan, benzofuran, isobenzofuran, pyrrole, indole, isoindole, thiophene, benzothiophene, benzo[c] thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, triazine (e.g., 1,2,3-triazine; 1,2,4-triazine; 1,3,5 triazine), thiadiazole, etc.;

Haloalkanes: halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) an halogens (e.g., Cl, Br, F, I, etc.);

Alcohols: OH, methanol, ethanol, propanol, butanol, pentanol, hexanol, cyclic alcohols (e.g., cyclohexanol), aromatic alcohols (e.g., phenol), or any other suitable combination of an OH moiety with a second moiety;

Ketones: methyl methyl ketone (acetone), methyl ethyl ketone (butanone), propyl ethyl ketone (pentanone), or any other suitable combination of alkyl chains with =O;

Carboxylates: methanoate, ethanoate, propanote, butanoate, pentanoate, hexanoate, or any other suitable combination of alkyl chain with OO⁻;

Carboxylic acids: methanoic acid, ethanoic acid, propanoic acid, butanoic acid, pentanoic acid, hexanoic acid, or any other suitable combination of alkyl chain with OOH;

Ethers: methoxy, ethoxy, methylmethoxy, ethylmethoxy, or any other suitable combination of alkyl chains surrounding an O;

Amides: methanamide ($CONH_2$), ethanamide ($CH_2CONH_2$), propanamide (($CH_2)_2CONH_2$), alkan″amide (($CH_2)_nCONH_2$), n-methyl alkan″amide (($CH_2)_nCONHCH_3$), c-methyl alkan″amide (($CH_2)_nNHCOCH_3$), n-alkyl alkan″amide (($CH_2)_nCONH(CH_2)_mCH_3$), c-methyl alkan″amide (($CH_2)_nNHCO(CH_2)_mCH_3$), etc.;

Primary amines: $NH_2$, methylamine, ethylamine, cyclopropylamine, etc.;

Secondary amines: aminomethyl ($NHCH_3$), aminoethyl ($NHCH_2CH_3$), methyl-aminomethyl ($CH_2NHCH_3$; aka methylamine-methane), alkyl″-aminomethane (($CH_2)_n NHCH_3$), etc.;

Tertiary amines: dimethylamine ($N(CH_3)_2$), dimethylamine ($N(CH_3)_2$), methyl-ethyl-amine ($NCH_3CH_2CH_3$), methane-diethylamine ($CH_2N(CH_2CH_3)_2$; aka methylamine-diethane), etc.;

Cyanos: methyl carbonitrile ($CH_2CN$), ethyl carbonitrile (($CH_2)_2CN$), alkyl″ carbonitrile (($CH_2)_nCN$), etc.

Thiols: methanethiol ($CH_2SH$), ethanethiol (($CH_2)_2SH$), alkan″ethiol (($CH_2)_nSH$), etc.

Sulfides: dimethyl sulfide ($CH_2SCH_3$), methyl-ethyl sulfide ($CH_2SCH_2CH_3$), alkyl″-alkyl‴ sulfide (($CH_2)_nS(CH_2)_{m-1}CH_3$), etc.;

Sulfoxides: dimethyl sulfoxide ($CH_2SOCH_3$), methyl-ethyl sulfoxide ($CH_2SOCH_2CH_3$), alkyl″-alkyl‴ sulfoxide (($CH_2)_nSO(CH_2)_{m-1}CH_3$), etc.;

Sulfone: dimethyl sulfone ($CH_2SO_2CH_3$; aka methyl-sulfone-methyl), methyl-ethyl sulfone ($CH_2SO_2CH_2CH_3$; aka methyl-sulfone-ethyl), alkyl″-alkyl‴ sulfone (($CH_2)_n SO_2 (CH_2)_{m-1}CH_3$; aka alkyl″-sulfone-alkyl‴), $R^xSO_2R^y$ (wherein Rx and Ry are independently selected from any of the moieties provided in this list or combinations thereof), etc.;

Sulfuric acids: $SO_2H$, methyl sulfinic acid ($CH_2SO_2H$), ethyl sulfinic acid (($CH_2)_2SO_2H$), alkyl″ sulfinic acid (($CH_2)_n SO_2H$), etc.;

Phosphates: $OP(=O)(OH)_2$, methyl phosphate ($CH_2OP(=O)(OH)_2$), ethyl phosphate (($CH_2)_2OP(=O)(OH)_2$), alkyl″ phosphate (($CH_2)_nOP(=O)(OH)_2$), etc.

In various embodiments, the above listed moieties are attached at the $R^1$—$R^6$ positions in any suitable conformation. In some embodiments, the above listed functional groups are combined to produce the substituents depicted in compounds B1-B86 of Table 1. In other embodiments, additional compounds, not depicted in Table 1 or described herein by name or formula, are formed by combination of formula I and the functional groups described herein. In some embodiments, substituents not depicted in Table 1 or explicitly listed herein, are within the scope of the present invention, and may be appended formula I to yield compositions within the scope of the present invention.

Formula I is provided herein as an exemplary scaffold of the general class of compounds provided herein. While this scaffold, with any combination of the substituents depicted or described herein (e.g., explicitly or through combination of functional groups), is within the scope of embodiments of the invention, the present invention is not limited to such compounds. Compounds comprising substitutions and/or addition/deletion of substituents that produce functional equivalents and/or improved functionality (e.g., enhanced therapeutic effect, enhanced bioavailability, improved human tolerance, reduced side effects, etc.) are also within the scope of embodiments of the present invention. For example, in some embodiments, compounds of the present invention comprise a general formula of formula II:

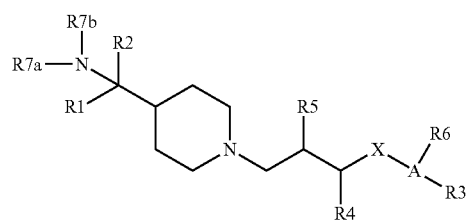

In other embodiments, compositions are limited to compounds defined by a subset of formulas I and/or II. For example, in some embodiments, compounds are limited to those with at least one heterocycle at $R^1$ and/or $R^2$. In certain embodiments, Y is limited to $OR^7$, wherein $R^7$ is not H. In some embodiments, compounds are limited to those without an OH at the Y position. Other exemplary embodiments comprise a heterocycle at the A position. Compounds and compositions may also contain additional limitation on the scope of suitable compounds.

In some embodiments, the present invention provides compositions and methods for prevention and/or treatment of leukemia (e.g. MLL-related leukemia and other acute leukemias). In some embodiments, the present invention provides compositions and method for the inhibition of the protein-protein interaction between menin and MLL fusion proteins and/or menin and MLL wild type proteins (both MLL1 and MLL2). In some embodiments, compositions and methods inhibit the interaction that is important for the oncogenic (e.g. leukemogenic) potential of MLL fusions. In some embodiments, the present invention provides small molecule inhibitors of interactions between menin and MLL fusion proteins and/or menin and MLL wild type proteins (both MLL1 and MLL2). In some embodiments, compositions and methods reverse (e.g. inhibit, decrease, abolish, etc.) the oncogenic (e.g. leukemogenic) potential of MLL fusion proteins, MLL-PTDs (Partial Tandem Duplications) and MLL wild type. In some embodiments, compositions find utility in targeted therapies (e.g. anti-leukemia agents). In some embodiments, compounds block menin-MLL interactions.

In some embodiments, the present invention provides compositions which inhibit the interaction between MLL (e.g. MLL fusion proteins and MLL wild type) and menin. In some embodiments, any compounds, small molecules (e.g. pharmaceuticals, drugs, drug-like molecules, etc.), macromolecules (e.g. peptides, nucleic acids, etc.) and/or macromolecular complexes which inhibit the MLL-menin interaction find utility in the present invention. In some embodiments, the present invention provides small molecule compounds which inhibit MLL-menin and MLL fusion protein-menin interactions. In some embodiments, compositions of the present invention decrease the affinity of menin for MLL fusion proteins and/or MLL (e.g. MLL wild type protein) for menin. In some embodiments, compositions of the present invention disrupt bonding (e.g. hydrogen bonding, ionic bonding, covalent bonding, etc.), molecular interactions (e.g. hydrophobic interactions, electrostatic interactions, van der Waals interactions, etc.), shape recognition, and/or molecular recognition between MLL (e.g. MLL fusion proteins or MLL wild type protein) and menin. However, an understanding of the mechanisms of action is not required to practice the invention and the invention is not limited to any particular mechanism of action.

In some embodiments, compounds are provided that exhibit a threshold level of inhibition the MLL-menin interaction (e.g., as determined by a suitable assay (e.g., fluorescence polarization competition experiments)). In some embodiments, compounds exhibit an effectiveness (e.g., in vitro activity) in inhibiting the menin-MLL interaction, as measured by $IC_{50}$ value, of less than 100 µM (e.g., <1 nM ... 10 nM ... 100 nM ... 1 µM ... 10 µM ... 50 µM). In some embodiments, compounds have $IC_{50}$ values of less than 10 µM, less that 1 µM, less than 100 nM, less than 10 nM, etc. (e.g., as determined by fluorescence polarization competition assay).

The present invention provides any small molecules or classes of small molecules which disrupt, target, or inhibit MLL/menin and MLL fusion protein/menin interactions; and/or treat/prevent leukemia. In some embodiments, small molecules are effective in inhibiting the interaction of MLL-fusion proteins with menin or MLL wild type protein with menin. In particular embodiments, the present invention provides a class of small molecules comprising the general structure of formula I. In some embodiments, small molecules of the present invention inhibit the interaction of MLL (e.g. MLL-fusion proteins or MLL wild type, both MLL1 and MLL2) with menin. In some embodiments, small molecules of the present invention inhibit the oncogenic (e.g. leukemogenic) effects of MLL-fusion proteins, and/or MLL-menin and MLL fusion protein-menin interactions. In some embodiments, small molecules of the present invention treat and/or prevent leukemia (e.g. MLL-dependant leukemias, MLL-related leukemias, or other leukemias with and without high level of HOX genes expression etc.).

In some embodiments, the present invention provides administration of compositions of the present invention to subjects (e.g. leukemia patients) to treat or prevent disease (e.g. cancer, leukemia, MLL-related leukemia, etc.). In some embodiments, the present invention provides administration of compositions for the treatment or prevention of leukemia (e.g. acute leukemias, chronic leukemias, lymphoblastic leukemias, lymphocytic leukemias, myeloid leukemias, myelogenous leukemias, Acute lymphoblastic leukemia (ALL), Chronic lymphocytic leukemia (CLL), Acute myelogenous leukemia (AML), Chronic myelogenous leukemia (CML), Hairy cell leukemia (HCL), T-cell prolymphocytic leukemia (T-PLL), Large granular lymphocytic leukemia, MLL-positive leukemias, MLL-induced lukemias, leukemias with MLL rearrangements, MLL-PTD leukemias, etc.).

In some embodiments, any of the compounds described herein are co-administered or used in combination with a known therapeutic agent (e.g., methotrexate, 6-mercaptopurine, antibody therapies, etc.). In some embodiments, a compound of the present invention is co-administered with another therapeutic agent effective in treating one or more leukemias.

In some embodiments, a compound of the present invention is co-administered with one or more therapeutic agents approved for the treatment of Acute Lymphoblastic Leukemia (ALL), for example: ABITREXATE (Methotrexate), ADRIAMYCIN PFS (Doxorubicin Hydrochloride), ADRIAMYCIN RDF (Doxorubicin Hydrochloride), ARRANON (Nelarabine), Asparaginase *Erwinia chrysanthemi*, CERUBIDINE (Daunorubicin Hydrochloride), CLAFEN (Cyclophosphamide), CLOFARABINE, CLOFAREX (Clofarabine), CLOLAR (Clofarabine), Cyclophosphamide, Cytarabine, CYTOSAR-U (Cytarabine), CYTOXAN (Cyclophosphamide), Dasatinib, Daunorubicin Hydrochloride, Doxorubicin Hydrochloride, Erwinaze (Asparaginase *Erwinia Chrysanthemi*), FOLEX (Methotrexate), FOLEX PFS (Methotrexate), GLEEVEC (Imatinib Mesylate), ICLUSIG (Ponatinib Hydrochloride), Imatinib Mesylate, MARQIBO (Vincristine Sulfate Liposome), Methotrexate, METHOTREXATE LPF (Methorexate), MEXATE (Methotrexate), MEXATE-AQ (Methotrexate), Nelarabine, NEOSAR (Cyclophosphamide), ONCASPAR (Pegaspargase), Pegaspargase, Ponatinib Hydrochloride, RUBIDOMYCIN (Daunorubicin Hydrochloride), SPRYCEL (Dasatinib), TARABINE PFS (Cytarabine), VINCASAR PFS (Vincristine Sulfate), Vincristine Sulfate, etc.

In some embodiments, a compound of the present invention is co-administered with one or more therapeutic agents approved for the treatment of Acute Myeloid Leukemia (AML), for example: ADRIAMYCIN PFS (Doxorubicin Hydrochloride), ADRIAMYCIN RDF (Doxorubicin Hydrochloride), Arsenic Trioxide, CERUBIDINE (Daunorubicin Hydrochloride), CLAFEN (Cyclophosphamide), Cyclophosphamide, Cytarabine, CYTOSAR-U (Cytarabine), CYTOXAN (Cyclophosphamide), Daunorubicin Hydrochloride, Doxorubicin Hydrochloride, NEOSAR (Cyclophosphamide), RUBIDOMYCIN (Daunorubicin Hydrochloride), TARABINE PFS (Cytarabine), TRISENOX (Arsenic Trioxide), VINCASAR PFS (Vincristine Sulfate), Vincristine Sulfate, etc.

In some embodiments, a compound of the present invention is co-administered with one or more therapeutic agents approved for the treatment of Chronic Lymphocytic Leukemia (CLL), for example: Alemtuzumab, AMBOCHLORIN (Chlorambucil), AMBOCLORIN (Chlorambucil), ARZERRA (Ofatumumab), Bendamustine Hydrochloride, CAMPATH (Alemtuzumab), CHLORAMBUCILCLAFEN (Cyclophosphamide), Cyclophosphamide, CYTOXAN (Cyclophosphamide), FLUDARA (Fludarabine Phosphate), Fludarabine Phosphate, LEUKERAN (Chlorambucil), LINFOLIZIN (Chlorambucil), NEOSAR (Cyclophosphamide), Ofatumumab, TREANDA (Bendamustine Hydrochloride), etc.

In some embodiments, a compound of the present invention is co-administered with one or more therapeutic agents approved for the treatment of Chronic Myelogenous Leukemia (CML), for example: BOSULIF (Bosutinib), Bosutinib, CLAFEN (Cyclophosphamide), Cyclophosphamide, Cytarabine, CYTOSAR-U (Cytarabine), CYTOXAN (Cyclophosphamide), Dasatinib, GLEEVEC (Imatinib Mesylate), ICLUSIG (Ponatinib Hydrochloride), Imatinib Mesylate, NEOSAR (Cyclophosphamide), Nilotinib, Omacetaxine Mepesuccinate, Ponatinib Hydrochloride, SPRYCEL (Dasatinib), SYNRIBO (Omacetaxine Mepesuccinate), TARABINE PFS (Cytarabine), TASIGNA (Nilotinib), etc.

In some embodiments, a compound of the present invention is co-administered with one or more therapeutic agents approved for the treatment of Meningeal Leukemia, for example: CYTARABINE, CYTOSAR-U (Cytarabine), TARABINE PFS (Cytarabine), etc.

In some embodiments, the compositions of the present invention are provided as pharmaceutical and/or therapeutic compositions. The pharmaceutical and/or therapeutic compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for topical administration can include transdermal patches, ointments, lotions, creams, gels, drops, suppositories, sprays, liquids and powders. Conventional carriers; aqueous, powder, or oily bases; thickeners; and the like can be necessary or desirable. Compositions and formulations for oral administration include powders or granules, suspensions or solutions in water or non aqueous media, capsules, sachets or tablets. Thickeners, flavoring agents, diluents, emulsifiers, dispersing aids or binders can be desirable. Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Pharmaceutical and/or therapeutic compositions of the present invention include, but are not limited to, solutions, emulsions, and liposome containing formulations. These compositions can be generated from a variety of components that include, but are not limited to, preformed liquids, self emulsifying solids and self emulsifying semisolids.

The pharmaceutical and/or therapeutic formulations of the present invention, which can conveniently be presented in unit dosage form, can be prepared according to conventional techniques well known in the pharmaceutical/nutriceutical industries. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

Dosing and administration regimes are tailored by the clinician, or others skilled in the pharmacological arts, based upon well known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone. Dosing may be once per day or multiple times per day for one or more consecutive days.

In some embodiments, compounds and compositions of the present invention are prepared using any suitable synthesis and manufacturing techniques. In certain embodiments, compounds are prepared according to the following general methods.

In various embodiments, compounds of type 1.3 can be prepared according to Scheme 1 below, starting from an appropriate 4-methanol substituted piperidine, addition with a 1,3-dihalosubstituted propane gives intermediate 1.2A which upon treatment with base, such as potassium carbonate or sodium hydride, in an aprotic solvent, such dimethylformamide, and a heteroaryl or aryl phenol or amine gives examples of type 1.3. Alternatively, reaction of 1.1 with epichlorohydrin derivatives provides intermediate 1.2B which upon treatment with base and a phenol or amine gives examples of type 1.3.

SCHEME 1

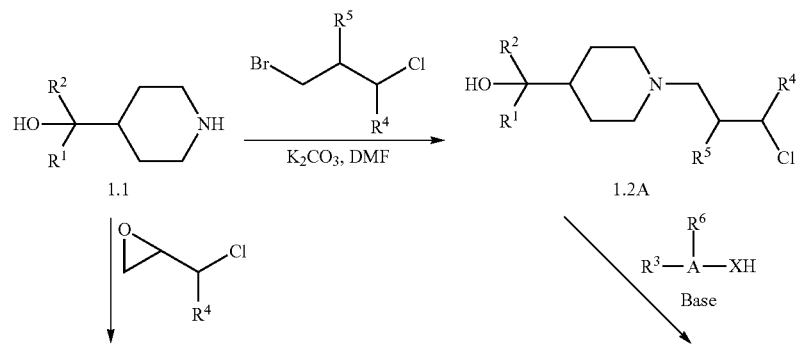

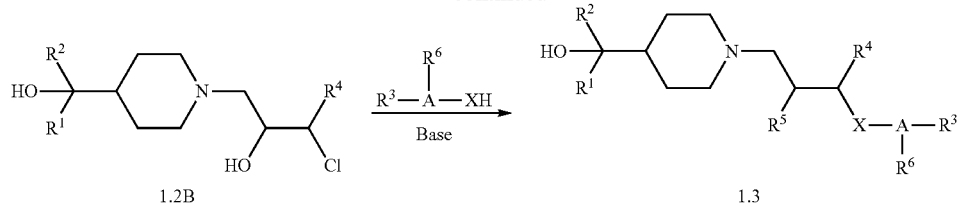

Alternatively, compounds may be prepared according to Scheme 2 starting from an appropriate amino ketone 2.1, double alkylation as before gives ketone 2.3, which upon treatment with an appropriate $R^2$ Grignard reagent or organolithium reagent provides tertiary carbinols of type 2.4A.

3.3. Subsequent addition of an appropriate $R^1$ group, followed by deprotection using hydrogenolysis conditions gives 3.5. Final two-step alkylation using the previously described conditions (Scheme 1, e.g. 1A or 1B) provides examples of type 3.7 (Method A) or alternatively alkylation using previ-

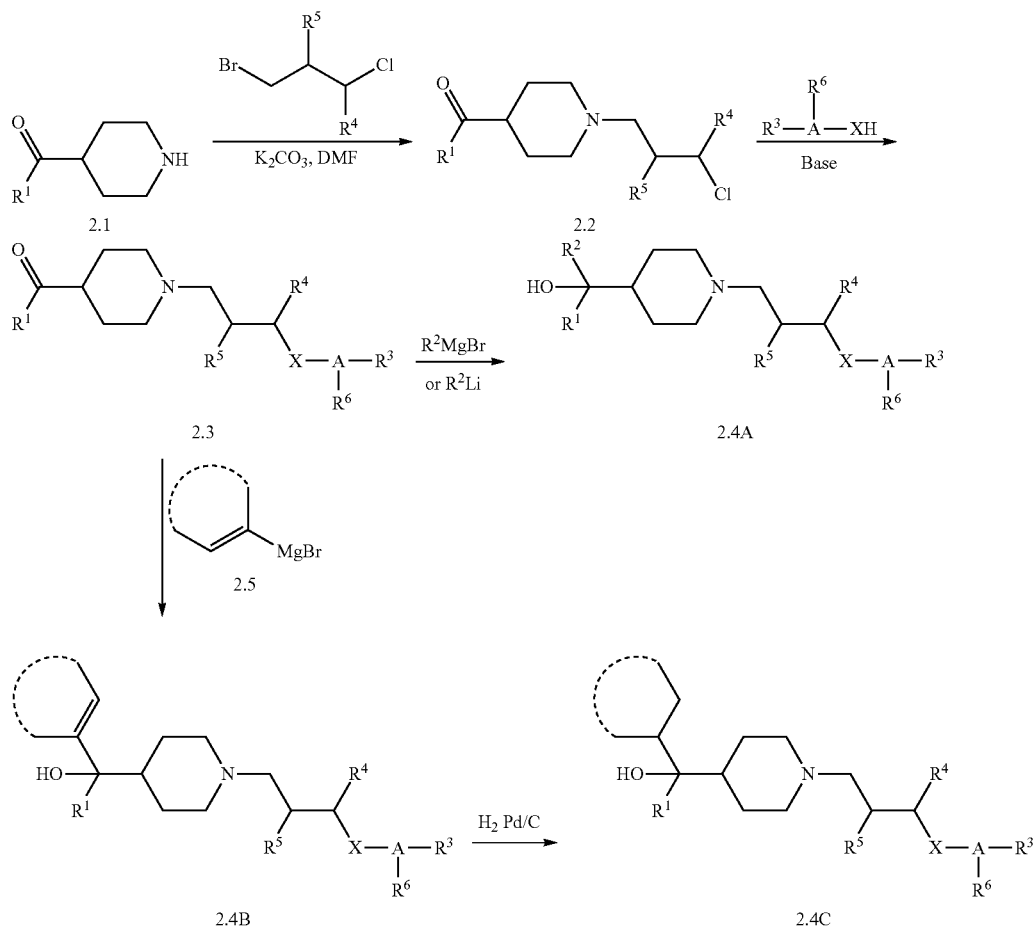

In another embodiment for $R^2$ substitution selected from alkyl, alkenyl, cycloalkyl, or cycloalkenyl the Grignard reagent may optionally be prepared from an appropriate bromide precursor to give 2.5 which upon treatment with 2.3 give examples of type 2.4B. Furthermore, optional reduction of 2.4B using hydrogen and a heterogeneous catalyst, such as palladium on carbon, gives additional examples of type 2.4C.

Alternatively, in some embodiments, compounds are prepared according to Scheme 3. Starting from 4-cyanopiperidine hydrochloride 3.1 benzyl protection gives intermediate 3.2. Addition of Grignard or organolithium R2 gives ketone ously prepared bromide intermediate 3.6 can accomplish formation of examples 3.7.

SCHEME 3

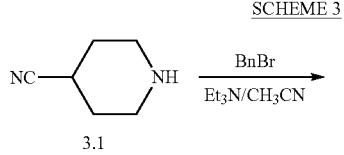

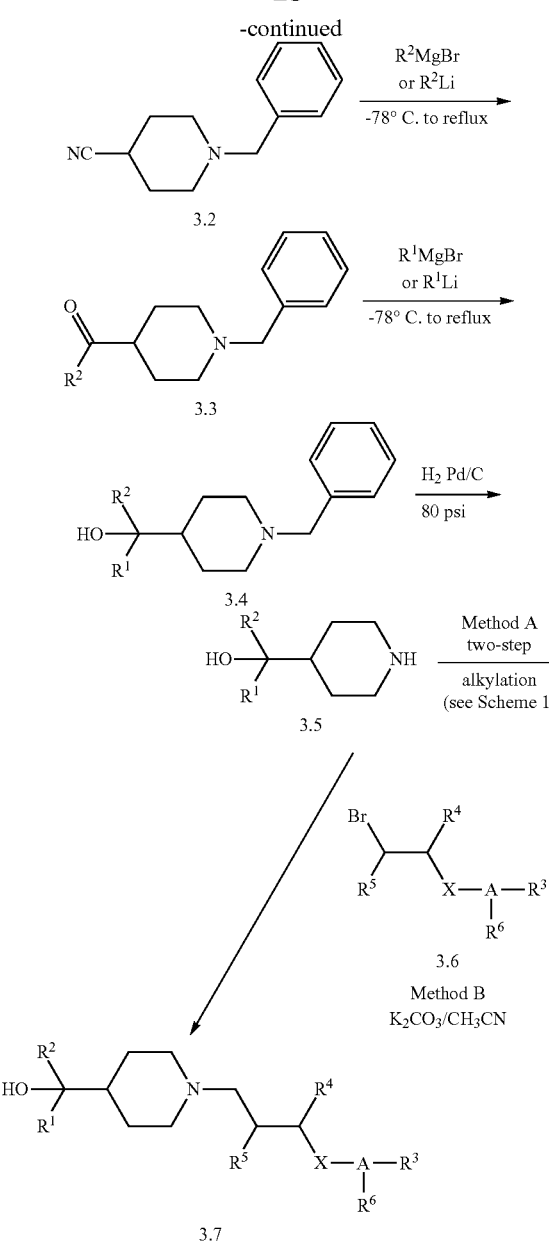

In another embodiment, compounds are prepared according to Scheme 4 wherein intermediate 3.3 (prepared according to Scheme 3) is first deprotected to give aminoketone 4.1. Alkylation as previously described (Schemes 1 and 3) provides penultimate ketone 4.2, which upon subsequent treatment with organometallic reagent derived from $R^1$ gives example compounds 4.3.

SCHEME 4

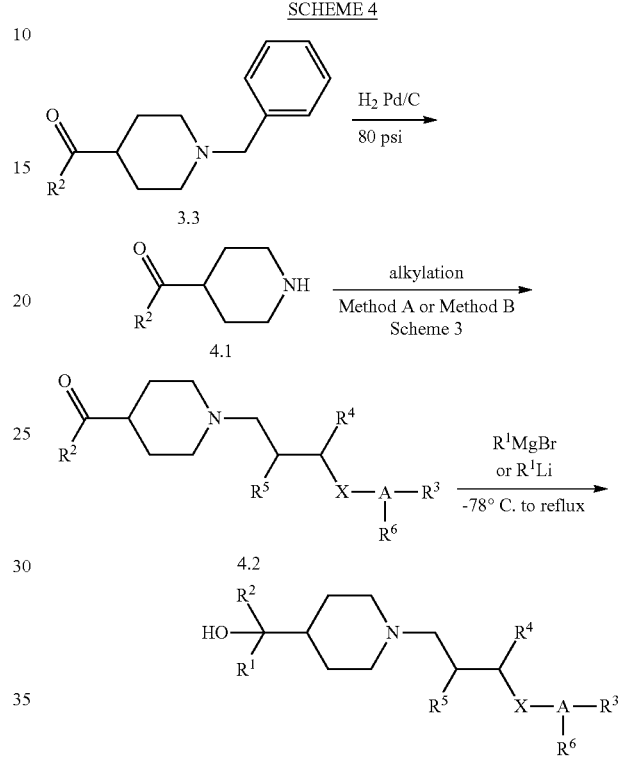

Alternatively, certain R3 modifications are performed according to the general route outlined in Scheme 5 wherein the penultimate nitrile 5.1 is further modified to give examples 5.2A and 5.2B via basic hydrolysis. Reduction of nitrile 5.1 using Raney-Nickel and hydrogen gives example benzyl amine 5.3, which is subsequently functionalized with acid and sulfonyl chlorides to give amide 5.4A and sulfonamide 5.4B, respectively.

SCHEME 5

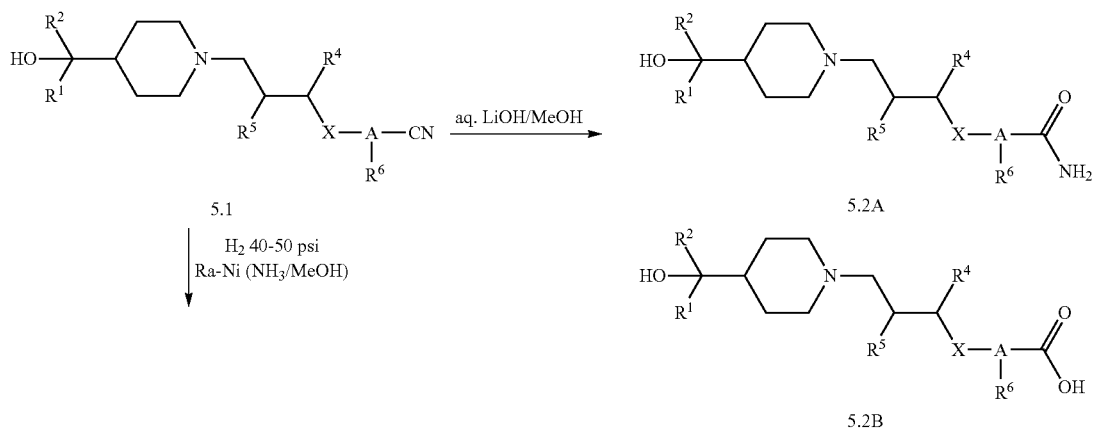

-continued

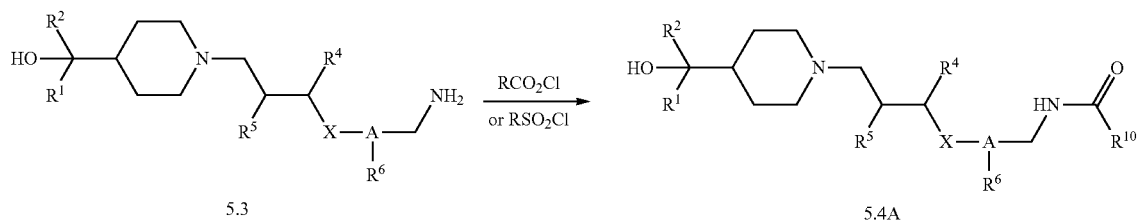

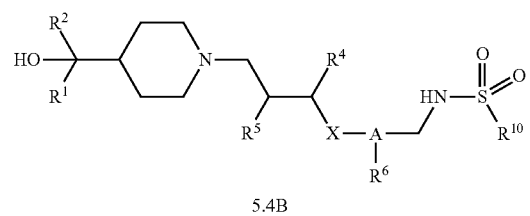

In some embodiments, compounds of type 6.1, 6.2, 6.3A, and 6.3B are obtained as outlined in Scheme 6. Imide 6.1, obtained using methods from Schemes 1-4, is treated with hydrazine to provide examples of type 6.2. Aromatic amine 6.2 is further functionalized to give amides and sulfonamides 6.3A and 6.3B, respectively.

SCHEME 6

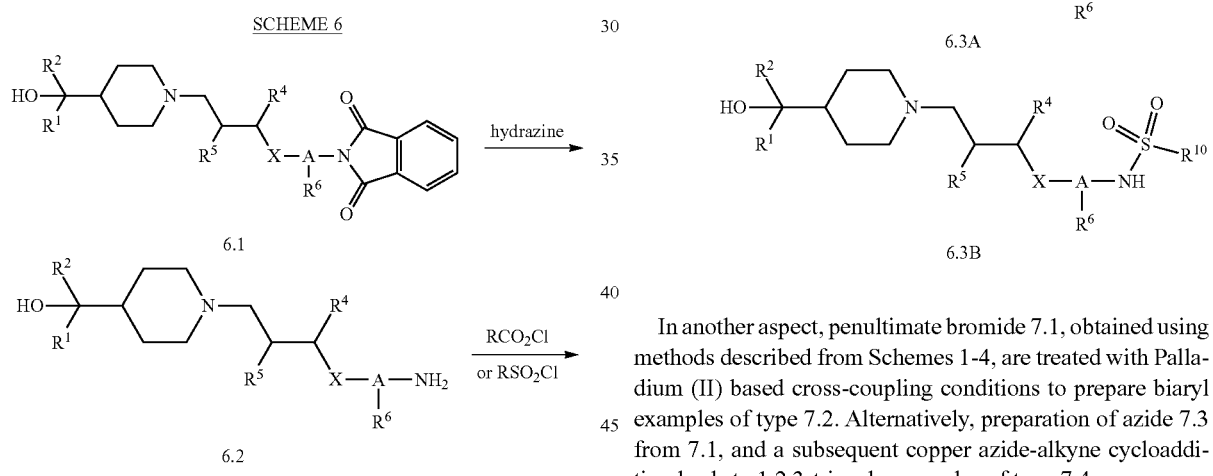

In another aspect, penultimate bromide 7.1, obtained using methods described from Schemes 1-4, are treated with Palladium (II) based cross-coupling conditions to prepare biaryl examples of type 7.2. Alternatively, preparation of azide 7.3 from 7.1, and a subsequent copper azide-alkyne cycloaddition leads to 1,2,3-triazole examples of type 7.4.

SCHEME 7

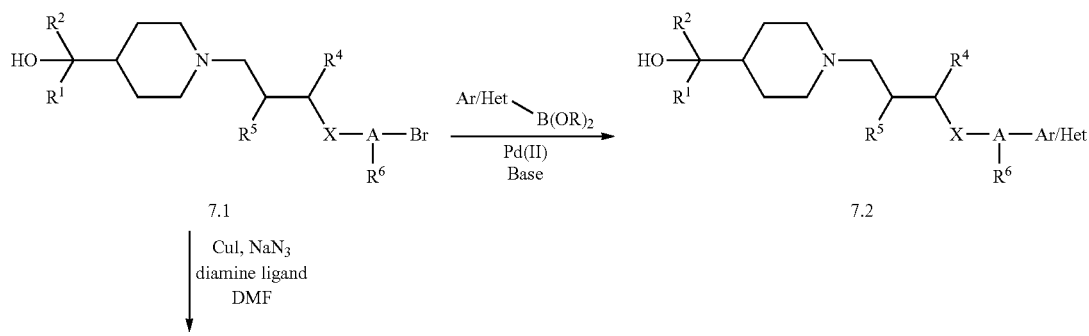

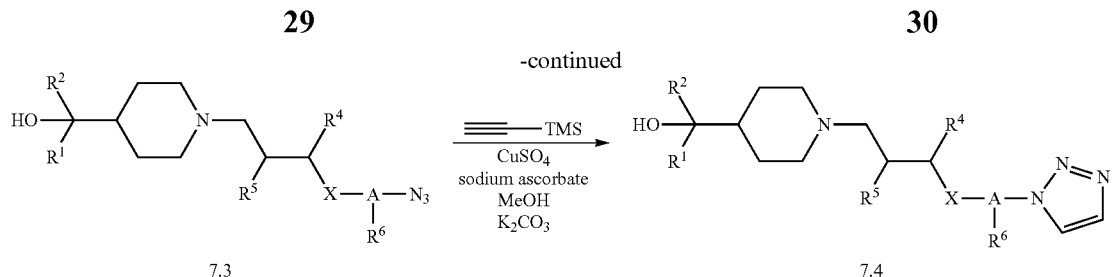

7.3 → 7.4

In another embodiment, compounds are prepared according to Scheme 8 wherein hydroxyl examples of type 8.1 is treated with strong acid in the presence of sodium azide. The solvolysis reaction provides azide intermediate 8.2, which upon reduction provides example 8.3. In another aspect, example amine 8.3 is treated with an alkylating agent or an aldehyde or bis aldehyde under reducing conditions using for example, sodium borohydride, to give examples 8.4A and 8.4B.

piperidine 9.1, addition with a 1,3-dihalosubstituted propane gives haloalkyl piperidines of type 9.2. Treatment with the appropriate $R_1$ Grignard reagent or organolithium reagent provides the appropriate tertiary carbinol 9.3. Upon treatment with base, such as potassium carbonate or sodium hydride, in an aprotic solvent, such dimethylformamide, and a heteroaryl or aryl phenol or amine gives examples of type 9.4.

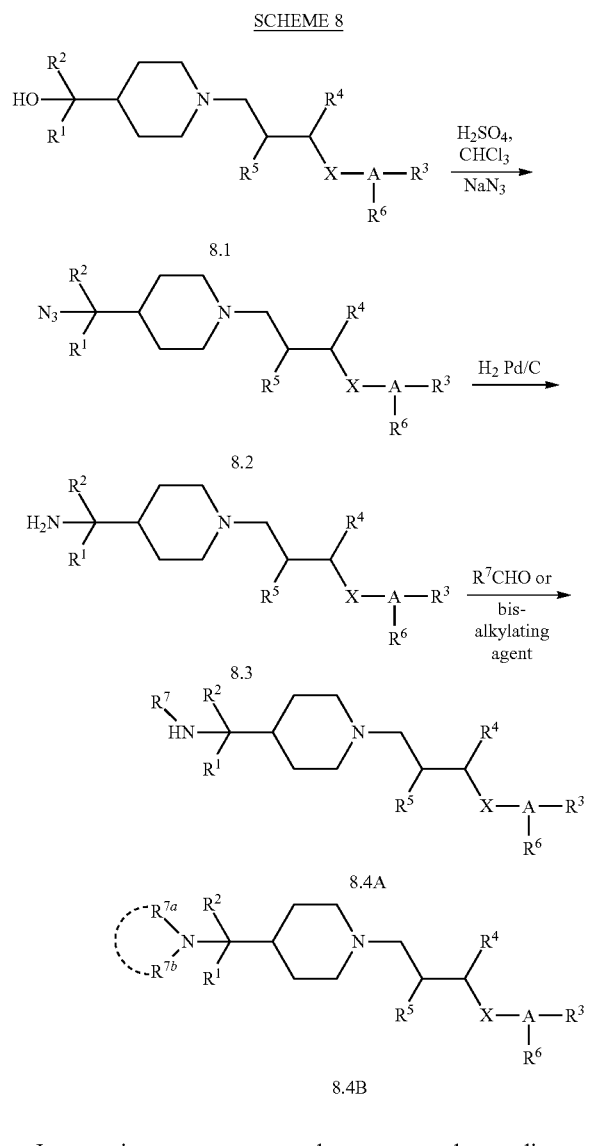

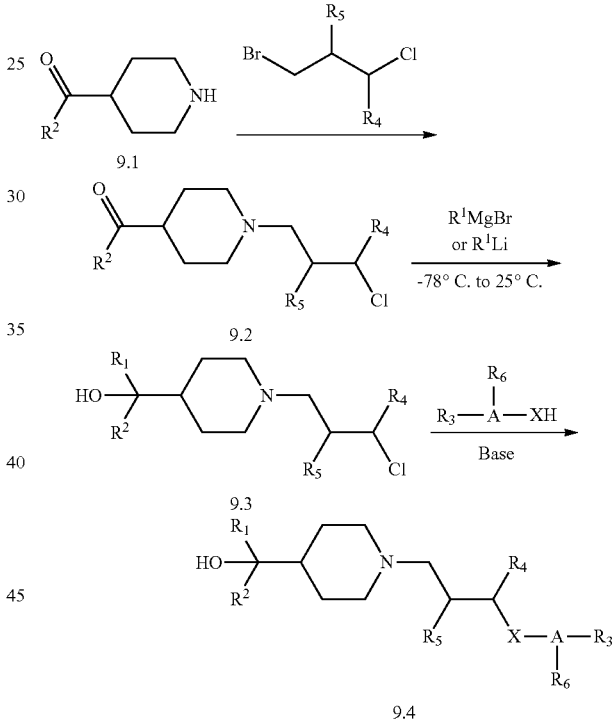

In other embodiments, compounds may be prepared according to Scheme 10 wherein intermediate 1.1 (prepared according to scheme 1) treated with base and epoxide derivatives provide examples of type 10.2.

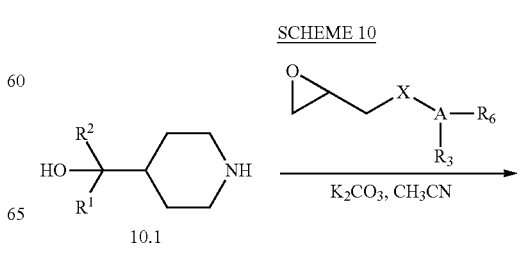

In some instances, compounds are prepared according to Scheme 9 wherein starting from an appropriate 4-substituted -continued

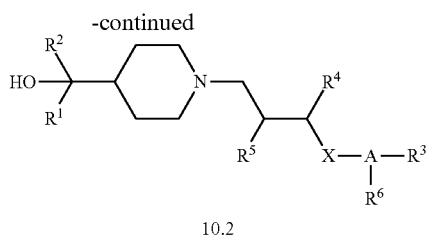

10.2

The above synthesis schemes are exemplary. Compounds are not limited to those produced through, or capable of being produced through such methods.

EXPERIMENTAL

As used herein, the term "EtOAc" means ethyl acetate, "DCM" means dichloromethane, "DIPEA" means N,N-diisopropylethylamine, "DMF" means N,N-dimethylformamide, "DTBAD" means di-tert-butyl azodicarboxylate, "HATU" means 2-(7-aza-1H-benzotriazole-1-yl)-1,1,3,3-tetramethyluronium hexafluorophosphate, "LCMS" means liquid chromatography/mass spectrometry, "MeOH" means methanol, "[M+H]$^+$" means the protonated mass of the free base of the compound, "M. p." means melting point, "NMR" means nuclear magnetic resonance, "$R_t$" means retention time (in minutes), "THF" means tetrahydrofuran.

Microwave assisted reactions were performed in a single-mode reactor: Emrys™ Optimizer microwave reactor (Personal Chemistry A.B., currently Biotage).

Hydrogenation reactions were performed in a continuous flow hydrogenator H-CUBE® from ThalesNano Nanotechnology Inc. or using a Parr hydrogenation shaker apparatus.

Analytical thin layer chromatography was performed on Analtech silica gel GF 250 micron plates using reagent grade solvents. Normal phase flash silica gel-based column chromatography was performed using ready-to-connect cartridges from ISCO, on irregular silica gel, particle size 15-40 µm on a Combi-flash Companion chromatography system from ISCO.

Low resolution mass spectra were obtained on an Agilent 1200 series 6130 mass spectrometer. High resolution mass spectra were recorded on a Waters Q-TOF API-US. Analytical HPLC was performed on an HP 1100 with UV detection at 214 and 254 nm along with ELSD detection, LC/MS (J-Sphere80-C18, 3.0×50 mm, 4.1 min gradient, 5%[0.05% TFA/CH$_3$CN]:95%[0.05% TFA/H$_2$O] to 100%[0.05% TFA/CH$_3$CN]. Preparative RP-HPLC purification was performed on a custom HP 1100 automated purification system with collection triggered by mass detection or using a Gilson Inc. preparative UV-based system using a Phenomenex Luna C18 column (50×30 mm I.D., 5 µm) with an acetonitrile (unmodified)-water (0.1% TFA) custom gradient.

For LC-MS-characterization of the compounds of the present invention, the following methods were used.

Method 1: The HPLC measurement was performed using an Agilent 1200 system comprising a binary pump with degasser, an autosampler, a column oven, a diode-array detector (DAD) and a column as specified in the respective methods below. Flow from the column was split to a SQ mass spectrometer and Polymer Labs ELSD. The MS detector was configured with an ES ionization source. Nitrogen was used as the nebulizer gas. The source temperature was maintained at 350° C. Data acquisition was performed with Agilent Chemstation software. Reversed phase HPLC was carried out on a Kinetex C18 column (2.6 µm, 2.1×30 µm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 µL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

Method 2: Using method 1 instrument and column conditions. The gradient conditions used are: 93% A (water+0.1% TFA), 7% B (acetonitrile), to 95% B in 2.0 minutes, returning to initial conditions at 2.11 minutes. Injection volume 1 µL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

Chiral purification of racemic mixtures was readily accomplished using a supercritical fluid chromatography (SFC) instrument from Thar Scientific Instruments. Chiral analytical and semi-prep SFC purification columns were from Chiral Technologies.

$^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

Example 1

Preparation of intermediate (1-(3-(4-bromophenoxy)propyl)piperidin-4-yl)diphenylmethanol (A1)

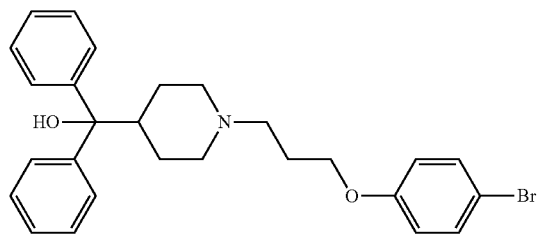 [SMILES: OC(c1ccccc1)(c1ccccc1)C1CCN(CCCOc2ccc(Br)cc2)CC1]

Step 1. To a DMF solution (40 mL) of 4-benzoylpiperdine hydrobromide (2.70 g, 10 mmol) and K$_2$CO$_3$ (6.9 g, 50 mmol) was added 1-bromo-3-chloropropane (1.55 g, 10 mmol). The reaction progress was monitored by LC-MS and upon completion of the reaction (~2 h) the mixture was poured onto EtOAc (60 mL) and water (25 mL). The organic layer was removed and the aqueous phase extracted with EtOAc (2×40 mL). The organic layers were combined, washed sequentially with aq. LiCl and brine, and then dried over Na2SO4 and concentrated to dryness under reduced pressure to afford (1-(3-chloropropyl)piperidin-4-yl)diphenylmethanol (3.0 g, 86%).

Step 2. The crude chloride (0.5 g, 1.45 mmol) from step 1 was dissolved in CH$_3$CN (12 mL) with K$_2$CO$_3$ (270 mg, 2.81 mml) and treated with excess 4-bromophenol (775 mg, 4.35 mmol). The mixture was allowed to stir overnight at rt. The reaction was poured into H$_2$O and extracted with EtOAc (3×20 mL). The combined organic layers were washed with brine, dried over Na$_2$SO$_4$, and evaporated to give the crude bromide. Purification over silica gel (EtOAc/hexanes) using automated normal phase chromatography provided title bromide as a clear viscous oil (550 mg, 79%): LC-MS (>98%) m/z=480.3 [M+H].

Example 2

Preparation of 4-(3-(4-(hydroxydiphenylmethyl)piperidin-1-yl)propoxy)benzonitrile (B1)

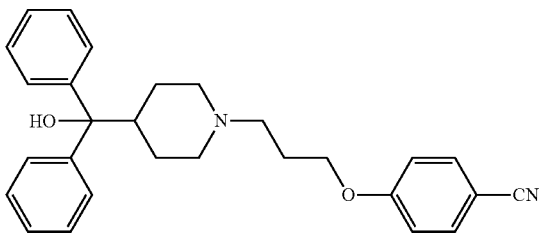 [SMILES: N#Cc1ccc(OCCCN2CCC(C(O)(c3ccccc3)c3ccccc3)CC2)cc1]

Step 1. 4-Benzoylpiperdine hydrobromide (2.70 g, 10 mmol) was combined with K$_2$CO$_3$ (6.9 g, 50 mmol) in DMF (~40 mL), followed by 1-bromo-3-chloropropane (1.55 g, 10 mmol). The reaction progress was monitored by LC-MS and upon completion of the reaction (~2 h) 4-cyanophenol (1.3 g, 11 mmol) was added and the reaction allowed to stir overnight. The mixture was poured onto water and extracted with ethyl acetate, washed with brine and dried over Na$_2$SO$_4$. The volatiles were removed under reduced pressure and the crude mixture purified on silica gel (0-100% EtOAc in hexanes) to give 2.71 g (78% yield over 2 steps) of 4-(3-(4-benzoylpiperidin-1-yl)propoxy)benzonitrile: LC-MS (>98%) m/z=349.2 [M+H].

Step 2. 4-(3-(4-Benzoylpiperidin-1-yl)propoxy)benzonitrile (0.5 g, 1.4 mmol) was dissolved in dry THF (~15 mL), and a solution of phenylmagnesium bromide (0.9 mL, 2M, 1.8 mmol) was added and the reaction stirred for 6 h. The reaction was quenched (sat. NH$_4$Cl) and extracted into EtOAc (2×). The organic layers were dried over Na$_2$SO$_4$ and the volatiles removed under reduced pressure. The crude residue was purified on silica gel (EtOAc/hexanes) to give 417 mg (70% yield) of title compound Example B1: $^1$H NMR (400 MHz, CDCl$_3$) δ 7.58 (2H, d, J=8.8 Hz), 7.50 (4H, d, J=7.6), 7.30 (4H, q, J=8), 7.20 (2H, t, J=7.2 Hz), 6.94 (2H, d, J=8.8 Hz), 4.06 (2H, t, J=6 Hz), 3.07 (2H, d, J=11.2 Hz), 2.59 (2H, t, J=7.2 Hz), 2.53-2.46 (1H, m), 2.14-2.01 (4H, m), 1.66-1.55 (4H, m), LC-MS (>98%) m/z=427.0 [M+H]; HRMS=427.2386 [M+H], 100% calculated for C$_{28}$H$_{31}$N$_2$O$_2$, 427.2386.

Example 3

Preparation of 4-(3-(4-(cyclopentyl(hydroxy)(phenyl)methyl)piperidin-1-yl)propoxy)benzonitrile (B11)

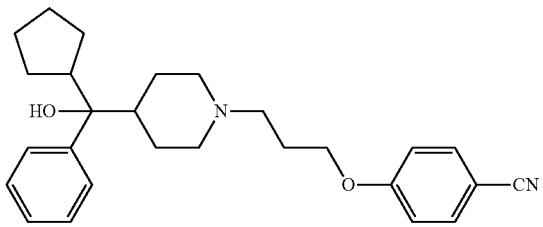 [SMILES: N#Cc1ccc(OCCCN2CCC(C(O)(c3ccccc3)C3CCCC3)CC2)cc1]

Step 1. 4-(3-(4-Benzoylpiperidin-1-yl)propoxy)benzonitrile. 4-Benzoylpiperdine hydrobromide (2.70 g, 10 mmol) was combined with K$_2$CO$_3$ (6.9 g, 50 mmol) in DMF (~40 mL), followed by 1-bromo-3-chloropropane (1.55 g, 10 mmol). The reaction progress was monitored by LC-MS and upon completion of the reaction (~2 h) 4-cyanophenol (1.3 g, 11 mmol) was added and the reaction allowed to stir overnight. The mixture was poured onto water and extracted with ethyl acetate, washed with brine (2×) and dried over Na$_2$SO$_4$. The volatiles were removed under reduced pressure and the crude mixture purified on silica gel (0-100% EtOAc in hexane) to give 2.71 g (78% yield over 2 steps) of the title intermediate compound: LC-MS (>98%) m/z=349.2 [M+H].

Step 2. 4-(3-(4-Benzoylpiperidin-1-yl)propoxy)benzonitrile (1.4 g, 4 mmol) was dissolved in dry THF (~25 mL), heated to 60° C. and a solution of cyclopentylmagnesium chloride (4 mL, 2M) was added and the reaction stirred for 1 h. The reaction was quenched (sat. NH$_4$Cl) and extracted into EtOAc (2×). The organic layers were dried over Na$_2$SO$_4$ and the volatiles removed under reduced pressure. The crude residue was purified on silica gel (0-4% MeOH in CH$_2$Cl$_2$). The combined fractions were further purified by reverse phase chromatography to give 117 mg (7% yield) of analytically pure title compound: $^1$H NMR (400 MHz, CDCl$_3$) δ 7.54 (2H, d, J=8.8 Hz), 7.37 (2H, d, J=7.6 Hz), 7.31 (2H, t, J=7.6 Hz), 7.22 (1H, t, J=7.2 Hz), 6.89 (2H, d, J=8.8 Hz), 4.02 (2H, t, J=6 Hz), 3.12-3.00 (2H, m), 2.74-2.62 (3H, m), 2.09-1.95 (4H, m), 1.80-1.60 (4H, m), 1.58-1.40 (7H, m), 1.25-1.24 (1H, m), 1.11-1.09 (1H, m); LC-MS (>98%) m/z=419.3 [M+H]; HRMS=419.2701 [M+H], 100%, calculated for C$_{27}$H$_{35}$N$_2$O$_2$, 419.2699.

Example 4

Preparation of 4-(3-(4-(amino(cyclopentyl)(phenyl)methyl)piperidin-1-yl)propoxy)benzonitrile (B71)

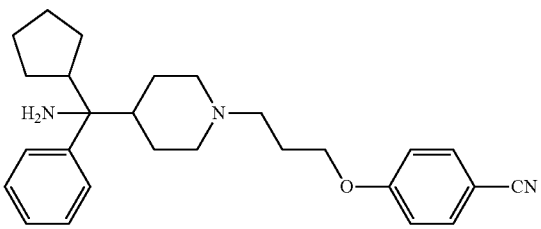 [SMILES: N#Cc1ccc(OCCCN2CCC(C(N)(c3ccccc3)C3CCCC3)CC2)cc1]

Step 1. A CHCl$_3$ (4.78 mL, 0.25 M) solution of 4-(3-(4-(cyclopentyl(hydroxy)(phenyl)methyl)piperidin-1-yl)propoxy)benzonitrile (0.5 g, 1.19 mmol) and sodium azide (1.16 g, 17.9 mmol) was cooled to 0° C. To the solution H$_2$SO$_4$ was added dropwise (0.28 mL, 9.3 mmol). The mixture was allowed to warm to rt over 4 h with stirring, then re-cooled to 0° C. and treated with NH$_4$OH till pH was basic. The biphasic solution was extracted with DCM (3×) and the organic layers combined and dried over MgSO$_4$. Concentration under reduced pressure and drying in vacuo afforded a crude oil. Purification by flash chromatography (DCM, MeOH, NH$_4$OH) afforded 4-(3-(4-(azido(cyclopentyl)(phenyl)methyl)piperidin-1-yl)propoxy)benzonitrile (45 mg, 10%): LC-MS (>98%) m/z=444.3 [M+H].

Step 2. 4-(3-(4-(azido(cyclopentyl)(phenyl)methyl)piperidin-1-yl)propoxy)benzonitrile (30 mg, 0.07 mmol) was dissolved in degassed EtOH (0.5 mL) and Pd/C (2.7 mg) added in one portion. Reaction was placed under a balloon of H$_2$ gas and allowed to stir for 4 h while stirring at rt. The reaction was filtered over Celite and rinsed with MeOH. The filtrate was concentrated to afford an oil. RP-HPLC preparative purification afforded the title compound 4-(3-(4-(cyclopentyl(hydroxy)(phenyl)methyl)piperidin-1-yl)propoxy)benzonitrile as a TFA salt. The mixture was treated with a StratoSpheer SPE MP-carbonate resin to give title compound as a free base (5.6 mg, 20%): $^1$H NMR (400 MHz, CDCl$_3$) δ 7.54 (2H, d, J=6.0 Hz), 7.43 (2H, d, J=7.2 Hz), 7.31 (2H, t, J=7.2 Hz), 7.22 (1H, t, J=7.2 Hz), 6.91 (2H, d, J=6.0 Hz), 4.02 (2H, t, J=8.4 Hz), 3.05-2.96 (2H, m), 2.62 (1H, m), 2.47 (br s, 2H), 1.96-1.89 (4H, m), 1.73 (1H, m), 1.62-1.40 (9H, m), 1.29-1.24 (2H, m), 1.13-1.05 (2H, m); LC-MS (>98%) m/z=418.0 [M+H].

Example 5

Preparation of (1-(3-(4-(1H-1,2,3-triazol-1-yl)phenoxy)propyl)piperidin-4-yl)diphenylmethanol (B10, B14)

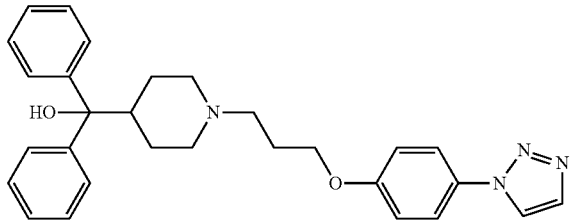 [SMILES: OC(c1ccccc1)(c1ccccc1)C1CCN(CCCOc2ccc(-n3ccnn3)cc2)CC1]

Step 1. Bromide intermediate (1-(3-(4-bromophenoxy)propyl)piperidin-4-yl)diphenylmethanol (A1) (100 mg, 0.21 mmol) was dissolved in EtOH:water (2:1, 3 mL) and treated with NaN$_3$ (34 mg, 0.53 mmol), CuI (5 mg), and sodium ascorbate (2.5 mg). The mixture was heated in a sealed tube for 1 h at 100° C. The reaction was cooled to rt and poured onto EtOAc (10 mL). The organic phase was washed with brine, dried over Na$_2$SO$_4$, and concentrated to dryness. RP-HPLC purification afforded the desired azide (45 mg, 46%): LC-MS (>98%) m/z=443.1 [M+H].

Step 2. Azide from step 1 (40 mg, 0.09 mmol), ethynyltrimethylsilane (11 mg, 0.11 mmol), K$_2$CO$_3$ (11 mg, 0.11 mmol), CuSO$_4$ (1.5 mg), and sodium ascorbate (1.0 mg) were stirred overnight in MeOH:H$_2$O (1:1, 10 mL). The mixture was poured onto H$_2$O, extracted with EtOAc (2×10 mL) and the organic layers combined and washed with brine. Concentration in vacuo and RP-HPLC purification afforded the title example triazole (22 mg, 52%): LC-MS (>98%) m/z=469.1 [M+H].

Example 6

Preparation of Diphenyl(1-(3-(4-(pyridin-4-yl)phenoxy)propyl)piperidin-4-yl)methanol (B35)

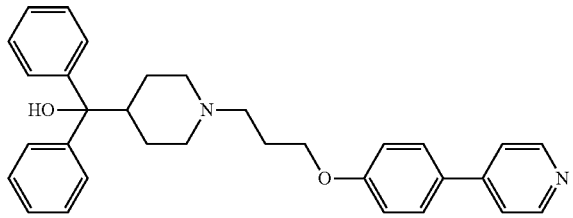 [SMILES: OC(c1ccccc1)(c1ccccc1)C1CCN(CCCOc2ccc(-c3ccncc3)cc2)CC1]

Bromide intermediate (1-(3-(4-bromophenoxy)propyl)piperidin-4-yl)diphenylmethanol (A1) (75 mg, 0.15 mmol), Pd(dppf)Cl$_2$ (15 mg), CsCO3 (150 mg), and pyridin-4-ylboronic acid (30 mg) was placed under an argon atmosphere in a microwave vial. Degassed THF (3 mL) and 0.1 mL of water was added via syringe and the mixture heated for 30 min. at 90° C. in a Biotage microwave reactor. The reaction was partitioned between EtOAc (10 mL) and water (3 mL) and the organic phase isolated. The organic phase was subsequently washed with brine, dried over Na2SO4, and concentrated to dryness. Purification by RP-HPLC afforded the title compound (30 mg, 41%): LC-MS (>98%) m/z=479.1 [M+H].

Example 7

Preparation of 4-(3-(4-((3-Fluorophenyl)(hydroxy)(pyridin-2-yl)methyl)piperidin-1-yl)propoxy)benzonitrile (B75)

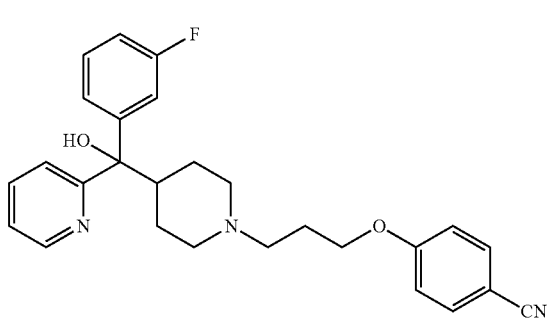 [SMILES: N#Cc1ccc(OCCCN2CCC(C(O)(c3cccc(F)c3)c3ccccn3)CC2)cc1]

Step 1. (1-(3-Chloropropyl)piperidin-4-yl)(pyridin-2-yl)methanone. To a solution of piperidin-4-yl(pyridin-2-yl)methanone (791 mg, 2.72 mmol) in dry DMF (9.1 mL) was added potassium carbonate (1.13 g, 8.16 mmol) followed by 1-bromo-3-chloropropane (514 mg, 3.26 mmol). Mixture was warmed to 50° C. and stirred for 4 h. The reaction was quenched with H$_2$O and extracted three times with EtOAc. The organic layers were combined and washed with sat. aqueous NaCl, then dried over Na$_2$SO$_4$ and filtered. Concentration in vacuo provided the crude product which was purified by flash chromatography (9:1 CH$_2$Cl$_2$/MeOH) to yield the title product in 790 mg (83%) as a light yellow oil: $^1$H NMR (400 MHz, CDCl$_3$) δ 8.66 (1H, d, J=4.4 Hz), 8.01 (1H, d, J=8.3 Hz), 7.82 (1H, t, J=7.8 Hz), 7.44 (1H, m), 3.83 (1H, m), 3.59 (2H, t, J=6.5 Hz), 2.95 (2H, d, J=11.2 Hz), 2.50 (2H, t, J=7.2 Hz), 2.16 (2H, m), 1.94 (4H, m), 1.77 (2H, m); $^{13}$C NMR (100.6 MHz, CDCl$_3$) δ 203.7, 152.7, 148.8, 136.9, 126.9, 122.4, 55.7, 53.2, 43.3, 42.2, 30.0, 28.1; HRMS (ES+, M+H) calcd for C$_{14}$H$_{20}$N$_2$OCl: 267.1264. found: 267.1263

Step 2. A solution of (1-(3-chloropropyl)piperidin-4-yl)(pyridin-2-yl)methanone (100 mg, 0.35 mmol) in THF (1.41 mL) was cooled to 0° C. To this was added 3-Fluorophenylmagnesium bromide (1.0 M in THF) dropwise with stirring. The solution was then slowly warmed to ambient temperature, and stirring continued for 2 h, at which point starting material was consumed by TLC analysis. The reaction was quenched with sat. aqueous NH$_4$Cl and extracted with EtOAc. The organic layers were combined and dried over Na$_2$SO$_4$ Solution was then transferred to a round-bottom flask, concentrated in vacuo to remove solvent, and then dissolved in DMF (1.0 mL). K$_2$CO$_3$ (76 mg, 0.55 mmol) was added, followed by 4-hydroxybenzonitrile (131 mg, 1.10 mmol). Mixture was warmed to 50° C. and stirred for 6 h. The reaction mixture was quenched with H₂O and extracted with EtOAc. The organic layers were combined and washed with sat. aqueous NaCl and dried over Na₂SO₄. Concentration in vacuo provided the crude product, which was purified by reverse-phase HPLC chromatography to provide the desired product as an off-white powder in 106 mg (65%). Chiral Separation: Semi-preparative purifications were carried out via stacked injections on a Waters Investigator SFC using a 10×250 mm Chiral Technologies CHIRALPAK ID column heated to 40° C. The eluent was 50% IPA (0.1% DEA) in CO₂ at a flow rate of 15 mL/minute. Backpressure was maintained at 100 bar. The first eluting peak (B78), retention time=3.09 min. The second eluting peak (B77), retention time=3.79 min. Racemic mixture ¹H NMR (500 MHz, CDCl₃) δ 8.85 (1H, d, J=6 Hz), 8.43 (1H, d, J=7.4 Hz), 8.37 (1H, t, J=7.4 Hz), 7.79 (1H, t, J=6.6 Hz), 7.59 (4H, m), 7.37 (1H, dd, J=16, 8 Hz), 6.96 (3H, m), 4.33 (1H, br s), 4.01 (2H, t, J=6 Hz), 3.59 (3H, m), 3.25 (2H, m), 3.07 (1H, m), 2.58 (1H, m), 2.44 (3H, m), 1.72 (1H, d, J=14 Hz), 1.59 (1H, d, J=14 Hz); ¹³C NMR (125.8 MHz, CDCl₃) δ 162.8 (d, $J_{CF}$=247 Hz), 162.2, 161.9, 148.4 (d, $J_{CF}$=6.2 Hz), 147.4, 137.4, 134.1, 129.8 (d, $J_{CF}$=8.1 Hz), 122.4, 121.5, 120.4, 119.4, 115.3, 113.9, 113.7, 113.5, 113.3, 104.0, 78.6, 66.7, 54.9, 54.0, 26.5, 25.6, 25.3; HRMS (ES+, M+H) calcd for $C_{27}H_{29}N_3O_2F$: 446.2244. found: 446.2248

Example 8

Preparation of 4-(3-(4-(Cyclopentyl(hydroxy)(pyridin-2-yl)methyl)piperidin-1-yl)propoxy)benzonitrile (B58)

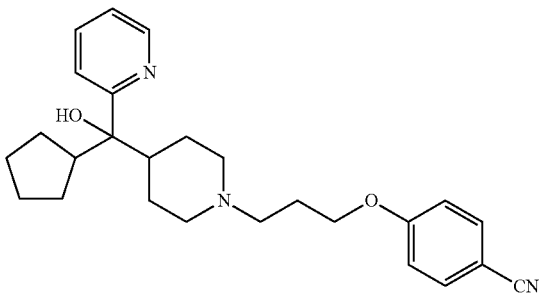 [SMILES: N#Cc1ccc(OCCCN2CCC(C(O)(c3ccccn3)C3CCCC3)CC2)cc1]

Step 1. 4-(3-(4-(Cyclopentanecarbonyl)piperidin-1-yl)propoxy)benzonitrile. Cyclopentyl(piperidin-4-yl)methanone (2.70 g, 10.0 mmol) was combined with K₂CO₃ (6.9 g, 50.0 mmol) in DMF (40.0 mL), followed by 1-bromo-3-chloropropane (1.55 g, 10.0 mmol). The reaction progress was monitored by LC-MS and upon completion of the reaction 4-cyanophenol (1.3 g, 11.0 mmol) was added and the reaction allowed to stir overnight. The mixture was poured onto water and extracted with EtOAc, washed with brine and dried over Na₂SO₄. The volatiles were removed under reduced pressure and the crude mixture purified on silica gel (9:1 CH₂Cl₂/MeOH) to provide 4-(3-(4-(cyclopentanecarbonyl)piperidin-1-yl)propoxy) benzonitrile in 2.71 g (78%) as a light yellow oil: ¹H NMR (600 MHz, CDCl₃) δ 7.56 (2H, d, J=9.0 Hz), 6.93 (2H, d, J=9.0 Hz), 4.05 (2H, t, J=6.5 Hz), 3.00 (1H, quintet, J=7.7 Hz), 2.94 (2H, m), 2.49 (2H, t, J=7.1 Hz), 2.42 (1H, m), 1.99 (4H, m), 1.79 (4H, m), 1.68 (6H, m), 1.56 (2H, m); ¹³C NMR (150.9 MHz, CDCl₃) δ 215.7, 162.5, 134.1, 119.4, 115.3, 103.9, 66.8, 55.1, 53.4, 49.4, 48.2, 29.5, 28.1, 26.7, 26.2; HRMS (ES+, M+H) calcd for $C_{21}H_{29}N_2O_2$: 341.2229. found: 341.2228

Step 2. 4-(3-(4-(cyclopentanecarbonyl)piperidin-1-yl)propoxy)benzonitrile (30 mg, 0.09 mmol) was dissolved in THF (0.7 mL). 2-Pyridylmagnesium bromide (0.25 M) was added dropwise (2.0 equiv) to the solution with stirring. Reaction was then warmed to 50° C., and stirring was continued for 2 h. Reaction was quenched with sat. aqueous NH₄Cl, and extracted with EtOAc. The combined organic fractions were washed with saturated NaCl and dried over Na₂SO₄. Concentration in vacuo provided the crude product, which was purified by flash column chromatography (9:1 CH₂Cl₂/MeOH) to provide the desired product (13 mg, 35%). ¹H NMR (400 MHz, CDCl₃) δ 8.52 (1H, d, J=5 Hz), 7.70 (2H, t, J=8 Hz), 7.57 (2H, d, J=8 Hz), 7.31 (1H, d, J=8 Hz), 7.21 (1H, dd, J=8, 5 Hz), 6.92 (2H, d, J=8 Hz), 5.72 (1H, br s), 4.03 (2H, t, J=6 Hz), 3.03 (1H, m), 2.56 (3H, m), 2.09-1.75 (7H, m), 1.65 (2H, m), 1.49 (4H, m), 1.15 (2H, m), 0.76 (1H, m); ¹³C NMR (125.8 MHz, CDCl₃) δ 162.2, 161.5, 147.0, 136.6, 134.1, 122.2, 121.1, 119.3, 115.3, 104.1, 78.1, 66.6, 55.1, 54.3, 54.2, 45.8, 45.4, 29.8, 27.1, 26.5, 26.1, 25.7; HRMS (ES+, M+H) calcd for $C_{26}H_{34}N_3O_2$: 420.2651. found: 420.2650

Example 9

Preparation of 4-(3-(4-(Cyclopentyl(hydroxy)(pyridin-2-yl)methyl)piperidin-1-yl)propoxy)benzenesulfonamide (B67)

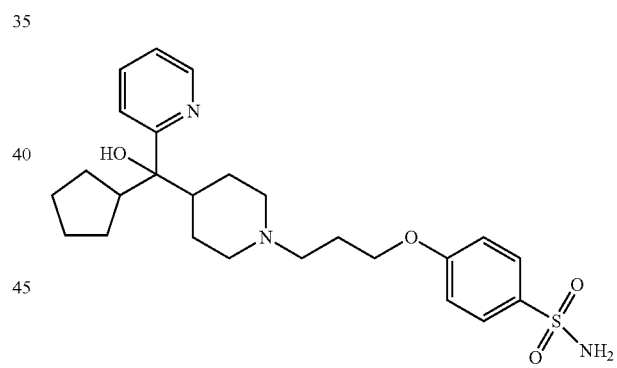

Step 1. (1-Benzylpiperidin-4-yl)(cyclopentyl)(pyridin-2-yl) methanol. 2-Bromopyridine (873 mg, 5.54 mmol), was dissolved in THF (30 mL), and cooled to −78° C. To this solution was added n-butyllithium (2.2 mL, 2.5 M in hexanes, 5.53 mmol) dropwise with stirring. Stirring was continued for 20 min. (1-Benzylpiperidin-4-yl)(cyclopentyl) methanone (500 mg, 1.84 mmol) dissolved in THF (2.0 mL), was added dropwise to stirring solution of pyridin-2-yllithium at −78° C. The mixture was stirred for 20 min. and then slowly warmed to room temperature. Reaction was stirred for 2 h, then quenched with sat. aqueous NH₄Cl. The mixture was extracted with EtOAc, and the organic layers combined and washed with sat. aqueous NaCl and dried over Na₂SO₄. Concentration in vacuo provided the crude product, which was purified by flash column chromatography (9:1 CH₂Cl₂/MeOH) to provide the desired product as a white solid in 599 mg (93%): ¹H NMR (400 MHz, CDCl₃) δ 8.51 (1H, d, J=4.7 Hz), 7.66 (1H, t, J=8.1 Hz), 7.30-7.17 (7H, m), 5.66 (1H, br s), 3.45 (2H, d, J=2.0 Hz), 2.90 (2H, m), 2.62 (1H, quintet, J=8.5 Hz), 1.97-1.61 (8H, m), 1.47 (4H, m), 1.14 (2H, m), 0.69 (1H, m); $^{13}$C NMR (125.8 MHz, CDCl$_3$) δ 162.1, 146.9, 138.5, 136.3, 129.3, 128.2, 127.0, 121.9, 121.2, 78.3, 63.5, 54.5, 54.3, 46.0, 45.8, 27.9, 27.1, 26.6, 26.5, 26.2, 25.7; HRMS (ES+, M+H) calcd for C$_{23}$H$_{31}$N$_2$O: 351.2436. found: 351.2433

Step 2. In a Parr vessel, (1-benzylpiperidin-4-yl)(cyclopentyl)(pyridin-2-yl)methanol (500 mg, 1.84 mmol) was dissolved in EtOH (10 mL). The solution was degassed by bubbling Argon through the solution for 10 min. Pd(OH)$_2$ was then added and the vessel was quickly inserted into the Parr Shaker apparatus. The system was purged with H$_2$ three times, and H$_2$ pressure was then set to 70 psi. The vessel was heated to 50° C., and shaken for 12-24 h. When the reaction progress was complete by LCMS, the mixture was filtered through a celite pad and washed with EtOH. The filtrate was concentrated in vacuo to yield the crude product, which was carried forward to the next step.

Step 3. Cyclopentyl(piperidin-4-yl)(pyridin-2-yl)methanol (30 mg, 0.12 mmol) from above step 2 was dissolved in DMF (1.0 mL). 4-(3-chloropropoxy)benzenesulfonamide (29 mg, 0.12 mmol) and K$_2$CO$_3$ (32 mg, 0.23 mmol) were added and reaction was warmed to 50° C. Stirring was continued overnight. The reaction mixture was quenched with aqueous NH$_4$Cl. The mixture was extracted with EtOAc, and the organic layers combined and washed with sat. aqueous NaCl and dried over Na$_2$SO$_4$. Concentration in vacuo provided the crude product, which was purified by RP-HPLC to provide the desired product as a white solid in 23 mg (42%): $^1$H NMR (500 MHz, CDCl$_3$) δ 8.45 (1H, d, J=4.7 Hz), 7.80 (2H, d, J=8.4 Hz), 7.65 (1H, t, J=7.8 Hz), 7.27 (1H, d, J=7.8 Hz), 7.17 (1H, t, J=6.1 Hz), 6.90 (2H, d, J=7.8 Hz), 5.66 (1H, br s), 5.06 (2H, br s), 3.98 (2H, t, J=6.4 Hz), 2.98 (1H, d, J=10.2 Hz), 2.91 (1H, d, J=10.2 Hz), 2.58 (1H, m), 2.44 (2H, m), 1.96-1.69 (8H, m), 1.60-1.42 (6H, m), 1.12 (2H, m), 0.69 (1H, m); $^{13}$C NMR (125.8 MHz, CDCl$_3$) δ 162.4, 161.8, 147.0, 136.5, 133.8, 128.6, 122.0, 121.2, 114.8, 78.3, 66.9, 55.2, 54.5, 54.4, 45.8, 45.7, 27.6, 27.1, 26.6, 26.5, 26.4, 26.1, 25.7; HRMS (ES+, M+H) calcd for C$_{25}$H$_{36}$N$_3$O$_4$S: 474.2427. found: 474.2430.

Example 10

4-(3-(4-((3-Fluorophenyl)(hydroxy)(pyridin-2-yl)methyl)piperidin-1-yl)-2-hydroxypropoxy)benzonitrile (B86)

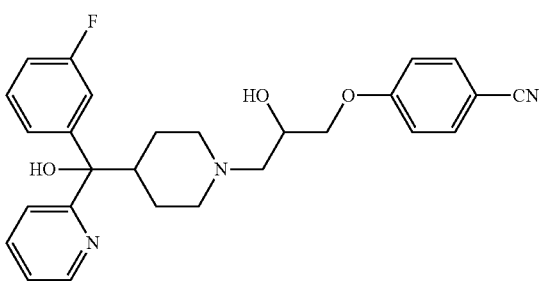 [SMILES: N#Cc1ccc(OCC(O)CN2CCC(C(O)(c3cccc(F)c3)c3ccccn3)CC2)cc1]

Step 1. 4-(oxiran-2-ylmethoxy)benzonitrile. A mixture of 4-hydroxybenzonitrile (2.00 g, 14.47 mmol), K$_2$CO$_3$ (2.40 g, 17.37 mmol), and epichlorohydrin (6.694 g, 5.673 mL, 72.36 mmol) was added to a sealed vial and stirred at 120° C. for 5 hours. After completion of reaction as determined by TLC, the solid was filtered, filtrate was diluted with water, and extracted three times with EtOAc. Organic layers were combined, washed with saturated sodium chloride solution, dried over Na$_2$SO$_4$, and concentrated in vacuo. Flash column chromatography (1:1 EtOAc/hexanes) provided 4-(oxiran-2-ylmethoxy)benzonitrile as a white crystalline solid in 1.9 g (76%). $^1$H NMR (400 MHz, CDCl$_3$) δ 7.58 (2H, d, J=9.0 Hz); 6.98 (2H, d, J=9.0 Hz); 4.32 (1H, dd, J=2.7, 11.1 Hz); 3.96 (1H, dd, J=5.9, 11.1 Hz); 3.36 (1H, m); 2.93 (1H, t, J=4.3 Hz); 2.76 (1H, dd, J=2.6, 4.75 Hz); LC-MS (>98%) m/z=176.0 [M+H].

Step 2. Tert-butyl 4-((3-fluorophenyl)(hydroxy)(pyridin-2-yl)methyl)piperidine-1-carboxylate (0.47 g, 1.22 mmol) was dissolved in HCl/dioxanes (7.6 mL, 4 M) at 0° C., and stirred at ambient room temperature for 1 hour. Product was concentrated in vacuo to yield (3-fluorophenyl)(piperidin-4-yl)(pyridin-2-yl)methanol as the HCl salt. The solvent was evaporated and the crude oil was neutralized with saturated NaHCO$_3$ and extracted three times with EtOAc. The organic layers were combined and washed with saturated sodium chloride, dried of Na$_2$SO$_4$, and concentrated in vacuo. The free base (3-fluorophenyl)(piperidin-4-yl)(pyridin-2-yl)methanol was used directly in the following step.

Step 3. (3-fluorophenyl)(piperidin-4-yl)(pyridin-2-yl)methanol from step 2 was dissolved in CH$_3$CN, and K$_2$CO$_3$ was added at room temperature. 4-(Oxiran-2-ylmethoxy)benzonitrile from step 1 was then added at room temperature and stirred for 16 h. The reaction mixture was filtered and eluted with EtOAc, and the filtrate was concentrated in vacuo to give a white solid, which was purified by flash column chromatography (1:1 EtOAc/hexanes) to give the desired product 4-(3-(4-((3-fluorophenyl)(hydroxy)(pyridin-2-yl)methyl)piperidin-1-yl)-2-hydroxypropoxy)benzonitrile as a white powder solid in 300 mg (54%). $^1$H NMR (400 MHz, CDCl$_3$) δ 8.49 (1H, d, J=4.7 Hz); 7.69 (1H, dt, J=1.7, 7.8 Hz); 7.57 (2H, m); 7.45 (1H, d, J=8.0 Hz); 7.37 (2H, m); 7.29 (1H, m); 7.19 (1H, dd, J=4.7, 7.2 Hz); 6.96 (2H, d, J=8.8 Hz); 6.89 (1H, dt, J=2.4, 8.3 Hz); 6.15 (1H, br s); 4.07 (1H, m); 4.00 (2H, d, J=5.0 Hz); 3.07 (1H, m); 2.87 (1H, m); 2.51 (2H, m); 2.37 (2H, m); 2.04 (2H, m); 1.68 (2H, m); 1.50 (1H, d, J=13.6 Hz); 1.25 (1H, dd, J=6.8, 9.5 Hz); 1.02 (1H, m); LC-MS (>98%) m/z=462.2 [M+H].

Example 11

Characterization of Exemplary Compounds

The compounds in Table 1 were synthesized with methods identical or analogous to those described herein. The Synthetic Example indicated in Table I refers to the compound identified above and corresponding synthetic method described therein. The requisite starting materials were commercially available, described in the literature, or readily synthesized by one skilled in the art of organic synthesis. The mass spectrometry data were obtained using either General LC-MS Method 1 or General LC-MS Method 2 as described above. LC-MS [M+H]$^+$ means the protonated mass of the free base of the compound.

TABLE 1

Exemplary compounds

| No. | Compound | LC-MS [M + H] | Synthetic Example/ Scheme* |
|---|---|---|---|
| B1 | | 427.2 | Ex. 2/Scheme 2 |
| B2 | | 443.2 | Scheme 1 |
| B3 | | 470.2 | Ex. 2/Scheme 2 |
| B4 | | 486.2 | Ex. 2/Scheme 2 |
| B5 | | 436.2 | Ex. 2/Scheme 2 |
| B6 | | 445.2 | Ex. 2/Scheme 2 |

TABLE 1-continued

Exemplary compounds

| No. | Compound | LC-MS [M + H] | Synthetic Example/ Scheme* |
|---|---|---|---|
| B7 | | 407.3 | Ex. 4/Scheme 4 |
| B8 | | 391.2 | Ex. 4/Scheme 4 |
| B9 | | 480.1 | Intermediate A1 |
| B10 | | 469.3 | Ex. 5/Scheme 7 |
| B11 | | 419.3 | Ex. 3/Scheme 3 |

TABLE 1-continued
Exemplary compounds
| No. | Compound | LC-MS [M + H] | Synthetic Example/ Scheme* |
|---|---|---|---|
| B12 | 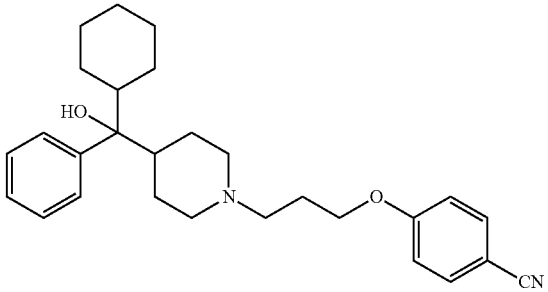 | 433.3 | Ex. 3/Scheme 3 |
| B13 | 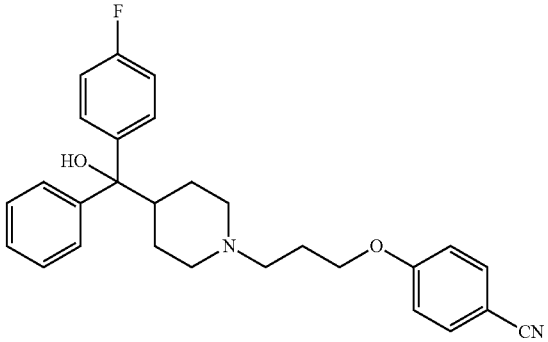 | 445.2 | Ex. 3/Scheme 3 |
| B14 | 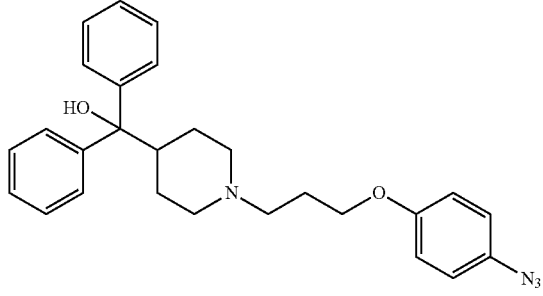 | 443.2 | Ex. 5/Scheme 7 |
| B15 | 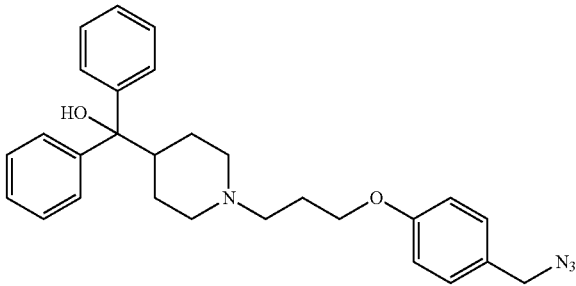 | 431.3 | Ex. 2/Scheme 2, 5 |

TABLE 1-continued

Exemplary compounds

| No. | Compound | LC-MS [M + H] | Synthetic Example/ Scheme* |
|---|---|---|---|
| B16 | | 460.2 | Ex. 2/Scheme 2 |
| B17 | | 433.3 | Ex. 3/Scheme 2 |
| B18 | | 433.3 | Ex. 3/Scheme 2 |
| B19 | | 419.3 | Ex. 3/Scheme 3 |
| B20 | | 419.3 | Ex. 3/Scheme 3 |

TABLE 1-continued

Exemplary compounds

| No. | Compound | LC-MS [M + H] | Synthetic Example/ Scheme* |
|---|---|---|---|
| B21 | | 393.2 | Ex. 3/Scheme 2-3 |
| B22 | | 405.2 | Ex. 3/Scheme 2-3 |
| B23 | | 419.2 | Ex. 2/Scheme 2 |
| B24 | | 481.2 | Ex. 2/Scheme 2 |
| B25 | | 509.2 | Scheme 6 |

TABLE 1-continued
Exemplary compounds
| No. | Compound | LC-MS [M + H] | Synthetic Example/ Scheme* |
|---|---|---|---|
| B26 | 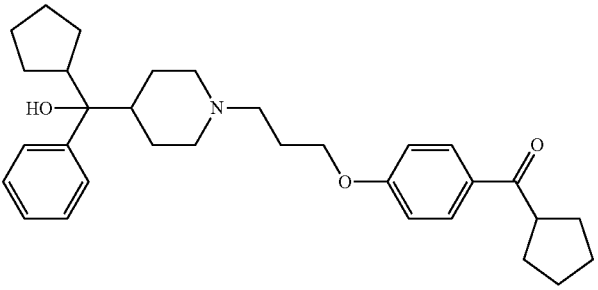 | 490.3 | Ex. 3 |
| B27 | 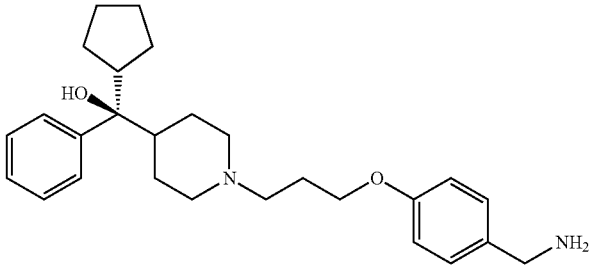 | 423.3 | Ex. 3/Scheme 2, 5 |
| B28 | 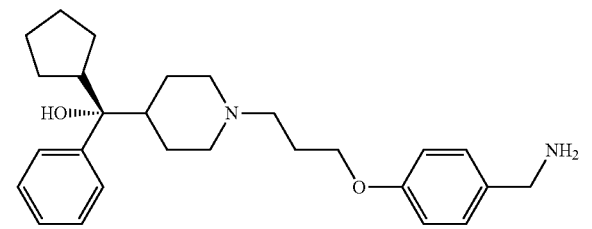 | 423.3 | Ex. 3/Scheme 2, 5 |
| B29 | 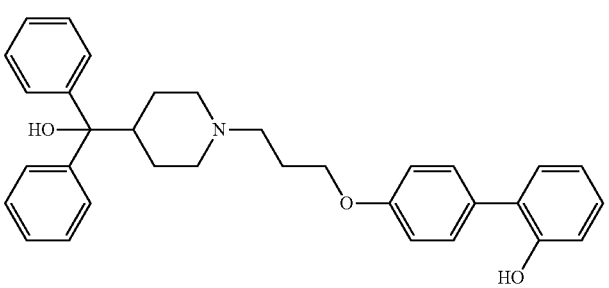 | 494.3 | Ex. 6/Scheme 7 |
| B30 | 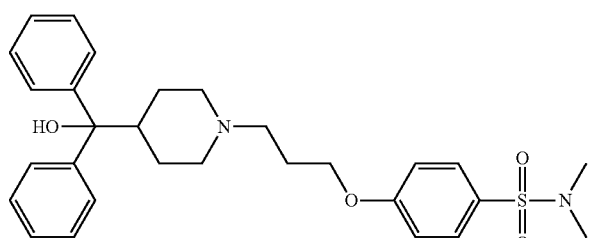 | 509.2 | Ex. 2/Scheme 2 |

TABLE 1-continued

Exemplary compounds

| No. | Compound | LC-MS [M + H] | Synthetic Example/ Scheme* |
|---|---|---|---|
| B31 | | 411.3 | Ex. 2/Scheme 2 |
| B32 | | 417.2 | Scheme 2 |
| B33 | | 480.2 | Ex. 2/Scheme 2 |
| B34 | | 421.3 | Scheme 2, 5 |
| B35 | | 479.3 | Ex. 6 |
| B36 | | 479.3 | Ex. 6/Scheme 7 |

TABLE 1-continued

Exemplary compounds

| No. | Compound | LC-MS [M + H] | Synthetic Example/ Scheme* |
|---|---|---|---|
| B37 | | 403.2 | Ex. 2/Scheme 2 |
| B38 | | 473.3 | Ex. 2/Scheme 2, 5 |
| B39 | | 480.3 | Ex. 6/Scheme 7 |
| B40 | | 441.2 | Ex. 2/Scheme 2 |
| B41 | | 435.3 | Ex. 3/Scheme 1, 2 |
| B42 | | 426.2 | Ex. 2/Scheme 2 |

TABLE 1-continued
Exemplary compounds
| No. | Compound | LC-MS [M + H] | Synthetic Example/ Scheme* |
|---|---|---|---|
| B43 | 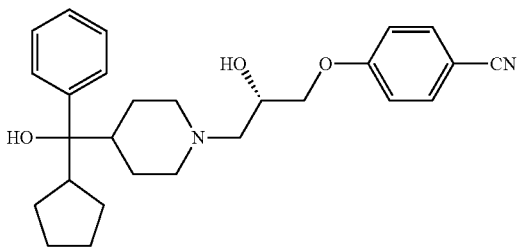 | 435.3 | Ex. 3/Scheme 1, 2 |
| B44 | 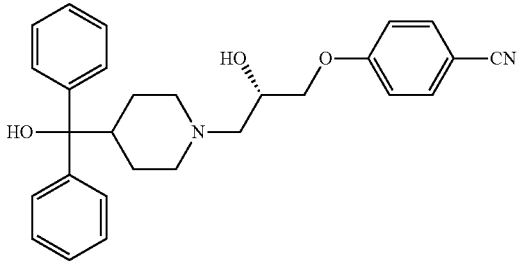 | 443.2 | Ex. 2/Scheme 1, 2 |
| B45 | 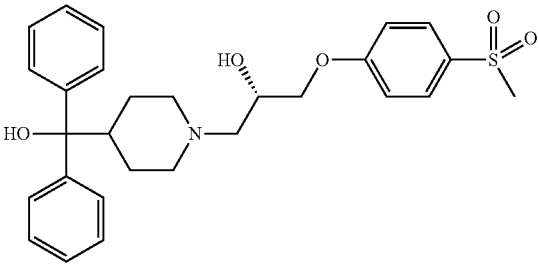 | 496.2 | Ex. 2/Scheme 1, 2 |
| B46 | 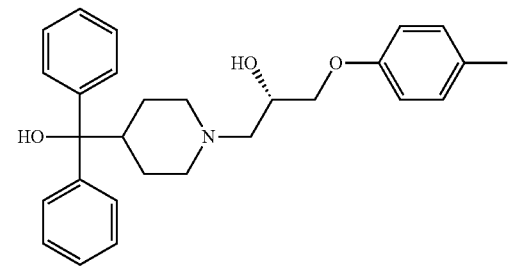 | 432.2 | Ex. 2/Scheme 1, 2 |
| B47 | 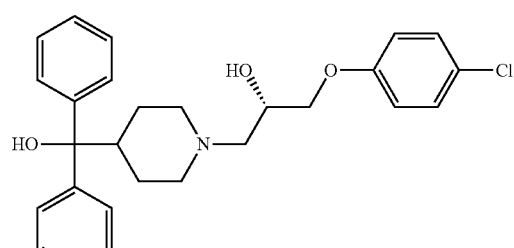 | 452.2 | Ex. 2/Scheme 1, 2 |

TABLE 1-continued

Exemplary compounds

| No. | Compound | LC-MS [M + H] | Synthetic Example/ Scheme* |
|---|---|---|---|
| B48 | | 502.2 | Ex. 2/Scheme 1, 2 |
| B49 | | 459.2 | Ex. 2/Scheme 1, 2 |
| B50 | | 461.2 | Ex. 2/Scheme 1, 2 |
| B51 | | 461.2 | Ex. 2/Scheme 1, 2 |
| B52 | | 495.2 | Ex. 2/Scheme 2 |

TABLE 1-continued

Exemplary compounds

| No. | Compound | LC-MS [M + H] | Synthetic Example/ Scheme* |
|---|---|---|---|
| B53 | | 459.2 | Ex. 2/Scheme 2 |
| B54 | | 455.3 | Ex. 2/Scheme 2 (alkylation with EtI) |
| B55 | | 441.2 | Ex. 2/Scheme 2 (alkylation with MeI) |
| B56 | | 498.3 | Ex. 2/Scheme 2 (alkylation with ClCH$_2$CH$_2$N(CH$_3$)$_2$ HCL) |
| B57 | | 450.3 | Scheme 4 |

TABLE 1-continued

Exemplary compounds

| No. | Compound | LC-MS [M + H] | Synthetic Example/ Scheme* |
|---|---|---|---|
| B58 | | 420.3 | Scheme 4 |
| B59 | | 431.3 | Scheme 2 |
| B60 | | 420.3 | Scheme 4 |
| B61 | | 420.3 | Ex. 3/Scheme 2 |
| B62 | | 433.3 | Ex. 2/Scheme 2 (alkylation with MeI) |
| B63 | | 426.3 | Scheme 3 (over reduction of pyridine) |

TABLE 1-continued
Exemplary compounds
| No. | Compound | LC-MS [M + H] | Synthetic Example/ Scheme* |
|---|---|---|---|
| B64 | 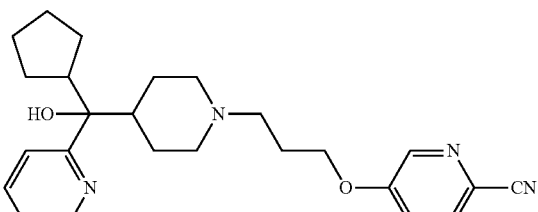 | 421.3 | Ex. 3/Scheme 3 |
| B65 | 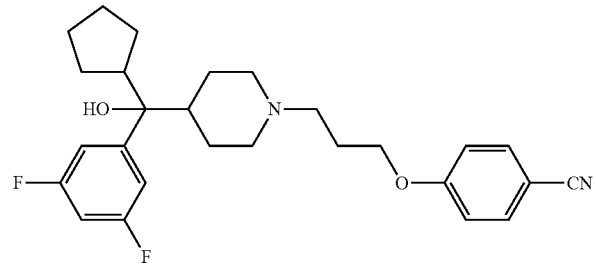 | 455.2 | Ex. 3/Scheme 3 |
| B66 | 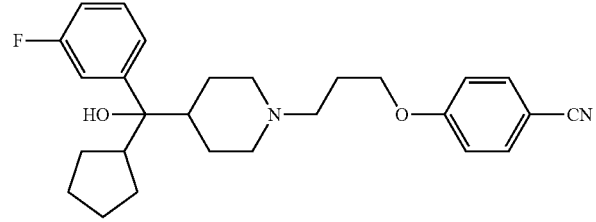 | 437.3 | Ex. 3/Scheme 3 |
| B67 | 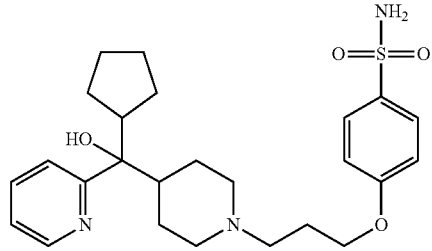 | 474.2 | Ex. 8/Scheme 2 |
| B68 | 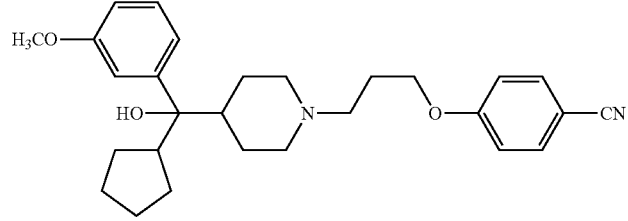 | 449.3 | Ex. 3/Scheme 3 |
| B69 | 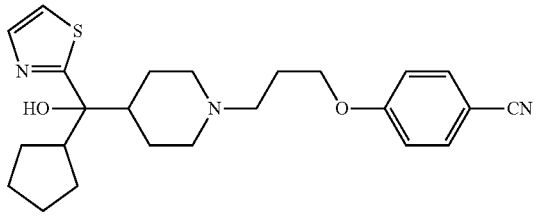 | 426.2 | Ex. 3/Scheme 3 |

TABLE 1-continued
Exemplary compounds
| No. | Compound | LC-MS [M + H] | Synthetic Example/ Scheme* |
|---|---|---|---|
| B70 | 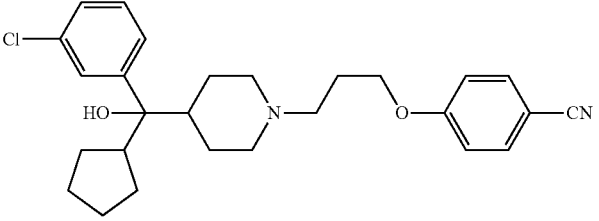 | 453.2 | Ex. 3/Scheme 3 |
| B71 | 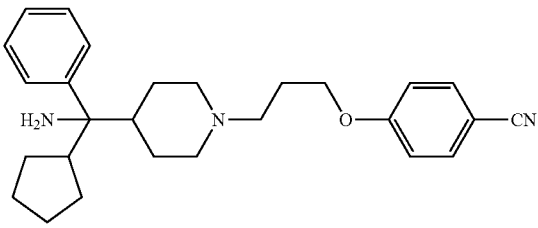 | 418.3 | Ex. 4/Scheme 8 |
| B72 | 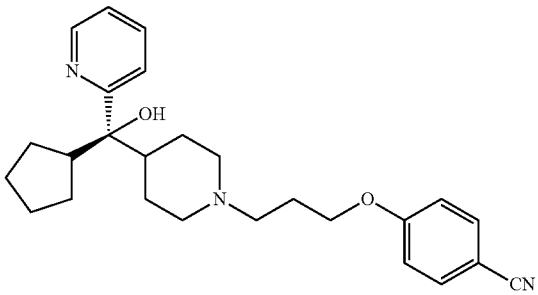 | 420.3 | Ex. 8/Scheme 2 |
| B73 | 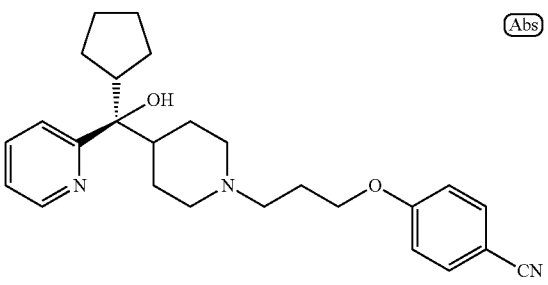 | 420.3 | Ex. 8/Scheme 2 |
| B74 | 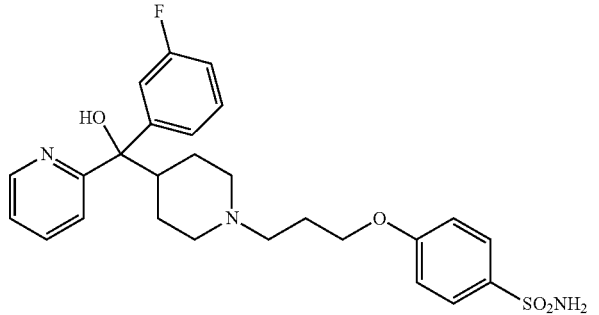 | 500.1 | Ex. 7/Scheme 9 |

TABLE 1-continued

Exemplary compounds

| No. | Compound | LC-MS [M + H] | Synthetic Example/ Scheme* |
|---|---|---|---|
| B75 | | 446.1 | Ex. 7/Scheme 9 |
| B76 (NC) | | 351.2 | Ex. 2/Scheme 2 |
| B77 | second peak SFC | 445.54 | Ex. 7/Scheme 9 |
| B78 | first peak SFC | 445.54 | Ex. 7/Scheme 9 |
| B79 | first peak SFC | 417.60 | Ex. 4/Scheme 8 |

TABLE 1-continued
Exemplary compounds
| No. | Compound | LC-MS [M + H] | Synthetic Example/ Scheme* |
|---|---|---|---|
| B80 | 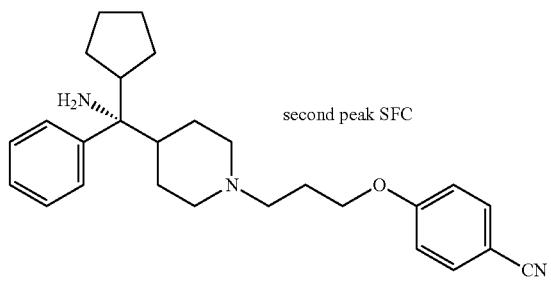 second peak SFC | 417.60 | Ex. 4/Scheme 8 |
| B81 | 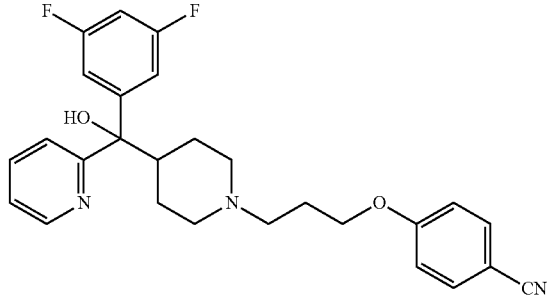 | 463.53 | Ex. 7/Scheme 9 |
| B82 | 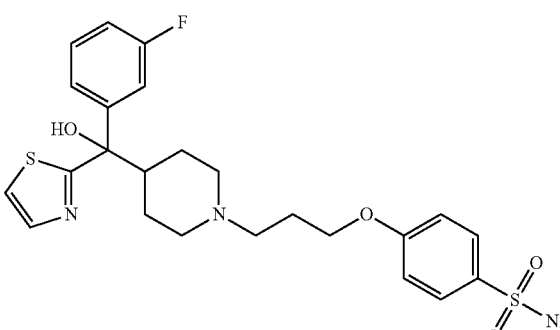 | 505.62 | Ex. 7/Scheme 9 |
| B83 | 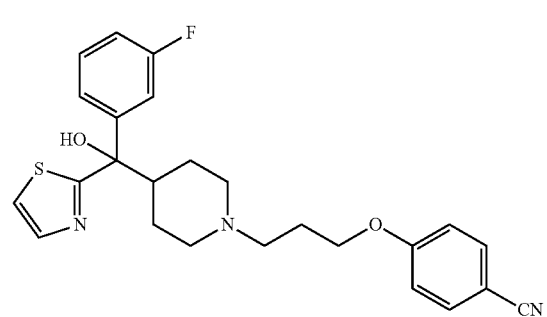 | 451.56 | Ex. 7/Scheme 9 |

TABLE 1-continued

Exemplary compounds

| No. | Compound | LC-MS [M + H] | Synthetic Example/ Scheme* |
|---|---|---|---|
| B84 | 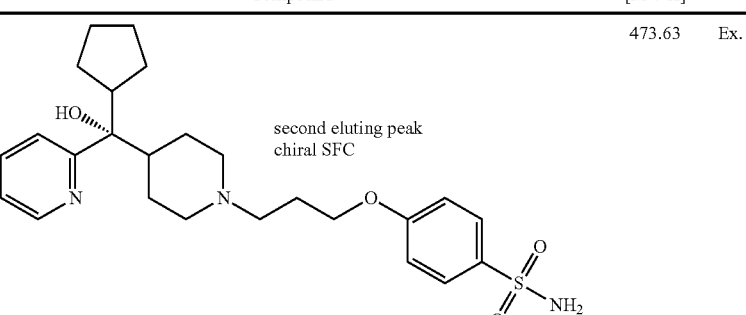 second eluting peak chiral SFC | 473.63 | Ex. 4/Scheme 2 |
| B85 | 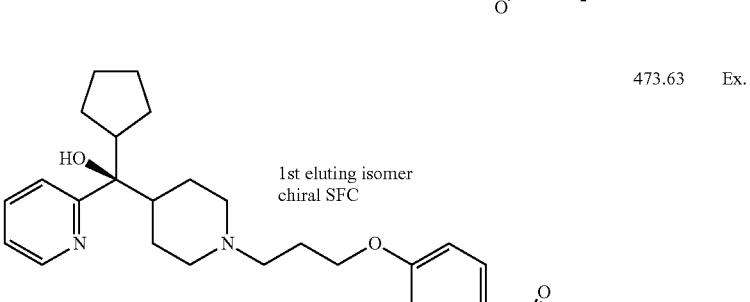 1st eluting isomer chiral SFC | 473.63 | Ex. 4/Scheme 2 |
| B86 | 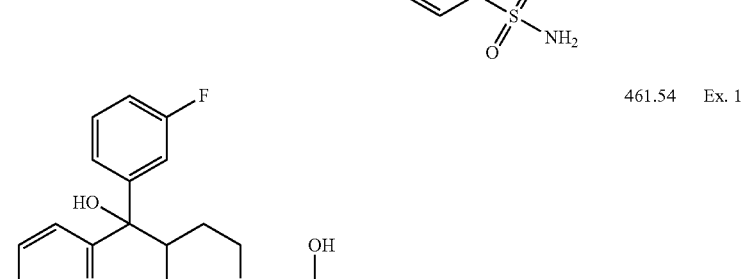 | 461.54 | Ex. 10/Scheme 10 |

Example 8

Assays for Assessing Menin-MLL Inhibition

Fluorescence Polarization Assay. Assays effective in monitoring the inhibition of the MLL binding to menin were developed during experiments performed during the development of embodiments of the present invention. A fluorescein-labeled 12-amino acid peptide derived from MLL containing the high affinity menin binding motif was produced (Yokoyama et al., Cell., 2005.123(2): p. 207-18., herein incorporated by reference in its entirety). Upon binding of the peptide (1.7 kDa) to the much larger menin (67 kDa), the rotational correlation time of the fluorophore (peptide labeled with fluorescein at N-terminus) changes significantly, resulting in a substantial increase in the measured fluorescence polarization and fluorescence anisotropy (excitation at 500 nm, emission at 525 nm). The fluorescence polarization (FP) assay was utilized to determine the $K_d$ for the binding of menin and the MLL peptide using a serial dilution of menin and 50 nM fluorescein-labeled MLL peptide. The titration curve demonstrates nanomolar affinity ($K_d$=56 nM) for the menin-MLL interaction.

The effectiveness of compounds ($IC_{50}$ values) in inhibiting the menin-MLL interaction was determined in the FP competition experiments. Compounds that inhibit the interaction decrease the fluorescence anisotropy which is being used as a read-out for compound screening and for $IC_{50}$ determination. For validation of the FP assay, a control competition experiment with unlabeled MLL peptide (no fluorescein attached) was performed. The competitive displacement of the fluorescein-labeled MLL peptide from menin by unlabeled MLL peptide was monitored. Using this assay, the $IC_{50}$ value for the MLL peptide with menin: $IC_{50}$=0.23 µM. In some embodiments of the present invention, the same competition FP assay is used for screening compounds targeting menin and inhibiting the menin-MLL interaction.

Biological activity of menin-MLL inhibitors is demonstrated in Example 9. The $IC_{50}$ values shown were measured using the above fluorescence polarization (FP) assay.

Example 9

In vitro Activity of Representative Menin-MLL Inhibitors

| Example | IC$_{50}$ (M) |
|---|---|
| B1 | 1.67E−05 |
| B2 | 1.40E−05 |
| B3 | 5.20E−05 |
| B4 | 9.80E−05 |
| B5 | 9.60E−05 |
| B6 | 2.65E−05 |
| B7 | 1.53E−05 |
| B8 | 1.12E−05 |
| B9 | 7.87E−05 |
| B10 | 2.90E−05 |
| B11 | 8.83E−07 |
| B12 | 1.68E−06 |
| B13 | 7.75E−05 |
| B14 | 5.80E−05 |
| B15 | 7.60E−06 |
| B16 | 8.60E−05 |
| B17 | 5.70E−07 |
| B18 | 1.13E−06 |
| B19 | 3.36E−07 |
| B20 | 4.12E−07 |
| B21 | 4.05E−06 |
| B22 | 4.00E−06 |
| B23 | 3.10E−05 |
| B24 | 1.43E−05 |
| B25 | 4.00E−05 |
| B26 | 3.95E−06 |
| B27 | 1.39E−05 |
| B28 | 1.31E−05 |
| B29 | 8.30E−06 |
| B30 | 4.00E−05 |
| B31 | 1.40E−06 |
| B32 | 2.08E−06 |
| B33 | 5.85E−06 |
| B34 | 1.39E−05 |
| B35 | 3.06E−05 |
| B36 | 2.26E−05 |
| B37 | 2.50E−05 |
| B38 | 2.07E−05 |
| B39 | 8.30E−05 |
| B40 | 1.74E−05 |
| B41 | 1.15E−06 |
| B42 | 9.56E−06 |
| B43 | 9.48E−07 |
| B44 | 4.50E−05 |
| B45 | 2.10E−05 |
| B46 | 1.00E−04 |
| B47 | 4.00E−05 |
| B48 | 3.10E−05 |
| B49 | 7.08E−05 |
| B50 | 4.00E−05 |
| B51 | 1.50E−05 |
| B52 | 5.50E−05 |
| B53 | 3.16E−05 |
| B54 | 5.30E−06 |
| B55 | 5.30E−06 |
| B56 | 4.20E−06 |
| B57 | 7.50E−05 |
| B58 | 7.09E−07 |
| B59 | 1.13E−05 |
| B60 | 3.07E−07 |
| B61 | 8.94E−06 |
| B62 | 7.43E−07 |
| B63 | 2.80E−05 |
| B64 | 4.05E−06 |
| B65 | 4.37E−07 |
| B66 | 1.97E−07 |
| B67 | 1.15E−07 |
| B68 | 1.10E−06 |
| B69 | 2.42E−07 |
| B70 | 2.26E−07 |
| B71 | 8.00E−08 |
| B72 | 1.11E−06 |
| B73 | 2.59E−07 |
| B74 | 2.95E−07 |
| B75 | 2.25E−07 |
| B76 (NC) | 2.50E−04 |
| B77 | 9.00E−08 |
| B78 | 1.40E−06 |
| B79 | 5.60E−08 |
| B80 | 8.10E−08 |
| B81 | 9.00E−07 |
| B82 | 3.54E−07 |
| B83 | 4.07E−07 |
| B84 | 1.11E−06 |
| B85 | 2.59E−07 |
| B86 | 2.22E−07 |

REFERENCES

All references contained herein and/or listed below are herein incorporated by reference in their entireties.

Tomizawa, D., et al., *Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group.* Leukemia, 2007. 21(11): p. 2258-63.

Marschalek, R., *Mechanisms of leukemogenesis by MLL fusion proteins.* Br J Haematol, 2011. 152(2): p. 141-54.

Dimartino, J. F. and M. L. Cleary, *Mll rearrangements in haematological malignancies: lessons from clinical and biological studies.* Br J Haematol, 1999. 106(3): p. 614-26.

Pui, C. H., et al., *Clinical heterogeneity in childhood acute lymphoblastic leukemia with 11q23 rearrangements.* Leukemia, 2003.17(4): p. 700-6.

Tkachuk, D. C., S. Kohler, and M. L. Cleary, *Involvement of a homolog of Drosophila trithorax by 11q23 chromosomal translocations in acute leukemias.* Cell, 1992. 71(4): p. 691-700.

Milne, T. A., et al., *Leukemogenic MLL fusion proteins bind across a broad region of the Hox a9 locus, promoting transcription and multiple histone modifications.* Cancer Res, 2005. 65(24): p. 11367-74.

Nakamura, T., et al., *ALL-1 is a histone methyltransferase that assembles a supercomplex of proteins involved in transcriptional regulation.* Mol Cell, 2002. 10(5): p. 1119-28.

Yokoyama, A., et al., *Leukemia proto-oncoprotein MLL forms a SET1-like histone methyltransferase complex with menin to regulate Hox gene expression.* Mol Cell Biol, 2004. 24(13): p. 5639-49.

Milne, T. A., et al., *MLL targets SET domain methyltransferase activity to Hox gene promoters.* Mol Cell, 2002. 10(5): p. 1107-17.

Butler, L. H., et al., *The HRX proto-oncogene product is widely expressed in human tissues and localizes to nuclear structures.* Blood, 1997. 89(9): p. 3361-70.

Yu, B. D., et al., *MLL, a mammalian trithorax-group gene, functions as a transcriptional maintenance factor in morphogenesis.* Proc Natl Acad Sci USA, 1998. 95(18): p. 10632-6.

Caslini, C., et al., *Interaction of MLL amino terminal sequences with menin is required for transformation.* Cancer Res, 2007.67(15): p. 7275-83.

Yokoyama, A., et al., *The menin tumor suppressor protein is an essential oncogenic cofactor for MLL-associated leukemogenesis.* Cell, 2005. 123(2): p. 207-18.

Dorrance, A. M., et al., *Mll partial tandem duplication induces aberrant Hox expression in vivo via specific epigenetic alterations.* J Clin Invest, 2006. 116(10): p. 2707-16.

Poppe, B., et al., *Expression analyses identify MLL as a prominent target of 11q23 amplification and support an etiologic role for MLL gain of function in myeloid malignancies.* Blood, 2004. 103(1): p. 229-35.

Slany, R. K., *The molecular biology of mixed lineage leukemia.* Haematologica, 2009. 94(7): p. 984-93.

Tamai, H. and K. Inokuchi, *11q23/MLL acute leukemia: update of clinical aspects.* J Clin Exp Hematop, 2010. 50(2): p. 91-8.

Balgobind, B. V., et al., *The heterogeneity of pediatric MLL-rearranged acute myeloid leukemia.* Leukemia, 2011. 25(8): p. 1239-48.

Pigazzi, M., et al., *MLL partner genes drive distinct gene expression profiles and genomic alterations in pediatric acute myeloid leukemia: an AIEOP study.* Leukemia, 2011. 25(3): p. 560-3.

Chandrasekharappa, S. C., et al., *Positional cloning of the gene for multiple endocrine neoplasia-type 1.* Science, 1997.276(5311): p. 404-7.

Maillard, I. and J. L. Hess, *The role of menin in hematopoiesis.* Adv Exp Med Biol, 2009. 668: p. 51-7.

Maillard, I., et al., *Menin regulates the function of hematopoietic stem cells and lymphoid progenitors.* Blood, 2009. 113(8): p. 1661-9.

Thorsteinsdottir, U., et al., *Overexpression of the myeloid leukemia-associated Hoxa9 gene in bone marrow cells induces stem cell expansion.* Blood, 2002. 99(1): p. 121-9.

Takeda, A., C. Goolsby, and N. R. Yaseen, *NUP98-HOXA9 induces long-term proliferation and blocks differentiation of primary human CD34+ hematopoietic cells.* Cancer Res, 2006. 66(13): p. 6628-37.

Faber, J., et al., *HOXA9 is required for survival in human MLL-rearranged acute leukemias.* Blood, 2009. 113(11): p. 2375-85.

Fujino, T., et al., *Inhibition of myeloid differentiation by Hoxa9, Hoxb8, and Meis homeobox genes.* Exp Hematol, 2001. 29(7): p. 856-63.

Somervaille, T. C. and M. L. Cleary, *Identification and characterization of leukemia stem cells in murine MLL-AF9 acute myeloid leukemia.* Cancer Cell, 2006. 10(4): p. 257-68.

Wong, P., et al., *Meis1 is an essential and rate-limiting regulator of MLL leukemia stem cell potential.* Genes Dev, 2007.21(21): p. 2762-74.

Daigle, S. R., et al., *Selective killing of mixed lineage leukemia cells by a potent small-molecule DOT1L inhibitor.* Cancer Cell, 2011. 20(1): p. 53-65.

Chang, M. J., et al., *Histone H3 lysine 79 methyltransferase Dot1 is required for immortalization by MLL oncogenes.* Cancer Res, 2010. 70(24): p. 10234-42.

Nguyen, A. T., et al., *DOT1L, the H3K79 methyltransferase, is required for MLL-AF9-mediated leukemogenesis.* Blood, 2011.117(25): p. 6912-22.

What is claimed is:

1. A composition comprising a compound having the structure of formula I:

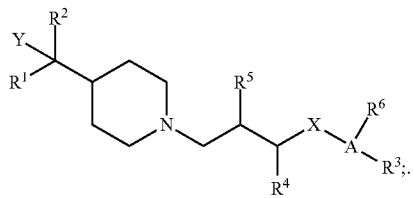

wherein Y is independently selected from OH, $OR^7$, $NH_2$, $NHR^7$, or $NR^{7a}R^{7b}$;

wherein $R^7$ selected from $C_{1-6}$-alkyl, monohalo-$C_{1-6}$-alkyl, polyhalo-$C_{1-6}$-alkyl, ($C_{1-4}$-alkyloxy)-$C_{1-6}$-alkyl, ($C_{1-4}$-dialkylamino)-$C_{1-6}$-alkyl, $C_{1-4}$—($C_{3-6}$-cycloalkyl), $C_{1-4}$—($C_{5-6}$-heteroaryl), $C_{1-4}$—($C_{5-6}$-aryl), $C_{1-4}$—OH, $C_{1-4}$—$NH_2$, and $C_{1-4}$—CN;

wherein $R^{7a}$ and $R^{7b}$ are selected from $C_{1-6}$-alkyl, monohalo-$C_{1-6}$-alkyl, polyhalo-$C_{1-6}$-alkyl, ($C_{1-4}$-alkyloxy)-$C_{1-6}$-alkyl, ($C_{1-4}$-dialkylamino)-$C_{1-6}$-alkyl, $C_{1-4}$—($C_{3-6}$-cycloalkyl), $C_{1-4}$—($C_{5-6}$-heteroaryl), $C_{1-4}$—($C_{5-6}$-aryl), $C_{1-4}$—OH, $C_{1-4}$—$NH_2$, and $C_{1-4}$—CN, or may form a ring between $R^{7a}$ and $R^{7b}$ with $C_{3-7}$ carbons;

wherein $R^1$ is aryl or heteroaryl and substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl;

wherein $R^2$ is selected from heteroaryl, heterocycle, carbocycle containing a $C_{3-8}$ ring size, or acyclic $C_{1-6}$-alkyl;

wherein $R^2$ is substituted with 0, 1, 2, or 3 groups each independently selected from cyano, halo, hydroxyl, $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl;

wherein A is a 1,4-disubstituted aryl or heteroaryl ring substituted with X and $R^3$ and may contain a third group $R^6$ independently selected from cyano, halo, hydroxyl, $C_{1-3}$-alkyloxy, monohalo-$C_{1-3}$-alkyl, polyhalo-$C_{1-3}$-alkyl, sulfonyl-$C_{1-3}$-alkyl and sulfonamide;

wherein X is O, NH, or $NR^8$; wherein when X is $NR^8$, $R^8$ may be independently selected from $C_{1-3}$-alkyl, $C_{1-3}$-alkyloxy, monohalo-$C_{1-3}$-alkyl, polyhalo-$C_{1-3}$-alkyl, and sulfonyl-$C_{1-3}$-alkyl wherein $R^3$ is CN, $SO_2NH_2$, $SO_2NR^{9a}R^{9b}$, $CONR^{9a}R^{9b}$, $SO_2CH_3$, $OCF_3$, $CF_3$, Cl, $CH_2CN$, $CH_2NH_2$, $CH_2NHC(O)R^{10}$, $CH_2NHSO_2R^{10}$, $NO_2$, 4-pyridyl, 3-pyridyl, 1,2,3-triazole, $OCH_3$; wherein $R^{9a}$ and $R^{9b}$ may be independently selected from hydrogen, $C_{1-3}$-alkyl, or polyhalo-$C_{1-3}$-alkyl, or may form a ring between $R^{9a}$ and $R^{9b}$ with $C_{3-7}$ carbons; wherein $R^{10}$ is $C_{1-3}$-alkyl; or polyhalo-$C_{1-3}$-alkyl;

wherein $R^4$ is hydrogen, or $C_{1-3}$-alkyl; and wherein $R^5$ is hydrogen, OH, or $C_{1-3}$-alkyl.

2. The composition of claim 1, wherein one or both of $R^1$ and $R^2$ are phenyl.

3. The composition of claim 1, wherein $R^1$ is phenyl or substituted phenyl, and $R^2$ is a C5 carbocycle.

4. The composition of claim 1, wherein $R^1$ is phenyl or substituted phenyl, $R^2$ is heterocyclic or substituted heterocyclic.

5. The composition of claim 4, wherein $R^2$ is 2-heterocyclic or substituted 2-heterocyclic.

6. The composition of claim 1, wherein Y is $NH_2$, $NHR^7$, or $NR^{7a}R^{7b}$.

7. The composition of claim 1, wherein Y is OH or $OR^7$.

8. The composition of claim 1, wherein A is a 1,4-disubstituted phenyl group.

9. The composition of claim 8, wherein A is a phenyl group connected to the rest of the scaffold at the 1 position and comprising a substituent of 30 or fewer atoms at the 4 position.

10. The composition of claim 9, wherein said substituent at the 4 position comprises a heteroaryl.

11. The composition of claim 9, wherein said substituent at the 4 position comprises 5 or fewer atoms.

12. The composition of claim 11, wherein said substituent at the 4 position selected from the list consisting of CN, Cl, Br, $CF_3$, $OCF_3$, and $SO_2NH_2$.

13. The composition of claim 11, wherein $R^6$ is a halogen.

14. The composition of claim 1, wherein X is O.

15. The composition of claim 1, wherein one or both of $R^4$ and $R^5$ are H.

16. The composition of claim 15, wherein $R^4$ is H.

17. A composition comprising an effective amount of a compound selected from:

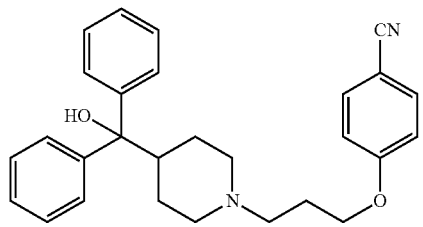 [SMILES: N#Cc1ccc(OCCCN2CCC(C(O)(c3ccccc3)c3ccccc3)CC2)cc1]
B1

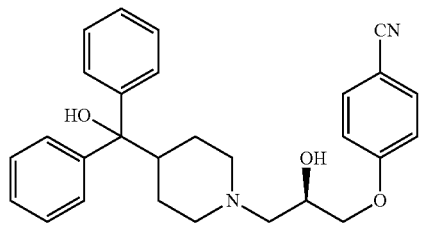 [SMILES: N#Cc1ccc(OC[C@H](O)CN2CCC(C(O)(c3ccccc3)c3ccccc3)CC2)cc1]
B2

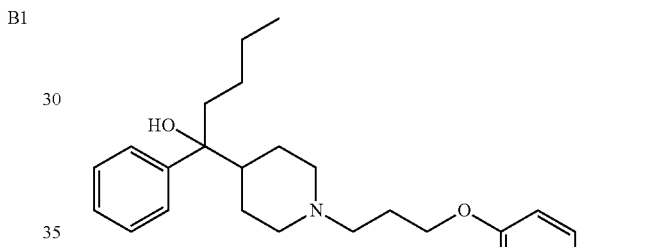
B3

B4

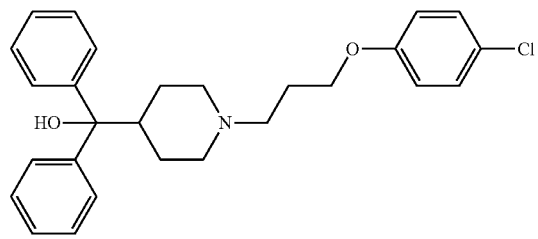 [SMILES: OC(c1ccccc1)(c1ccccc1)C1CCN(CCCOc2ccc(Cl)cc2)CC1]
B5

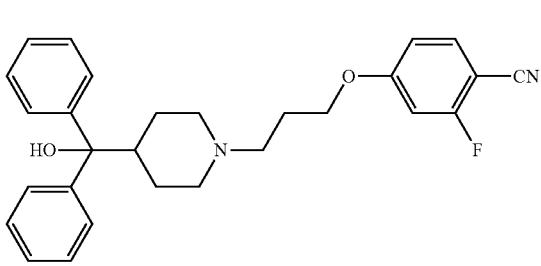 [SMILES: N#Cc1ccc(OCCCN2CCC(C(O)(c3ccccc3)c3ccccc3)CC2)cc1F]
B6

B7

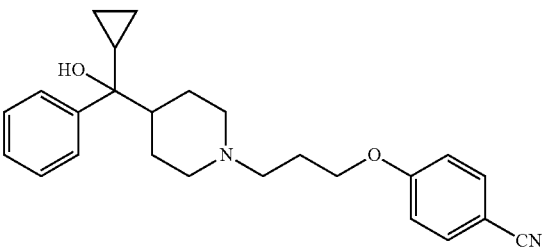 [SMILES: N#Cc1ccc(OCCCN2CCC(C(O)(c3ccccc3)C3CC3)CC2)cc1]
B8

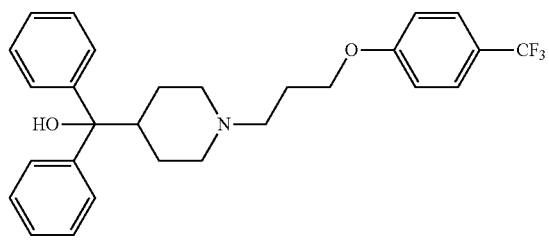

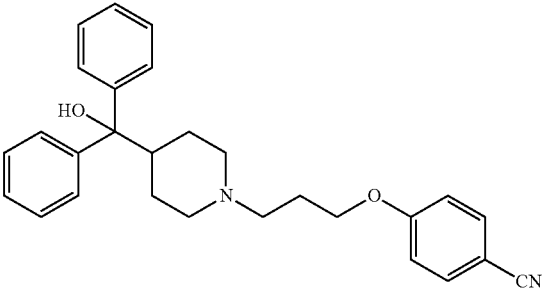 [SMILES: N#Cc1ccc(OCCCN2CCC(C(O)(c3ccccc3)c3ccccc3)CC2)cc1]
B9

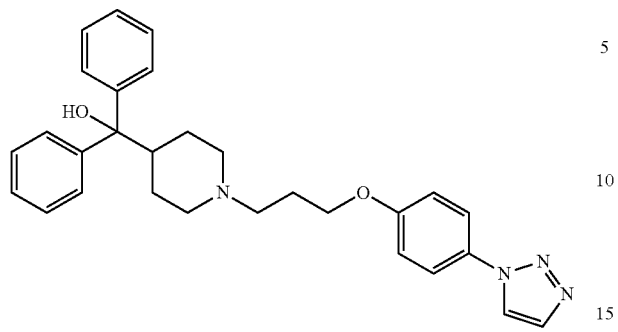
B10
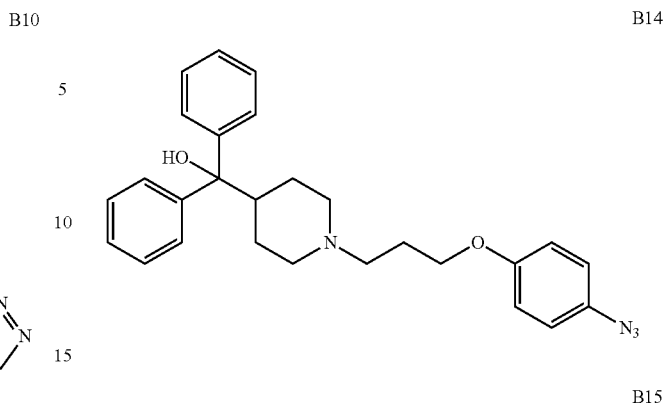
B14
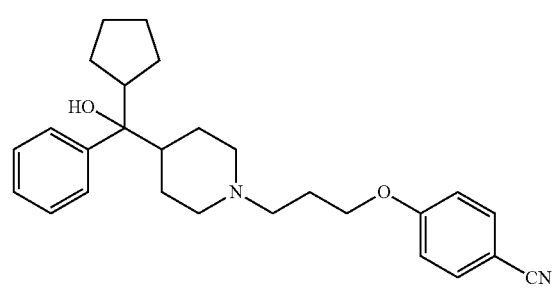 [SMILES: N#Cc1ccc(OCCCN2CCC(C(O)(c3ccccc3)C3CCCC3)CC2)cc1]
B11
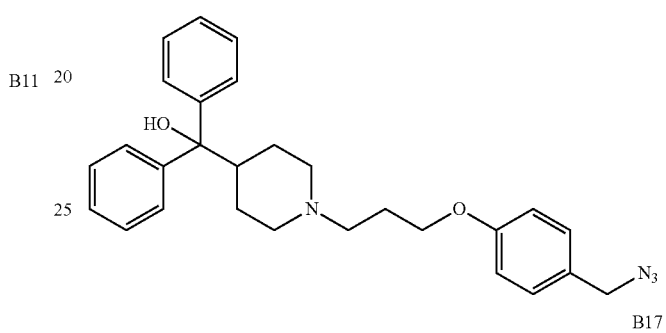
B15
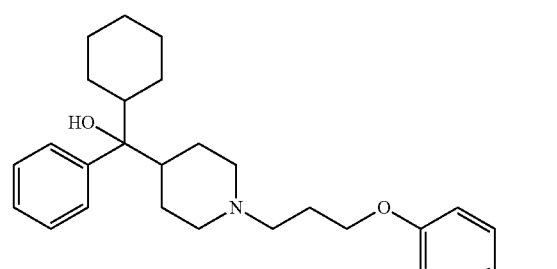
B12
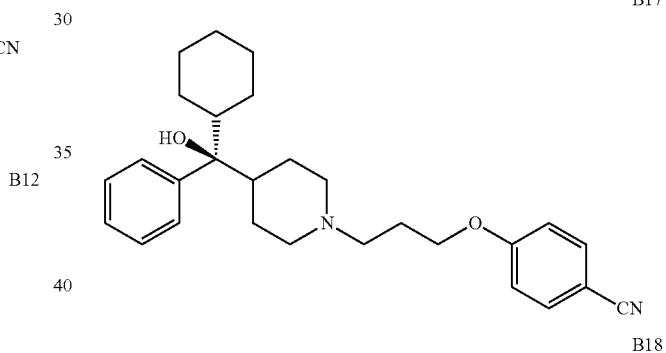
B17
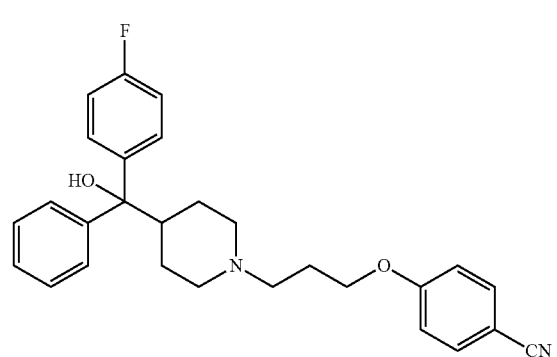 [SMILES: N#Cc1ccc(OCCCN2CCC(C(O)(c3ccccc3)c3ccc(F)cc3)CC2)cc1]
B13
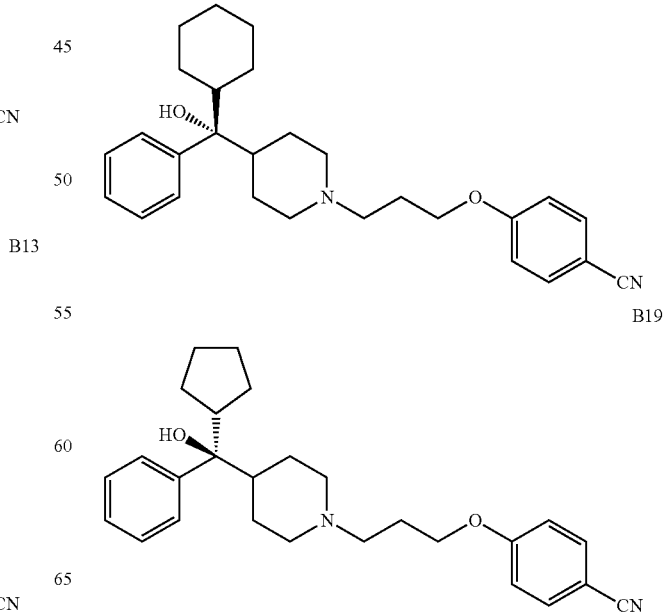
B18
B19

-continued
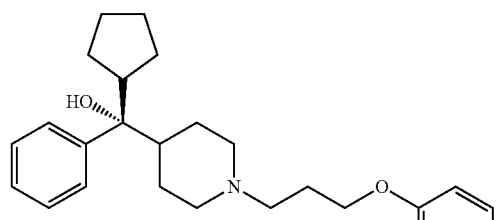
B20
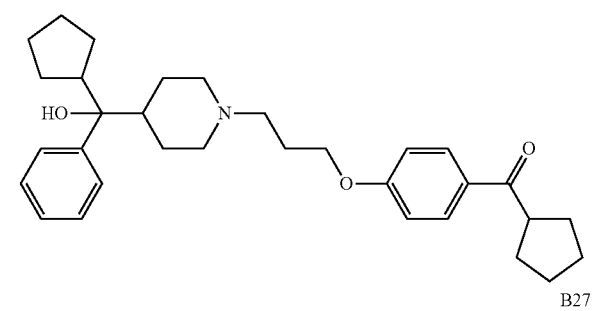
B26
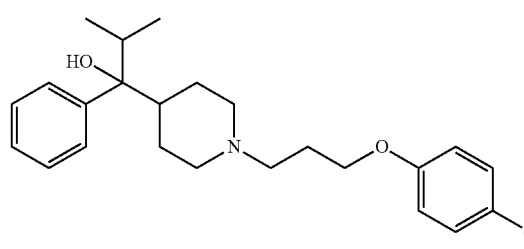
B21
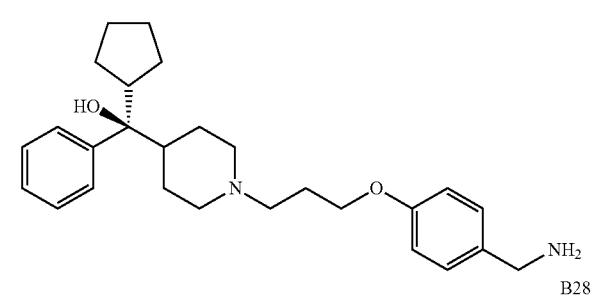
B27
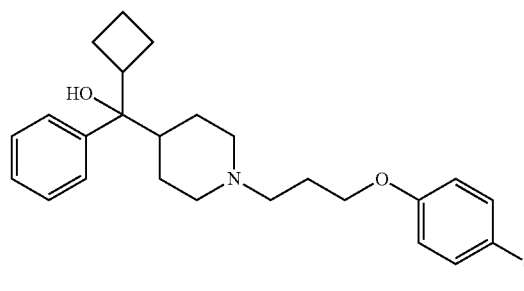
B22
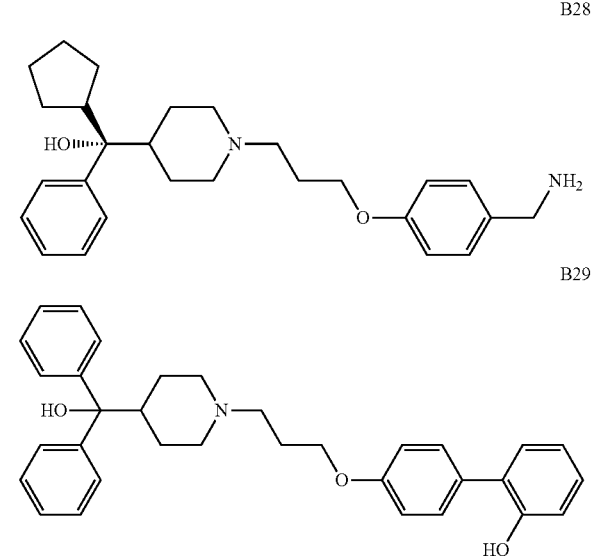
B28
B23
B29
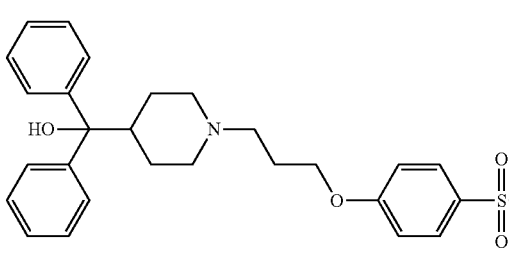
B24
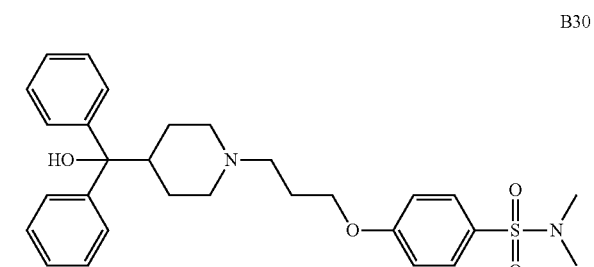
B30
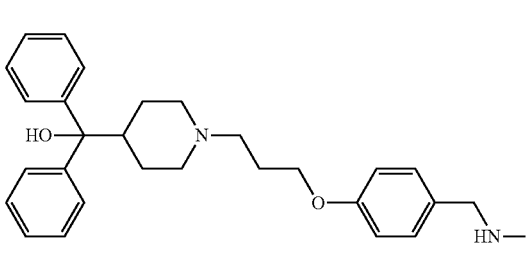
B25
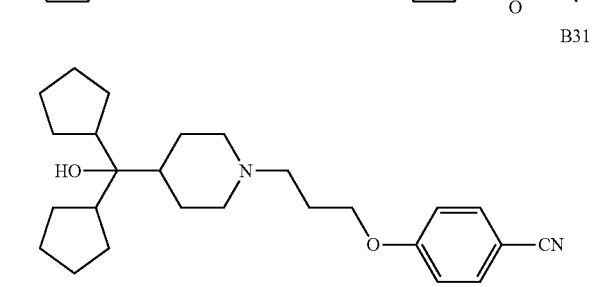
B31

B32
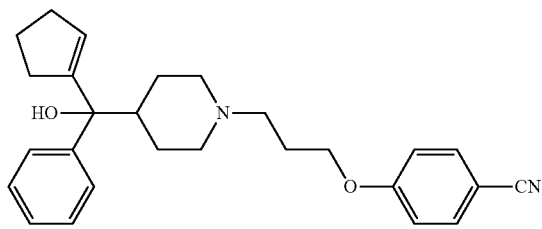 [SMILES: N#Cc1ccc(OCCCN2CCC(C(O)(C3=CCCC3)c3ccccc3)CC2)cc1]
B33
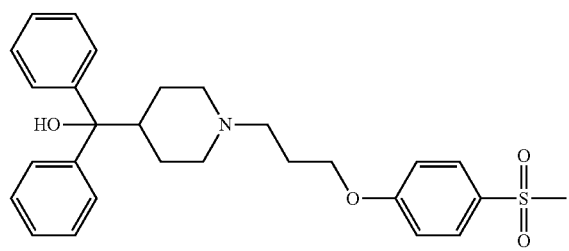 [SMILES: CS(=O)(=O)c1ccc(OCCCN2CCC(C(O)(c3ccccc3)c3ccccc3)CC2)cc1]
B34
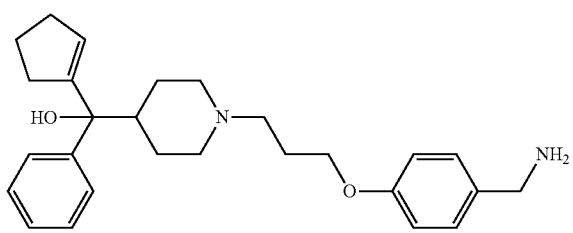 [SMILES: NCc1ccc(OCCCN2CCC(C(O)(C3=CCCC3)c3ccccc3)CC2)cc1]
B35
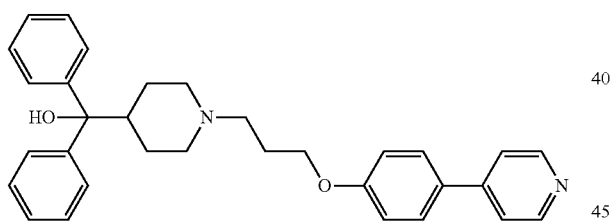
B36
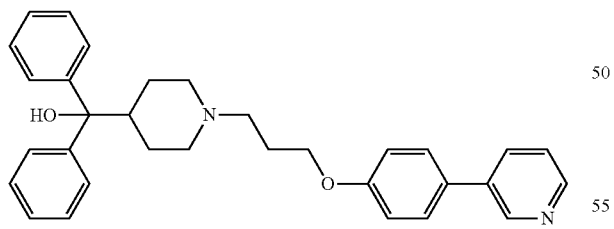
B37
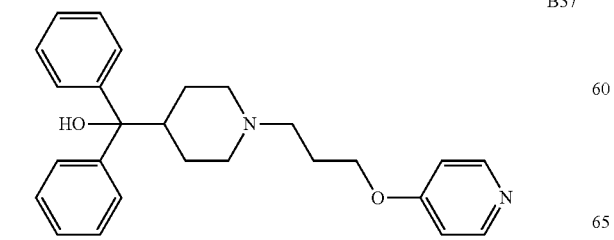
B38
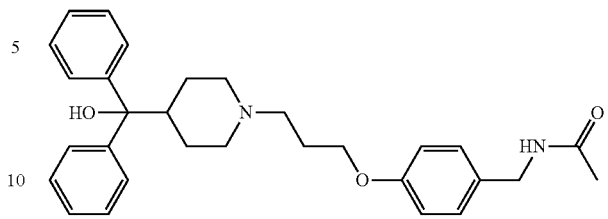
B39
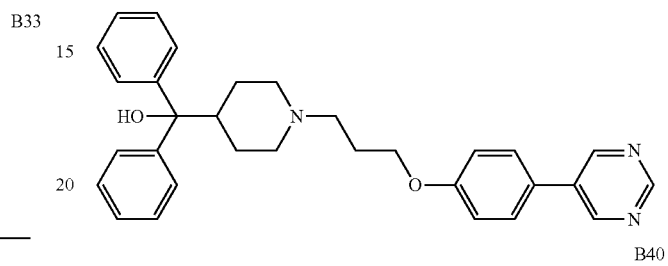
B40
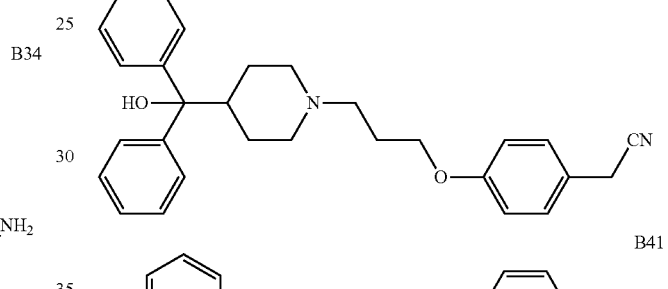
B41
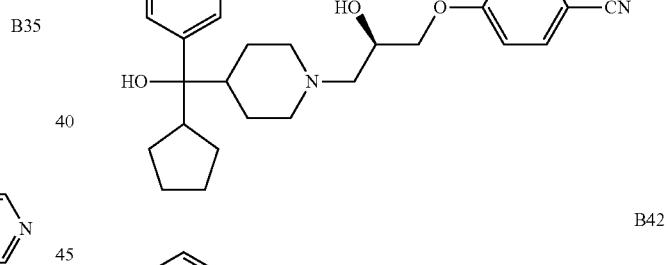
B42
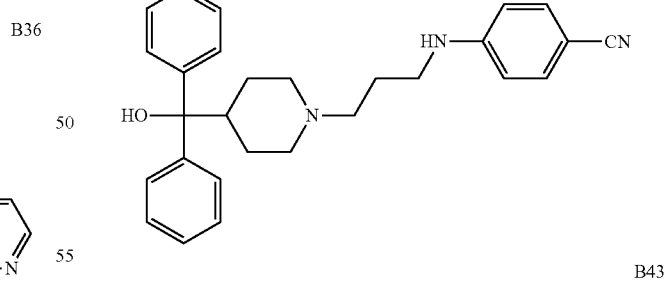
B43
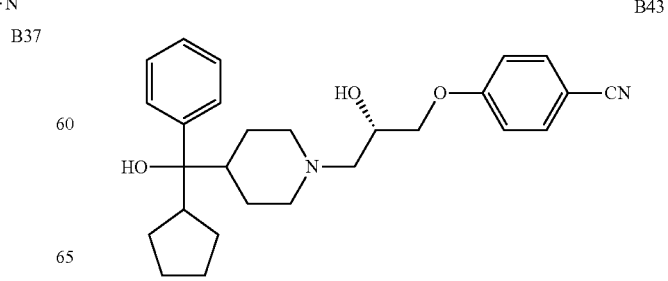

B44
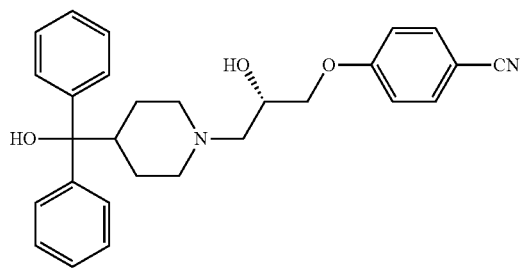 [SMILES: N#Cc1ccc(OC[C@@H](O)CN2CCC(C(O)(c3ccccc3)c3ccccc3)CC2)cc1]
B45
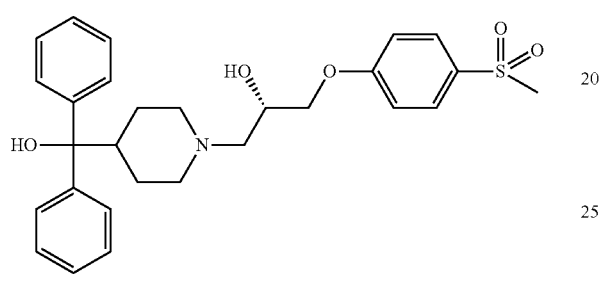
B46
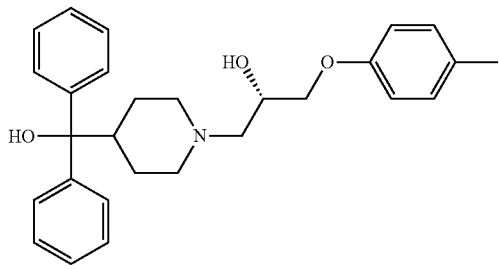 [SMILES: Cc1ccc(OC[C@@H](O)CN2CCC(C(O)(c3ccccc3)c3ccccc3)CC2)cc1]
B47
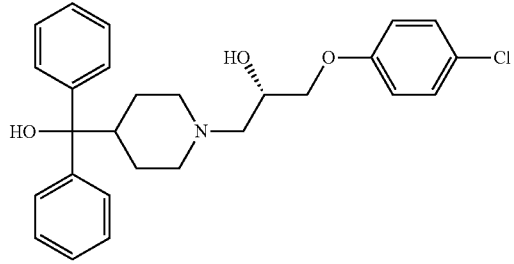 [SMILES: O[C@H](COc1ccc(Cl)cc1)CN1CCC(C(O)(c2ccccc2)c2ccccc2)CC1]
B48
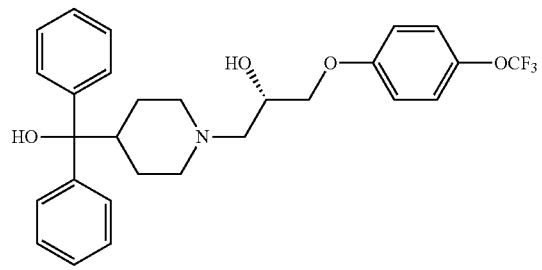 [SMILES: O[C@H](COc1ccc(OC(F)(F)F)cc1)CN1CCC(C(O)(c2ccccc2)c2ccccc2)CC1]
B49
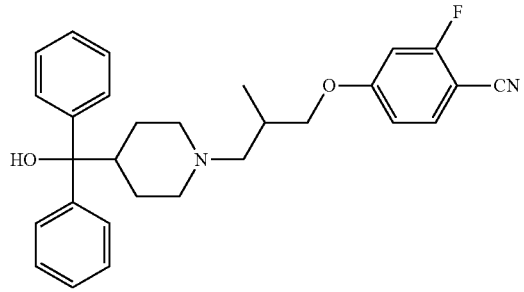 [SMILES: CC(COc1ccc(C#N)c(F)c1)CN1CCC(C(O)(c2ccccc2)c2ccccc2)CC1]
B50
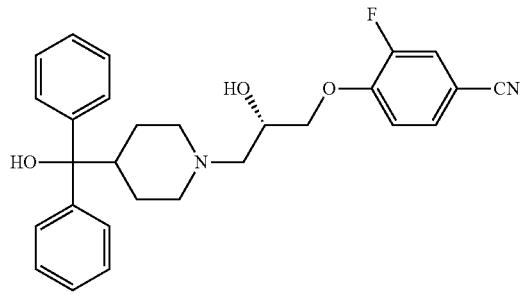 [SMILES: N#Cc1ccc(OC[C@@H](O)CN2CCC(C(O)(c3ccccc3)c3ccccc3)CC2)c(F)c1]
B51
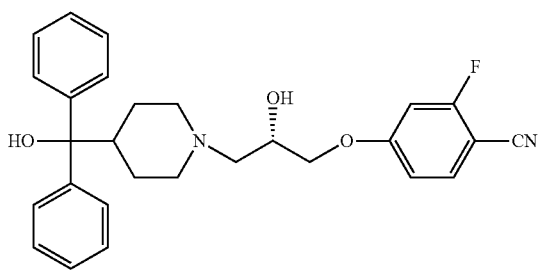 [SMILES: N#Cc1ccc(OC[C@@H](O)CN2CCC(C(O)(c3ccccc3)c3ccccc3)CC2)cc1F]
B52
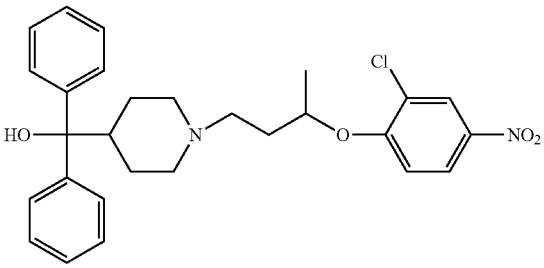 [SMILES: CC(CCN1CCC(C(O)(c2ccccc2)c2ccccc2)CC1)Oc1ccc([N+](=O)[O-])cc1F]
B53
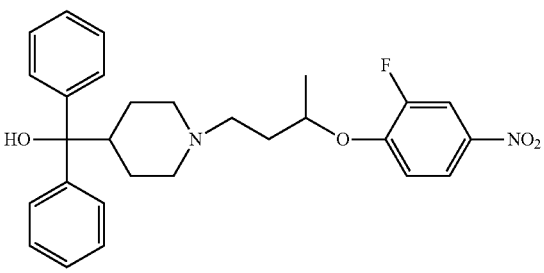

B54
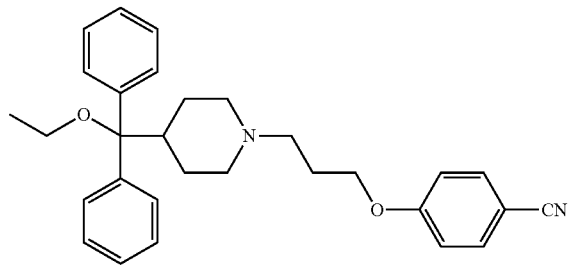 [SMILES: CCOC(c1ccccc1)(c1ccccc1)C1CCN(CCCOc2ccc(C#N)cc2)CC1]
B55
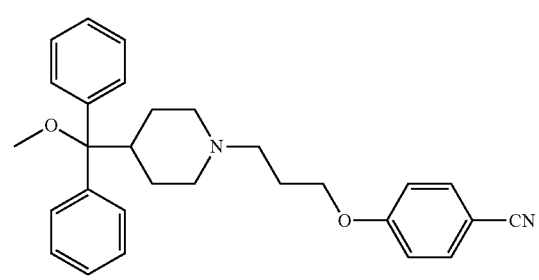 [SMILES: COC(c1ccccc1)(c1ccccc1)C1CCN(CCCOc2ccc(C#N)cc2)CC1]
B56
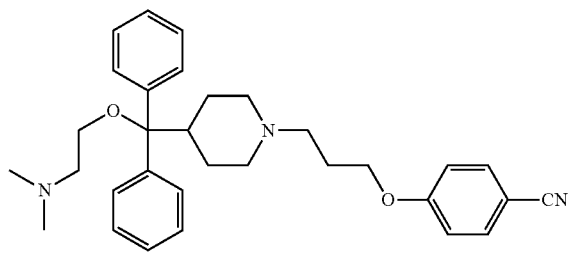 [SMILES: CN(C)CCOC(c1ccccc1)(c1ccccc1)C1CCN(CCCOc2ccc(C#N)cc2)CC1]
B57
B58
B59
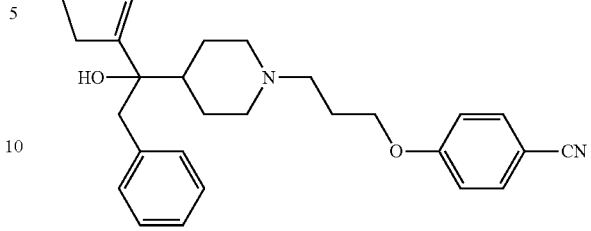
B60
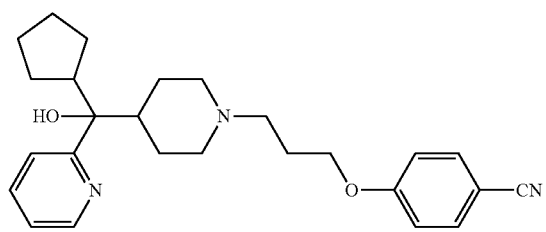 [SMILES: N#Cc1ccc(OCCCN2CCC(C(O)(c3ccccn3)C3CCCC3)CC2)cc1]
B61
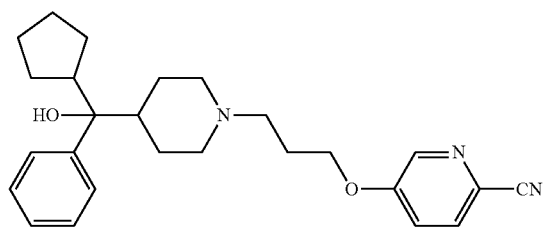 [SMILES: N#Cc1ccc(OCCCN2CCC(C(O)(c3ccccc3)C3CCCC3)CC2)cn1]
B62
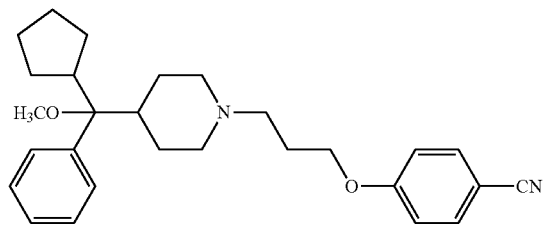 [SMILES: COC(c1ccccc1)(C1CCCC1)C1CCN(CCCOc2ccc(C#N)cc2)CC1]
B63
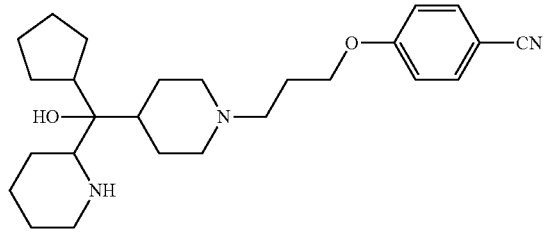 [SMILES: N#Cc1ccc(OCCCN2CCC(C(O)(C3CCCC3)C3CCCCN3)CC2)cc1]
B64
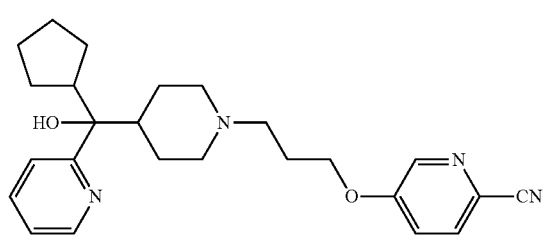

B65
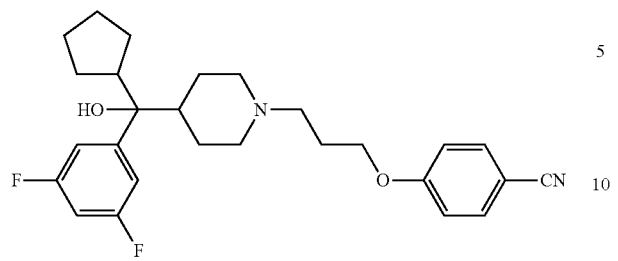
B66
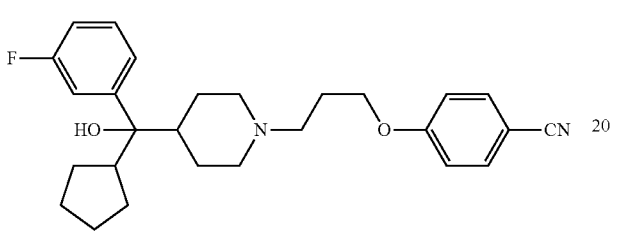
B67
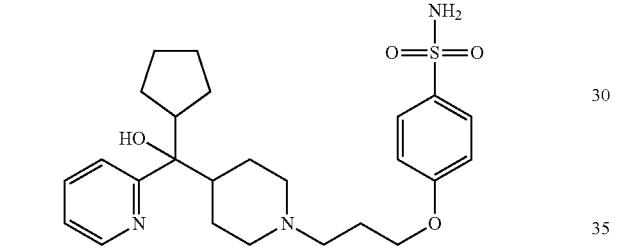
B68
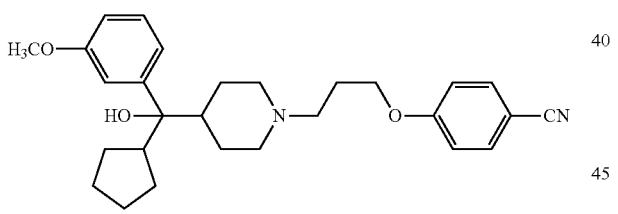
B69
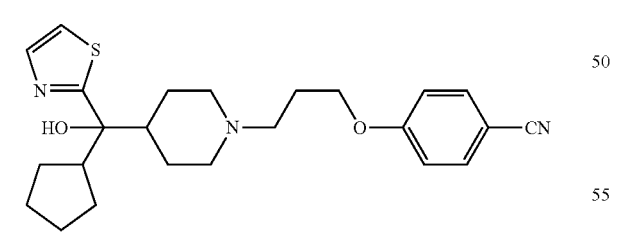
B70
B71
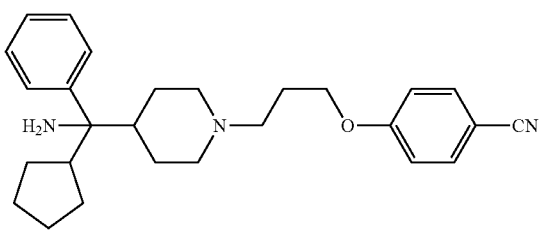 [SMILES: N#Cc1ccc(OCCCN2CCC(C(N)(c3ccccc3)C3CCCC3)CC2)cc1]
B72
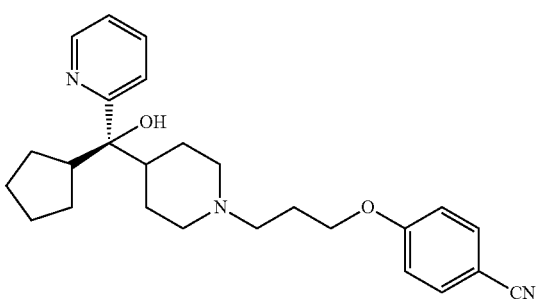 [SMILES: N#Cc1ccc(OCCCN2CCC([C@@](O)(c3ccccn3)C3CCCC3)CC2)cc1]
B73
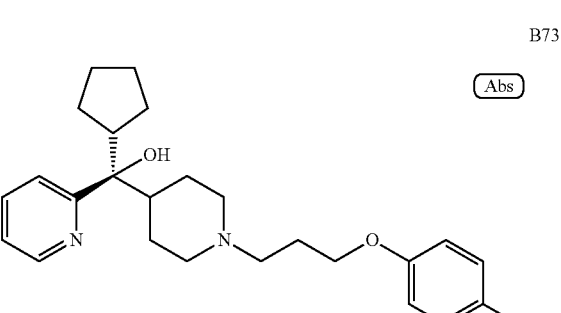
B74
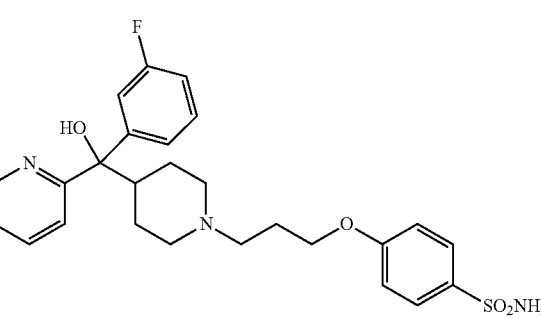
B75
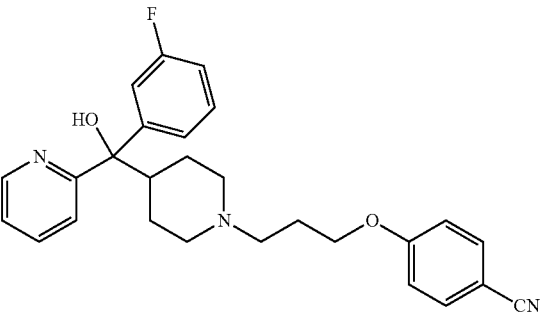 [SMILES: N#Cc1ccc(OCCCN2CCC(C(O)(c3cccc(F)c3)c3ccccn3)CC2)cc1]

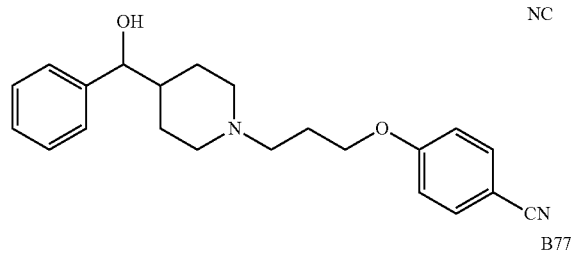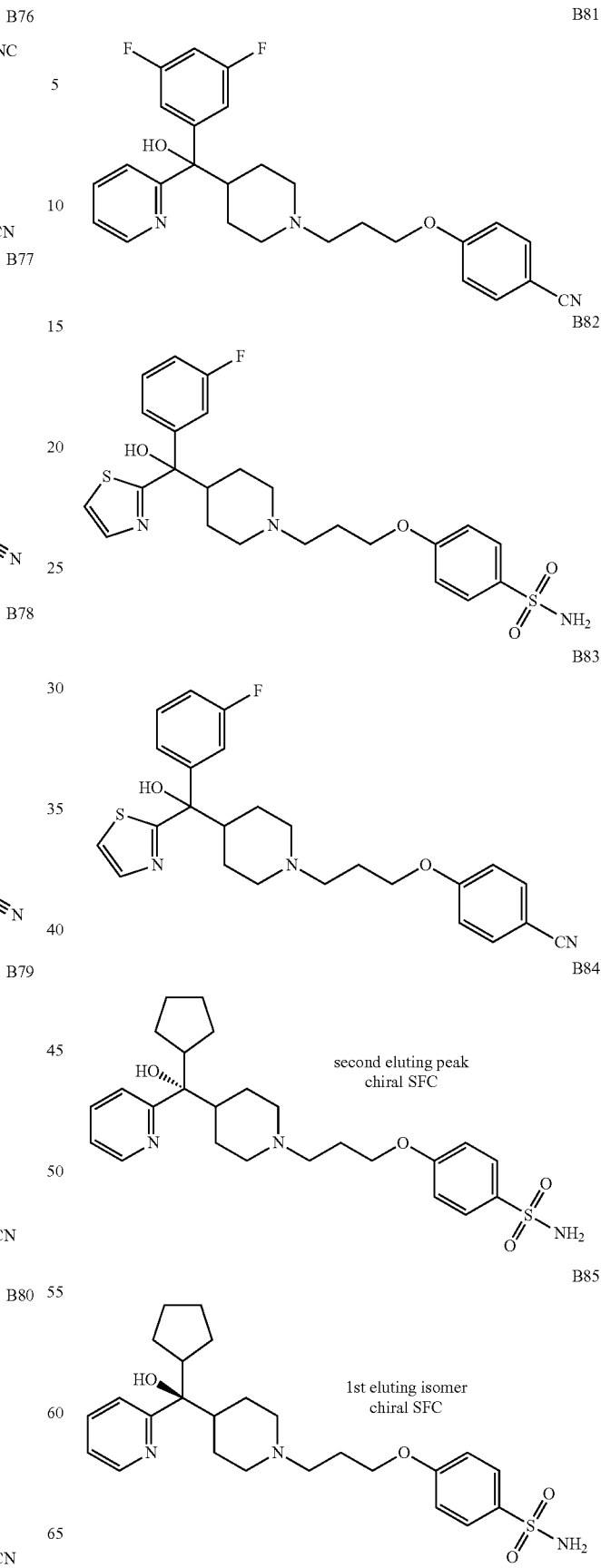

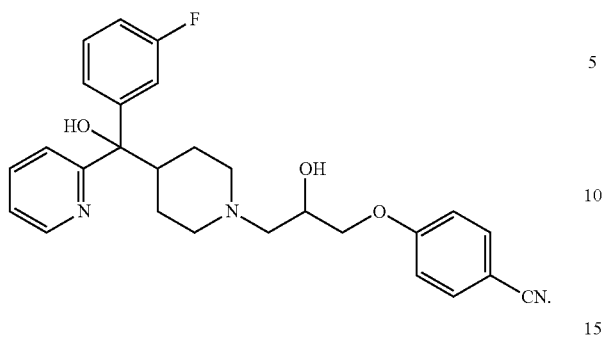
B86
18. A method for the treatment of leukemia or other hematological malignancies, or diabetes comprising administering a composition of claim 1 to a subject suffering from said disease.
19. The method of claim 18, wherein said leukemia comprises AML or ALL.
* * * * *

UNITED STATES PATENT AND TRADEMARK OFFICE
CERTIFICATE OF CORRECTION

PATENT NO.         : 9,212,180 B2  
APPLICATION NO.    : 14/302219  
DATED              : December 15, 2015  
INVENTOR(S)        : Jolanta Grembecka et al.

Page 1 of 1

It is certified that error appears in the above-identified patent and that said Letters Patent is hereby corrected as shown below:

Claim 1, column 78, line 13 should read
$NHR^7$, or $NR^{7a}R^{7b}$;

Signed and Sealed this  
Nineteenth Day of April, 2016

Michelle K. Lee  
*Director of the United States Patent and Trademark Office*